US008101359B2

(12) United States Patent
Foekens et al.

(10) Patent No.: US 8,101,359 B2
(45) Date of Patent: *Jan. 24, 2012

(54) METHOD FOR DETERMINING RISK OF RELAPSE OF BREAST CANCER FOLLOWING TAMOXIFEN ADJUVANT THERAPY

(75) Inventors: John Foekens, Rotterdam (NL); Nadia Harbeck, Otterfing (DE); Thomas Koenig, Berlin (DE); Sabine Maier, Brussels (BE); John W. Martens, Rotterdam (NL); Fabian Model, Berlin (DE); Inko Nimmrich, Berlin (DE); Tamas Rujan, Berlin (DE); Armin Schmitt, Berlin (DE); Manfred Schmitt, Munich (DE); Maxime P. Look, Amsterdam (NL); Almuth Marx, Nuremberg (DE); Heinz Hoefler, Munich (DE)

(73) Assignee: Epigenomics AG, Berlin (DE)

( * ) Notice: Subject to any disclaimer, the term of this patent is extended or adjusted under 35 U.S.C. 154(b) by 527 days.

This patent is subject to a terminal disclaimer.

(21) Appl. No.: 10/517,741

(22) PCT Filed: Oct. 1, 2003

(86) PCT No.: PCT/EP03/10881
§ 371 (c)(1),
(2), (4) Date: Jan. 3, 2006

(87) PCT Pub. No.: WO2004/035803
PCT Pub. Date: Apr. 29, 2004

(65) Prior Publication Data
US 2006/0121467 A1    Jun. 8, 2006

(30) Foreign Application Priority Data

Oct. 1, 2002 (DE) .................. 102 45 779
Jan. 7, 2003 (DE) .................. 103 00 096
Apr. 17, 2003 (DE) .................. 103 17 955

(51) Int. Cl.
C12Q 1/68 (2006.01)
C12P 19/34 (2006.01)
C07H 21/02 (2006.01)
C07H 21/04 (2006.01)

(52) U.S. Cl. ...... 435/6.11; 435/6.1; 435/6.12; 435/6.14; 435/91.2; 536/23.5; 536/24.31

(58) Field of Classification Search .................. None
See application file for complete search history.

(56) References Cited

U.S. PATENT DOCUMENTS 5,744,305 A    4/1998    Fodor et al.
5,786,146 A    7/1998    Herman et al.
5,837,832 A    11/1998    Chee et al.
6,265,171 B1    7/2001    Herman et al.
6,331,393 B1    12/2001    Laird et al.
6,596,488 B2    7/2003    Pfeifer et al.
7,125,663 B2 *    10/2006    Schlegel et al. ............ 435/6
2004/0033547 A1 *    2/2004    Field et al. ............ 435/7.32
2006/0121467 A1 *    6/2006    Foekens et al. ............ 435/6
2008/0254447 A1 *    10/2008    Foekens et al. ............ 435/6

FOREIGN PATENT DOCUMENTS

| DE | 10245779.4 | 10/2002 |
| DE | 10300096.8 | 1/2003 |
| DE | 10317955.0 | 4/2003 |
| EP | 1167975 | 1/2002 |
| WO | WO 95/00669 | 1/1995 |
| WO | WO 95/15373 | 6/1995 |
| WO | WO 97/45560 | 12/1997 |
| WO | WO 97/46705 | 12/1997 |
| WO | WO 99/28498 | 6/1999 |
| WO | WO 01/19845 | 3/2001 |
| WO | WO 01/019845 | * 3/2001 |
| WO | WO 01/68912 | 9/2001 |
| WO | WO 01/81622 | 11/2001 |
| WO | WO 02/02806 | 1/2002 |
| WO | WO 02/059347 | 8/2002 |
| WO | WO 02/077272 | * 10/2002 |
| WO | WO 03/052135 | 6/2003 |

OTHER PUBLICATIONS

Dermer, G.B. Bio/Technology (1994) 12: 320.*
Martens et al. Cancer Research. 2005. 65(10): 4101-4107.*
Nimmrich et al. Breast Cancer Research and Treatment. 2008. 111:429-437.*
Ushijima, T. Nature Reviews. 2005. 5: 223-231.*
Berns et al., "Predictive value of SRC-1 for taxomifen response of recurrent breast cancer," Breast Cancer Research and Treatment, 1998, pp. 87-92, vol. 48.
Bieche et al., "The CGA gene as new predictor of the response to endocrine therapy in ERα-positive menopausal breast cancer patients," Oncogene, 2001, pp. 6955-6959, vol. 20.
Bieche et al., "Identification of CGA as a Novel Estrogen Receptor-responsive Gene in Breast Cancer: An Outstanding Candidate Marker to Predict the Response to Endocrine Therapy," Cancer Research, Feb. 15, 2001, pp. 1652-1658, vol. 61.
Brattsand, "Correlation of oncoprotein 18/stathmin expression in human breast cancer with established prognostic factors," British Journal of Cancer, 2000, pp. 311-318, vol. 83, No. 3.
Chang et al., "Prediction of Clinical Outcome from Primary Tamoxifen by Expression of Biologic Markers in Breast Cancer Patients," Clinical Cancer Research, Feb. 2000, pp. 616-621, vol. 6.
Ciocca et al., "Molecular Markers for Predicting Response to Tamoxifen in Breast Cancer Patients," Endocrine, Aug. 2000, pp. 1-10, vol. 13, No. 1.
Curmi et al., "Overexpression of stathmin in breast carcinomas points out to highly proliferative tumours," British Journal of Cancer, 2000, pp. 142-150, vol. 82, No. 1.

(Continued)

Primary Examiner — Carla Myers
(74) Attorney, Agent, or Firm — DLA Piper LLP (US)

(57) ABSTRACT

The present invention relates to modified and genomic sequences, to oligonucleotides and/or PNA-oligomers for detecting the cytosine methylation state of genomic DNA, as well as to a method for predicting the response of a subject with a cell proliferative disorder of the breast tissues, to endocrine treatment.

14 Claims, 23 Drawing Sheets

OTHER PUBLICATIONS

Dudoit et al., "Statistical Methods for Identifying Differentially Expressed Genes in Replicated cDNA Microarray Experiments," Statistica Sinica, 2002, pp. 111-139, vol. 12.

Elledge et al., "bcl-2, p53, and Response to Tamoxifen in Estrogen Receptor-Positive Metastatic Breast Cancer: A Southwest Oncology Group Study," Journal of Clinical Oncology, May 1997, pp. 1916-1922, vol. 15, No. 5.

Farczádi et al., "Changes in apoptosis, mitosis, Her-2, p53 and Bcl2 expression in breast carcinomas after short-term tamoxifen treatment," Neoplasma, 2002, pp. 101-103, vol. 49, No. 2.

Feil et al., "Methylation analysis on individual chromosomes: improved protocol for bisulphite genomic sequencing," Nucleic Acids Research, 1994, pp. 695-696, vol. 22, No. 4.

Gitan et al., "Methylation-Specific Oligonucleotide Microarray: A New Potential for High-Throughput Methylation Analysis," Genome Research, 2001, pp. 158-164, vol. 12.

Goldhirsch et al., "Meeting Highlights: International Consensus Panel on the Treatment of Primary Breast Cancer," Journal of the National Cancer Institute, Nov. 4, 1998, pp. 1601-1608, vol. 90, No. 21.

Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.

Gough et al., "Identification of the primary gene defect at the cytochrome P450 CYP2D locus," Nature, Oct. 25, 1990, pp. 773-776, vol. 347, No. 6295.

Grigg et al., "Sequencing 5-Methylcytosine Residues in Genomic DNA," BioEssays, Jun. 1994, pp. 431-436, vol. 16, No. 6.

Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.

Gut et al., "A procedure for selection DNA alkylation and detection by mass spectrometry," Nucleic Acids Research, 1995, pp. 1367-1373, vol. 23, No. 8.

Harbeck et al., "Clinical Relevance of Invasion Factors Urokinase-Type Plasminogen Activator and Plasminogen Activator Inhibitor Type 1 for Individualized Therapy Decisions in Primary Breast Cancer Is Greatest When Used in Combination," Journal of Clinical Oncology, Feb. 15, 2002, pp. 1000-1007, vol. 20, No. 4.

Heid et al., "Real Time Quantitative PCR," Genome Research, 1996, pp. 986-994, vol. 6.

Herman et al., "Methylation-specific PCR: A novel PCR assay for methylation status of CpG islands," Sep. 1996, pp. 9821-9826, vol. 93.

Houston et al., "Overexpression of c-erbB2 is an independent marker of resistance to endocrine therapy in advanced breast cancer," British Journal of Cancer, 1999, pp. 1220-1226, vol. 79, No. 7/8.

Huang et al., "Methylation profiling of CpG islands in human breast cancer cells," Human Molecular Genetics, 1999, pp. 459-470, vol. 8, No. 3.

Huber et al., "Variance stabilization applied to microarray data calibration and to the quantification of differential expression," Bioinformatics, 2002, pp. S96-S104, vol. 18, Supplement 1.

Kang et al., "Methylation in th ep53 Promoter Is a Supplementary Route to Breast Carcinogenesis: Correlation between CpG Methylation in the p53 Promoter and the Mutation of the p53 Gene in the Progression from Ductal Carcinoma In Situ to Invasive Ductal Carcinoma," Laboratory Investigation, 2001, pp. 573-579, vol. 81, No. 4.

Karas et al., "Laser Desorption Ionization of Proteins with Molecular Masses Exceeding 10 000 Daltons," Analytical Chemistry, Oct. 15, 1988, pp. 2299-2301, vol. 60, No. 20.

Kim et al., "Hypermethylation of RASSF1A Promoter Is Associated with the Age at Starting Smoking and a Poor Prognosis in Primary Non-Small Cell Lung Cancer," Cancer Research, Jul. 1, 2003, pp. 3743-3746, vol. 63.

Kuzmin et al., "Inactivation of RAS Association Domain Family 1A Gene in Cervical Carcinomas and the Role of Human Papillomavirus Infection," Cancer Research, Apr. 15, 2003, pp. 1888-1893, vol. 63.

Lapidus et al., "Methylation of Estrogen and Progesterone Receptor Gene 5' CpG Islands Correlates with Lack of Estrogen and Progesterone Receptor Gene Expression in Breast Tumors," Clinical Cancer Research, May 1996, pp. 805-810, vol. 2.

Lücke et al., "Inhibiting Mutations in the Transforming Growth Factor β Type 2 Receptor in Recurrent Human Breast Cancer," Cancer Research, Jan. 15, 2001, pp. 482-485, vol. 61.

Martens et al., "Epigenetic signature predicts failure of endocrine therapy in patients with recurrent breast cancer," Breast Cancer Research and Treatment, Jun. 3, 2003, p. S72, vol. 82, No. Supp. 1, abstract only.

Martin et al., "Genomic sequencing indicates a correlation between DNA hypomethylation in the 5' region on the pS2 gene and its expression in human breast cancer cell lines," Gene, 1995, pp. 261-264, vol. 157.

Martin et al., "Involvement of DNA Methylation in the Control of the Expression of an Estrogen-Induced Breast-Cancer-Associated Protein (pS2) in Human Breast Cancers," Journal of Cellular Biochemistry, 1997, pp. 95-106, vol. 65.

Model et al., "Statistical process control for large scale microarray experiments," Bioinformatics, 2002, pp. S155-S163, vol. 18, Supplement 1.

Ojala et al., "mRNA differential display of gene expression in colonic carcinoma," Electrophoresis, Jun. 2002, pp. 1667-1676, vol. 23, No. 11.

Olek et al., "A modified and improved method for bisulphite based cytosine methylation analysis," Nucleic Acids Research, 1996, pp. 5064-5066, vol. 24, No. 24.

Olek et al., "The pre-implantation ontogeny of the H19 methylation imprint," Nature Genetics, Nov. 1997, pp. 275-276, vol. 17.

Ottaviano et al., "Methylation of the Estrogen Receptor Gene CpG Island Marks Loss of Estrogen Receptor Expression in Human Breast Cancer Cells," Cancer Research, May 15, 1994, pp. 2552-2555, vol. 54.

Pichon et al., "Clinical significance of the estrogen regulated pS2 protein in mammary tumours," Critical Reviews Oncology/Hematology, Aug. 1993, pp. 13-21, vol. 15, No. 1.

Raman et al., "Compromised HOXA5 function can limit p53 expression in human breast tumors," Nature, Jun. 22, 2000, pp. 974-978, vol. 405.

Rein et al., "Survey and Summary Identifying 5-methylcytosine and related modifications in DNA genomes," Nucleic Acids Research, 1998, pp. 2255-2264, vol. 26, No. 10.

Rodrigues et al., "Cytochrome P450 Pharmacogenetics in Drug Development: In Vitro Studies and Clinical Consequences," Current Drug Metabolism, Jun. 2002, pp. 289-309, vol. 3, No. 3.

Sakai et al., "Prognostic Significance of β-Microseminoprotein mRNA Expression in Prostate Cancer," The Prostate, Mar. 1, 1999, pp. 278-284, vol. 38, No. 4.

Sanger et al., "DNA sequencing with chain-terminating inhibitors," PNAS, Dec. 1977, pp. 5463-5467, vol. 74, No. 12.

Umbricht et al., "Hypermethylation of 14-3-3 α (stratifin) is an early event in breast cancer," Oncogene, 2001, pp. 3348-3353, vol. 20.

Virmani et al., "Hierarchical Clustering of Lung Cancer Cell Lines Using DNA Methylation Markers," Cancer Epidemiology, Biomarkers & Prevention, Mar. 2002, pp. 291-297, vol. 11.

Watanabe et al., "Isolation of Estrogen-Responsive Genes with a CpG Island Library," Molecular and Cellular Biology, Jan. 1998, pp. 442-449, vol. 18, No. 1.

Xiong et al., "Cobra: a sensitive and quantitative DNA methylation assay," Nucleic Acids Research, 1997, pp. 25322534, vol. 25, No. 12.

Yan et al., "Dissecting Complex Epigenetic Alterations in Breast Cancer Using CpG Island Microarrays," Cancer Research, Dec. 1, 2001, pp. 8375-8380, vol. 61.

Yu et al., "Specific Inhibition of PCR by Non-Extendable Oligonucleotides Using a 5' to 3' Exonuclease-Deficient DNA Polymerase," BioTechniques, 1997, pp. 714-720, vol. 23, No. 4.

Yuan et al., "Hypermethylation Leads to Silencing of the SYK Gene in Human Breast Cancer," Cancer Research, Jul. 15, 2001, pp. 5558-5561, vol. 61.

Zeschnigk et al., "Imprinted segments in the human genome: different DNA methylation pattersn in the Prader-Willi/Angelman syndrome region as determined by the genomic sequencing method," Human Molecular Genetics, 1997, pp. 387-395, vol. 6, No. 3.

Zeschnigk et al., "A single-tube PCR test for the diagnosis of Angelman and Prader-Willi syndrome based on allelic methylation differences at the SNRPN locus," European Journal of Human Genetics, Mar.-Apr. 1997, pp. 94-98, vol. 5, No. 2.

Eckhardt et al., "DNA methylation profiling of human chromosomes 6, 20 and 22," Nature Genetics, 2006, pp. 1378-1375, vol. 38.

Perou et al., "Molecular portraits of human breast tumors," Nature, 2000, pp. 747-752, vol. 406.

Sorlie et al., "Gene expression patterns of breast carcinomas distinguish tumor subclasses with clinical implications," The Proceedings of the National Academy of Sciences, 2001, pp. 10869-10874, vol. 98.

Taylor et al., "Ultradeep Bisulfite Sequencing Analysis of DNA Methylation Patterns in Multiple Gene Promoters by 454 Sequencing," Cancer Research, 2007, pp. 8511-8518, vol. 67.

* cited by examiner

METHOD FOR DETERMINING RISK OF RELAPSE OF BREAST CANCER FOLLOWING TAMOXIFEN ADJUVANT THERAPY

CROSS-REFERENCE TO RELATED APPLICATIONS

This application claims the benefit of priority to the following applications: International application number PCT/EP2003/010881, filed 1 Oct. 2003 and published as WO 2004/035803; German application number 10245779.4, filed 1 Oct. 2002; German application number 10300096.8, filed 7 Jan. 2003; and German application number 10317955.0, filed 17 Apr. 2003; all of which are incorporated by reference herein in their entireties.

FIELD OF THE INVENTION

The present invention relates to genomic DNA methylation and to patients with breast cell proliferative disorders (e.g., breast cancer). Particular embodiments of the invention provide novel compositions, and methods for the diagnosis of individuals with said disorders.

SEQUENCE LISTING

A Sequence Listing, pursuant to 37 C.F.R. §1.52(e)(5), has been provided on compact disc (1 of 1) as a 5.34 MB text file, entitled "47675-93 Sequence Listing.txt," and which is incorporated by reference herein in its entirety.

BACKGROUND

The levels of observation that have been studied by the methodological developments of recent years in molecular biology, are the genes themselves, the translation of these genes into RNA, and the resulting proteins. The question of which gene is switched on at which point in the course of the development of an individual, and how the activation and inhibition of specific genes in specific cells and tissues are controlled is correlatable to the degree and character of the methylation of the genes or of the genome. In this respect, pathogenic conditions may manifest themselves in a changed methylation pattern of individual genes or of the genome.

DNA methylation plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing since 5-methylcytosine has the same base pairing behaviour as cytosine. Moreover, the epigenetic information carried by 5-methylcytosine is completely lost during PCR amplification.

A relatively new and currently the most frequently used method for analysing DNA for 5-methylcytosine is based upon the specific reaction of bisulfite with cytosine which, upon subsequent alkaline hydrolysis, is converted to uracil which corresponds to thymidine in its base pairing behaviour. However, 5-methylcytosine remains unmodified under these conditions. Consequently, the original DNA is converted in such a manner that methylcytosine, which originally could not be distinguished from cytosine by its hybridisation behaviour, can now be detected as the only remaining cytosine using "normal" molecular biological techniques, for example, by amplification and hybridisation or sequencing. All of these techniques are based on base pairing which can now be fully exploited. In terms of sensitivity, the prior art is defined by a method which encloses the DNA to be analysed in an agarose matrix, thus preventing the diffusion and renaturation of the DNA (bisulfite only reacts with single-stranded DNA), and which replaces all precipitation and purification steps with fast dialysis (Olek A, Oswald J, Walter J. A modified and improved method for bisulphite based cytosine methylation analysis. Nucleic Acids Res. 1996 Dec. 15; 24(24):5064-6). Using this method, it is possible to analyse individual cells, which illustrates the potential of the method. However, currently only individual regions of a length of up to approximately 3000 base pairs are analysed, a global analysis of cells for thousands of possible methylation events is not possible. However, this method cannot reliably analyse very small fragments from small sample quantities either. These are lost through the matrix in spite of the diffusion protection.

An overview of the further known methods of detecting 5-methylcytosine may be gathered from the following review article: Rein, T., DePamphilis, M. L., Zorbas, H., Nucleic Acids Res. 1998, 26, 2255.

To date, barring few exceptions (e.g., Zeschnigk M, Lich C, Buiting K, Doerfler W, Horsthemke B. A single-tube PCR test for the diagnosis of Angelman and Prader-Willi syndrome based on allelic methylation differences at the SNRPN locus. Eur J Hum Genet. 1997 March-April; 5(2):94-8) the bisulfite technique is only used in research. Always, however, short, specific fragments of a known gene are amplified subsequent to a bisulfite treatment and either completely sequenced (Olek A, Walter J. The pre-implantation ontogeny of the H19 methylation imprint. Nat Genet. 1997 November; 17(3):275-6) or individual cytosine positions are detected by a primer extension reaction (Gonzalgo M L, Jones P A. Rapid quantitation of methylation differences at specific sites using methylation-sensitive single nucleotide primer extension (Ms-SNuPE). Nucleic Acids Res. 1997 Jun. 15; 25(12):2529-31, WO 95/00669) or by enzymatic digestion (Xiong Z, Laird P W. COBRA: a sensitive and quantitative DNA methylation assay. Nucleic Acids Res. 1997 Jun. 15; 25(12):2532-4). In addition, detection by hybridisation has also been described (Olek et al., WO 99/28498).

Further publications dealing with the use of the bisulfite technique for methylation detection in individual genes are: Grigg G, Clark S. Sequencing 5-methylcytosine residues in genomic DNA. Bioessays. 1994 June; 16(6):431-6, 431; Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method. Hum Mol Genet. 1997 March; 6(3):387-95; Feil R, Charlton J, Bird A P, Walter J, Reik W. Methylation analysis on individual chromosomes: improved protocol for bisulphite genomic sequencing. Nucleic Acids Res. 1994 Feb. 25; 22(4):695-6; Martin V, Ribieras S, Song-Wang X, Rio M C, Dante R. Genomic sequencing indicates a correlation between DNA hypomethylation in the 5' region of the pS2 gene and its expression in human breast cancer cell lines. Gene. 1995 May 19; 157(1-2):261-4; WO 97/46705, WO 95/15373, and WO 97/45560.

An overview of the Prior Art in oligomer array manufacturing can be gathered from a special edition of Nature Genetics (Nature Genetics Supplement, Volume 21, January 1999), published in January 1999, and from the literature cited therein.

Fluorescently labelled probes are often used for the scanning of immobilised DNA arrays. The simple attachment of Cy3 and Cy5 dyes to the 5'-OH of the specific probe are particularly suitable for fluorescence labels. The detection of the fluorescence of the hybridised probes may be carried out, for example via a confocal microscope. Cy3 and Cy5 dyes, besides many others, are commercially available.

Matrix Assisted Laser Desorption Ionisation Mass Spectrometry (MALDI-TOF) is a very efficient development for the analysis of biomolecules (Karas M, Hillenkamp F. Laser desorption ionisation of proteins with molecular masses exceeding 10,000 daltons. Anal Chem. 1988 Oct. 15; 60(20): 2299-301). An analyte is embedded in a light-absorbing matrix. The matrix is evaporated by a short laser pulse thus transporting the analyte molecule into the vapour phase in an unfragmented manner. The analyte is ionised by collisions with matrix molecules. An applied voltage accelerates the ions into a field-free flight tube. Due to their different masses, the ions are accelerated at different rates. Smaller ions reach the detector sooner than bigger ones.

MALDI-TOF spectrometry is excellently suited to the analysis of peptides and proteins. The analysis of nucleic acids is somewhat more difficult (Gut I G, Beck S. DNA and Matrix Assisted Laser Desorption Ionization Mass Spectrometry. Current Innovations and Future Trends. 1995, 1; 147-57). The sensitivity to nucleic acids is approximately 100 times worse than to peptides and decreases disproportionally with increasing fragment size. For nucleic acids having a multiply negatively charged backbone, the ionisation process via the matrix is considerably less efficient. In MALDI-TOF spectrometry, the selection of the matrix plays an eminently important role. For the desorption of peptides, several very efficient matrixes have been found which produce a very fine crystallisation. There are now several responsive matrixes for DNA, however, the difference in sensitivity has not been reduced. The difference in sensitivity can be reduced by chemically modifying the DNA in such a manner that it becomes more similar to a peptide. Phosphorothioate nucleic acids in which the usual phosphates of the backbone are substituted with thiophosphates can be converted into a charge-neutral DNA using simple alkylation chemistry (Gut I G, Beck S. A procedure for selective DNA alkylation and detection by mass spectrometry. Nucleic Acids Res. 1995 Apr. 25; 23(8): 1367-73). The coupling of a charge tag to this modified DNA results in an increase in sensitivity to the same level as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Fritsch and Maniatis eds., Molecular Cloning: A Laboratory Manual, 1989.

Breast cancer is currently the second most common type of cancer amongst women. In 2001 over 190,000 new cases of invasive breast cancer and over 47,000 additional cases of in situ breast cancer were diagnosed. Incidence and death rates increase with age, for the period 1994-1998 the incidence of breast cancer amongst women between the ages of 20 and 24 was only 1.5 per 100,000 population. However the risk increases to 489.7 within the age group 75-79. Mortality rates have decreased by approximately 5% over the last decade and factors affecting 5 year survival rates include age, stage of cancer, socioeconomic factors and race.

Breast cancer is defined as the uncontrolled proliferation of cells within breasts tissues. Breasts are comprised of 15 to 20 lobes joined together by ducts. Cancer arises most commonly in the duct, but is also found in the lobes with the rarest type of cancer termed inflammatory breast cancer.

It will be appreciated by those skilled in the art that there exists a continuing need to improve methods of early detection, classification and treatment of breast cancers. In contrast to the detection of some other common cancers such as cervical and dermal there are inherent difficulties in classifying and detecting breast cancers.

The first step of any treatment is the assessment of the patient's condition comparative to defined classifications of the disease. However the value of such a system is inherently dependant upon the quality of the classification. Breast cancers are staged according to their size, location and occurrence of metastasis. Methods of treatment include the use of surgery, radiation therapy, chemotherapy and endocrine therapy, which are also used as adjuvant therapies to surgery.

Endocrine therapies have been developed in order to block the effects of estrogen on cancer cells or to reduce serum estrogen levels. Tamoxifen (TAM) is the most widely used antioestrogenic drug for breast cancer patients. It acts blocking estrogen stimulation of breast cancer cells, inhibiting both translocation and nuclear binding of estrogen receptor. TAM is used in adjuvant setting for primary breast cancer patients and for the treatment of metastatic disease and its effectiveness has been proved in several clinical trials. Treatment for five years reduces annual disease recurrence by 47% and annual deaths by 26% and this reduction is similar in different age groups. Also it reduces the incidence of developing contralateral breast tumours. TAM is among the least toxic antineoplastic agents but as it has estrogenic properties in some tissues, it increases by 3 folds the risk of endometrial cancer. Other endocrine therapies include aromatase inhibitors, which block the enzyme aromatase in adipose tissue (the main source of estrogen in postmenopausal women) and lead to reduced or abolished production of estrogens in adipose tissue. Also, new agents which block or modulate the estrogen receptor have been developed, they are generally summarised as SERMs=selective estrogen receptor modulators. Yet another way to reduce the amount of estrogen available to the tumour is to apply agents which interrupt the feed-back loop in sex hormone regulation (LH-RH analogues) at a higher level.

In general, the side-effects of endocrine treatment are harmless compared to chemotherapy. However, as endocrine treatments eliminate or reduce estrogen as a growth factor for cancer, they work only for tumours which rely on estrogen as a growth factor. The growth of cancers which do not have a functional ER pathway cannot be modulated by endocrine therapies.

The current way to determine if a tumour will respond to endocrine therapies is the analysis of expression of hormone receptors. Hormone receptor status should be tested prior to any endocrine treatment as only a group of patients will benefit from therapy. For this purpose ER (estrogen receptor) and PR (progesterone receptor) status are tested routinely in all patients and they are considered predictive markers of response (a predictive marker or factor is any measurement associated with response or lack of response to a particular therapy). ER status is predictive of response in adjuvant endocrine therapy setting and also in advanced metastatic disease.

Currently, ER positive and or PR positive patients receive TAM and the remaining 10% of patients receive chemotherapy. The problem is that the endocrine treatment is only effective in a subgroup of hormone receptor positive patients and also, that a small subgroup of ER negative patients appear initially to respond to TAM. Then, the non responder subgroup will not only not benefit from endocrine treatment but have the adverse effects of it and will not have the opportunity to receive chemotherapy instead. On the other hand, the ER negative subgroup that could have benefit from endocrine treatment will receive instead chemotherapy. Several different assays are available to measure PR and ER, including biochemical and IHC (immunohistochemical) analysis, but there is a lack of standardisation of staining methods and interlaboratory variability (Clin Cancer Res 2000, 6:616-621).

Currently several predictive markers are under evaluation. As up to now most patients have received Tamoxifen as endocrine treatment most of the markers have been shown to be associated with response or resistance to tamoxifen. However, it is generally assumed that there is a large overlap between responders to one or the other endocrine treatment. In fact, ER and PR expression are used to select patients for any endocrine treatment. Among the markers which have been associated with TAM response is bcl-2. High bcl-2 levels showed promising correlation to TAM therapy response in patients with metastatic disease and prolonged survival and added valuable information to ER negative patient subgroup (J Clin Oncology 1997, 15 5:1916-1922; Endocrine, 2000, 13(1):1-10). There is conflicting evidence regarding the independent predictive value of c-erbB2 (Her2/neu) over expression in patients with advance breast cancer that require further evaluation and verification (British J of Cancer 1999, 79 (7/8):1220-1226; J Natl Cancer Inst, 1998, 90 (21): 1601-1608).

Other predictive markers include SRC-1 (steroid receptor coactivator-1), CGA gene over expression, cell kinetics and S phase fraction assays (Breast Cancer Res and Treat, 1998, 48:87-92; Oncogene 2001, 20:6955-6959). Recently, uPA (Urokinase-type plasminogen activator) and PAI-1 (Plasminogen activator inhibitor type 1) together showed to be useful to define a subgroup of patients who have worse prognosis and who would benefit from adjuvant systemic therapy (J Clinical Oncology, 2002, 20 n° 4). All of these markers need further evaluations in prospective trials as none of them is yet a validated marker of response.

A number of cancer-associated genes have been shown to be inactivated by hypermethylation of CpG islands during breast tumorigenesis. Decreased expression of the calcium binding protein S100A2 (Accession number NM_005978) has been associated with the development of breast cancers. Hypermethylation of the promoter region of this gene has been observed in neoplastic cells thus providing evidence that S100A2 repression in tumour cells is mediated by site-specific methylation.

The SYK gene (Accession number NM_003177) encodes a protein tyrosine kinase, Syk (spleen tyrosine kinase), that is highly expressed in hematopoietic cells. Syk is expressed in normal breast ductal epithelial cells but not in a subset of invasive breast carcinoma. Also, the loss of Syk expression seems to be associated with malignant phenotypes such as increased motility and invasion. The loss of expression occurs at the transcriptional level, and, as indicated by Yuan Y, Mendez R, Sahin A and Dai J L (Hypermethylation leads to silencing of the SYK gene in human breast cancer. Cancer Res. 2001 Jul. 15; 61(14):5558-61.), as a result of DNA hypermethylation.

The TGF-β type 2 receptor (encoded by the TGFBR2 gene, NM_003242) plays a role in trans-membrane signalling pathways via a complex of serine/threonine kinases. Mutations in the gene have been detected in some primary tumours and in several types of tumour-derived cell lines, including breast (Lucke C D, Philpott A, Metcalfe J C, Thompson A M, Hughes-Davies L, Kemp P R, Hesketh R. 'Inhibiting mutations in the transforming growth factor beta type 2 receptor in recurrent human breast cancer.' Cancer Res. 2001 Jan. 15; 61(2):482-5.).

The genes COX7A2L and GRIN2D were both identified as novel estrogen responsive elements by Watanabe et. al. (Isolation of estrogen-responsive genes with a CpG island library. Molec. Cell. Biol. 18: 442-449, 1998.) using the CpG-GBS (genomic binding site) method. The gene COX7A2L (Accession number NM_004718 encodes a, polypeptide 2-like cytochrome C oxidase subunit VIIA. Northern blot analysis detected an upregulation of COX7A2L after estrogen treatment of a breast cancer cell line. The gene GRIN2D (Accession number NM_000836) encodes the N-methyl-D-aspartate, ionotropic, subunit 2D glutamate receptor, a subunit of the NMDA receptor channels associated with neuronal signalling, furthermore expression of the cDNA has been observed in an osteosarcoma cell line. The gene VTN (also known as Vitronectin Accession number NM_000638) encodes a 75-kD glycoprotein (also called serum spreading factor or complement S-protein) that promotes attachment and spreading of animal cells in vitro, inhibits cytolysis by the complement C5b-9 complex, and modulates antithrombin III-thrombin action in blood coagulation. Furthermore expression of this gene has been linked to progression and invasiveness of cancer cells.

The gene SFN (also known as Stratifin) encodes a polypeptide of the 14-3-3 family, 14-3-3 sigma. The 14-3-3 family of proteins mediates signal transduction by binding to phosphoserine-containing proteins. Expression of the SFN gene is lost in breast carcinomas, this is likely due to hypermethylatin during the early stages of neoplastic transformation (see Umbricht C B, Evron E, Gabrielson E, Ferguson A, Marks J, Sukumar S. Hypermethylation of 14-3-3 sigma (stratifin) is an early event in breast cancer. Oncogene. 2001 Jun. 7; 20(26):3348-53).

The gene PSA (Accession number NM_021154), also known as PSA-T, is not to be confused with the gene also popularly referred to as PSA (Accession number NM_001648) which encodes prostate specific antigen and whose technically correct name is kallikrein 3. The gene PSA-T encodes the protein phosphoserine aminotransferase which is the second step-catalysing enzyme in the serine biosynthesis pathway. Changes in gene expression levels have been monitored by mRNA expression analysis and upregulation of the gene has been identified in colonic carcinoma in a study of 6 samples (Electrophoresis 2002 June; 23(11):1667-76 mRNA differential display of gene expression in colonic carcinoma. Ojala P, Sundstrom J, Gronroos J M, Virtanen E, Talvinen K, Nevalainen T J.).

The gene stathimin (NM_005563) codes for an oncoprotein 18, also known as stathimin, a conserved cytosolic phosphoprotein that regulates microtubule dynamics. The protein is highly expressed in a variety of human malignancies. In human breast cancers the stahimin gene has shown to be up-regulated in a subset of the tumours.

The gene PRKCD encodes a member of the family of protein kinase c enzymes, and is involved in B cell signaling and in the regulation of growth, apoptosis, and differentiation of a variety of cell types.

Some of these molecules interact in a cascade-like manner. PRKCD activity that targets STMN1 is modulated by SFN binding and SYK phosphorylation. Together this influences tubulin polymerization that is required for cell division.

The gene MSMB (Accession number NM_002443) has been mapped to 10q1.2. It encodes the beta-microseminoprotein (MSP) which is one of the major proteins secreted by the prostate. Furthermore, it may be useful as a diagnostic marker for prostate cancer. Using mRNA analysis low levels of beta-MSP mRNA expression and protein have been linked to progression under endocrine therapy and it has been postulated that it may be indicative of potentially aggressive prostate cancer (see Sakai H, Tsurusaki T, Kanda S, Koji T, Xuan J W, Saito Y. 'Prognostic significance of beta-microseminoprotein mRNA expression in prostate cancer.' Prostate. 1999 Mar. 1; 38(4):278-84.).

The gene TP53 (Accession number NM_000546) encodes the protein p53, one of the most well characterised tumour suppressor proteins. The p53 protein acts as a transcription factor and serves as a key regulator of the cell cycle. Inactivation of this gene through mutation disrupts the cell cycle, which, in turn, assists in tumour formation. Methylation changes associated with this gene have been reported to be significant in breast cancer. Saraswati et. al. (Nature 405, 974-978 (22 Jun. 2000) 'Compromised HOXA5 function can limit p53 expression in human breast tumours' reported that low levels of p53 mRNA in breast tumours was correlated to methylation of the HOXA5 gene. The product of the HOX5A gene binds to the promoter region of the p53 and mediates expression of the gene. Methylation of the promoter region of the p53 gene itself has been reported (Kang J H, Kim S J, Noh D Y, Park I A, Choe K J, Yoo O J, Kang H S. 'Methylation in the p53 promoter is a supplementary route to breast carcinogenesis: correlation between CpG methylation in the p53 promoter and the mutation of the p53 gene in the progression from ductal carcinoma in situ to invasive ductal carcinoma.' Lab Invest. 2001 April; 81(4):573-9.). It was therein demonstrated that CpG methylation in the p53 promoter region is found in breast cancer and it was hypothesised that methylation in the p53 promoter region could be an alternative pathway to neoplastic progression in breast tumours. It has been observed that treatment with Tamoxifen decreases the level of expression of the p53 gene (Farczadi E, Kaszas I, Baki M, Szende B. 'Changes in apoptosis, mitosis, Her2, p53 and Bcl2 expression in breast carcinomas after short-term tamoxifen treatment.' Neoplasma. 2002; 49(2):101-3.)

The gene CYP2D6 (Accession number: NM_000106) is a member of the human cytochrome P450 (CYP) superfamily. Many members of this family are involved in drug metabolism (see for example Curr Drug Metab. 2002 June; 3(3):289-309. Rodrigues A D, Rushmore T H.), of these Cytochrome P450 CYP2D6 is one of the most extensively characterised. It is highly polymorphic (more than 70 variations of the gene have been described), and allelic variation can result in both increased and decreased enzymatic activity. The CYP2D6 enzyme catalyses the metabolism of a large number of clinically important drugs including antidepressants, neuroleptics, some antiarrhythmics (Nature 1990 Oct. 25; 347(6295): 773-6 Identification of the primary gene defect at the cytochrome P450 CYP2D locus Gough A C, Miles J S, Spurr N K, Moss J E, Gaedigk A, Eichelbaum M, Wolf C R.).

The gene PTGS2 (Accession number NM_000963) encodes an inducible isozyme of prostaglandin-endoperoxide synthase (prostaglandin-endoperoxide synthase 2). Aberrant methylation of this gene has been identified in lung carcinoimas (Cancer Epidemiol Biomarkers Prev 2002 March; 11(3):291-7 Hierarchical clustering of lung cancer cell lines using DNA methylation markers. Virmani A K, Tsou J A, Siegmund K D, Shen L Y, Long T I, Laird P W, Gazdar A F, Laird-Offringa I A.).

The gene CGA (Accession number NM_000735) encodes the alpha polypetptide of glycoprotein hormones. Further, it has been identified as an estrogen receptor alpha (ER alpha)-responsive gene and overexpression of the gene has been linked to ER positivity in breast tumours. Bieche et. al. examined mRNA levels of said gene in 125 ER alpha-positive post-menopausal breast cancer patients treated with primary surgery followed by adjuvant tamoxifen therapy. Initial results indicated significant links between CGA gene overexpression and Scarff-Bloom-Richardson histopathological grade I+II and progesterone and estrogen receptor positivity, which suggested that CGA is a marker of low tumour aggressiveness ('Identification of CGA as a Novel Estrogen Receptor-responsive Gene in Breast Cancer: An Outstanding Candidate Marker to predict the Response to Endocrine TherapyCancer Research' 61, 1652-1658, Feb. 15, 2001. Ivan Bieche, Beatrice Parfait, Vivianne Le Doussal, Martine Olivi, Marie-Christine Rio, Rosette Lidereau and Michel Vidaud). Further mRNA expression analysis linked CGA expression levels to Tamoxifen response, it was postulated that when combined with analysis of the marker ERBB2 (a marker of poor response) the gene may be useful as a predictive marker of tamoxifen responsiveness in breast cancer (Oncogene 2001 Oct. 18; 20(47):6955-9 The CGA gene as new predictor of the response to endocrine therapy in ER alpha-positive postmenopausal breast cancer patients. Bieche I, Parfait B, Nogues C, Andrieu C, Vidaud D, Spyratos F, Lidereau R, Vidaud M.). The authors provided significant data associating the expression of the gene CGA with Tamoxifen treatment response. However, said analyses have all focused upon the analysis of relative levels of mRNA expression. This is not a methodology that is suitable for a medium or high throughput, nor is it a suitable basis for the development of a clinical assay.

The gene PITX-2 (NM_000325) encodes a transcription factor (PITX-2) which is known to be expressed during development of anterior structures such as the eye, teeth, and anterior pituitary. Although the expression of this gene is associated with cell differentiation and proliferation it has no heretofore recognised role in carcinogenesis or responsiveness to endocrine treatment. Furthermore, to date no known analysis of the methylation state of this gene has been reported.

RASSF1A (Ras association domain family 1A) gene is a candidate tumour suppressor gene at 3p21.3. The Ras GTPases are a superfamily of molecular switches that regulate cellular proliferation and apoptosis in response to extracellular signals. It is purported that RASSF1A is a tumour suppressor gene, and epigenetic alterations of this gene have been observed in a variety of cancers. Methylation of RASSF1A has been associated with poor prognosis in primary non-small cell lung cancer (Kim D H, Kim J S, Ji Y I, Shim Y M, Kim H, Han J, Park J., 'Hypermethylation of RASSF1A promoter is associated with the age at starting smoking and a poor prognosis in primary non-small cell lung cancer.' Cancer Res. 2003 Jul. 1; 63(13):3743-6.). It has also been associated with the development of pancreatic cancer (Kuzmin I, Liu L, Dammann R, Geil L, Stanbridge E J, Wilczynski S P, Lerman M I, Pfeifer G P. 'Inactivation of RAS association domain family 1A gene in cervical carcinomas and the role of human papillomavirus infection.' Cancer Res. 2003 Apr. 15; 63(8):1888-93.), as well as testicular tumours and prostate carcinoma amongst others. The application of the methylation of this gene as a cancer diagnostic marker has been described in U.S. Pat. No. 6,596,488, it does not however describe its application in the selection of appropriate treatments regimens for patients.

Also located within 3p21 is the Dystroglycan precursor gene (Dystrophin-associated glycoprotein 1) (NM_004393). Dystroglycan (DG, also known as DAG1) is an adhesion molecule comprising two subunits namely alpha-DG and beta-DG. The molecule is responsible for crucial interactions between extracellular matrix and cytoplasmatic compartment and it has been hypothesised that as such it may contribute to progression to metastatic disease. Decreased expression of this gene has been associated with correlated with higher tumour grade and stage in colon, prostate and breast tumours.

The onecut-2 transcription factor gene (NM__004852) is located at 18q21.31 is a homeodomain transcription factor regulator of liver gene expression in adults and during development.

The trefoil factor (TFF) 2 gene (NM__003225) is a member of the trefoil family of proteins. They are normally expressed at highest levels in the mucosa of the gastrointestinal tract, however they are often expressed ectopically in primary tumours of other tissues, including breast. The expression of TFF 1 is regulated by estrogen in estrogen-responsive breast cancer cells in culture, its expression is associated with that of the estrogen receptor and TFF1 is a marker of hormone responsiveness in tumours. TFF1 promoter methylation has been observed in non-expressing gastric carcinoma-derived cell lines and tissues.

TMEFF2 (NM__016192) encodes a transmembrane protein containing an epidermal growth factor (EGF)-like motif and two follistatin domains. It has been shown to be overexpressed in prostate and brain tissues and it has been suggested that this is an androgen-regulated gene exhibiting antiproliferative effects in prostate cancer cells.

Methylation of the gene ESR1 (NM__000125), encoding the estrogen receptor has been linked to several cancer types including lung, oesophageal, brain and colorectal. The estrogen receptor (ESR) is a ligand-activated transcription factor composed of several domains important for hormone binding, DNA binding, and activation of transcription.

The PCAF (NM__003884) gene encodes the p300/CBP-Associated Factor (PCAF). CBP and p300 are large nuclear proteins that bind to many sequence-specific factors involved in cell growth and/or differentiation. The p300/CBP associated factor displays in vivo binding activity with CBP and p300. The protein has histone acetyl transferase activity with core histones and nucleosome core particles, indicating that it plays a direct role in transcriptional regulation. p300/CBP associated factor also associates with NF-kappa-B p65. This protein has been shown to regulate expression of the gene p53 by acetylation of Lys320 in the C-terminal portion of p53.

The WBP11 (NM__016312) gene encodes a nuclear protein, which co-localises with mRNA splicing factors and intermediate filament-containing perinuclear networks. It contains two proline-rich regions that bind to the WW domain of Npw38, a nuclear protein, and thus this protein is also called Npw38-binding protein NpwBP.

DESCRIPTION

The present invention provides methods and nucleic acids for predicting the response of a patient with a cell proliferative disorder of the breast tissues to endocrine treatment. Using the methods and nucleic acids described herein, statistically significant models of patient responsiveness to said treatment regimen can be developed and utilised to assist patients and clinicians in determining treatment options. The described method is to be used to asses the suitability of endocrine treatment as a therapy for patients suffering from a cell proliferative disorder of the breast tissues. Thus, the present invention will be seen to reduce the problems associated with present treatment response prediction methods.

Using the methods and nucleic acids as described herein, patient responsiveness can be evaluated before or during endocrine treatment for a cell proliferative disorder of the breast tissues, in order to provide critical information to the patient and clinician as to the risks, burdens, and benefits associated endocrine treatment. It will be appreciated, therefore, that the methods and nucleic acids exemplified herein can serve to improve a patient's quality of life and odds of treatment success by allowing both patient and clinician a more accurate assessment of the patient's treatment options.

The aim of the invention is most preferably achieved by means of the analysis of the methylation patterns of one or a combination of genes taken from the group taken from the group xxSTMN1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF (see Table 1) and/or their regulatory regions. The invention is characterised in that the nucleic acid of one or a combination of genes taken from the group xxSTMN1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF are contacted with a reagent or series of reagents capable of distinguishing between methylated and non methylated CpG dinucleotides within the genomic sequence of interest.

The aim of the invention may also be achieved by the analysis of the CpG methylation of one or a plurality of any subset of the group of genes STMN1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF, in particular the following subsets are preferred:

TP53, PTGS2, FGFR1, PSA, CGA, CYP2D6 and MSMB
STMN1, PITX2, PSA and CGA
STMN1, SFN, S100A2, TGFBR2, SYK, GRIN2D, PSA, COX7A2L, VTN and PRKCD
ONECUT2, WBP11, CYP2D6, DAG1, ERBB2, S100A2, TFF1, TP53, TMEFF2, ESR, SYK, RASSF1, PITX2, PSAT1, CGA and PCAF The present invention makes available a method for ascertaining genetic and/or epigenetic parameters of genomic DNA. The method is for use in the improved treatment and monitoring of breast cell proliferative disorders, by enabling the accurate prediction of a patient's response to treatment with a therapy comprising one or more drugs which target the estrogen receptor pathway or are involved in estrogen metabolism, production, or secretion. In a particularly preferred embodiment, the method according to the invention enables the differentiation between patients who respond to said therapy and those who do not.

The method according to the invention may be used for the analysis of a wide variety of cell proliferative disorders of the breast tissues including, but not limited to, ductal carcinoma in situ, lobular carcinoma, colloid carcinoma, tubular carcinoma, medullary carcinoma, meta-plastic carcinoma, intraductal carcinoma in situ, lobular carcinoma in situ and papillary carcinoma in situ.

The method according to the invention is particularly suited to the prediction of response to the aforementioned therapy in two treatment settings. In one embodiment, the method is applied to patients who receive endocrine pathway targeting treatment as secondary treatment to an initial non chemotherapeutical therapy, e.g. surgery (hereinafter referred to as the adjuvant setting) as illustrated in FIG. 1. Such a treatment is often prescribed to patients suffering from Stage 1 to 3 breast carcinomas. In this embodiment responders are defined as those who do not have a detectable relapse of the breast cancer in a specified period of time, non responders are those who relapse within said time period.

In a further preferred embodiment said method is applied to patients suffering from a relapse of breast cancer following treatment by a primary means (preferably surgery) followed by a disease free period, and wherein the endocrine pathway targeting treatment has been prescribed in response to a detection of a relapse of the carcinoma. Such a treatment is often prescribed to patients suffering from later stage carcinomas, particularly wherein metastasis has occurred. Therefore this clinical setting shall also hereinafter be referred to as the 'metastatic setting'. In this embodiment responders are those who enter partial or complete remission i.e. subjects whose cancer recedes to undetectable levels as opposed to those whose diseases further metastasise or remain above detectable levels. This methodology present further improvements over the state of the art in that the method may be applied to any subject, independent of the estrogen and/or progesterone receptor status. Therefore in a preferred embodiment, the subject is not required to have been tested for estrogen or progesterone receptor status.

Furthermore, the method enables the analysis of cytosine methylations and single nucleotide polymorphisms within said genes.

The object of the invention is achieved by means of the analysis of the methylation patterns of one or more of the genes STMN1, SFN, S100A2, TGFBR2, TP53, PTGS2, FGFR1, SYK, P1TX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF and/or their regulatory regions. In a particularly preferred embodiment the sequences of said genes comprise SEQ ID NOs: 27, 40, 122, 43, 131, 50, 74, 127, 135, 86, 90, 128, 129, 99, 105, 115, 121, 126, 137, 129, 125, 132, 122, 123, 131, 133, 134, 127, 130, 135, 124, 128 and 136 and sequences complementary thereto.

The object of the invention may also be achieved by analysing the methylation patterns of one or more genes taken from the following subsets of said aforementioned group of genes. In one embodiment the object of the invention is achieved by analysis of the methylation patterns of one or more genes taken from the group consisting TP53, PTGS2, FGFR1, PSA, CGA, CYP2D6 and MSMB, and wherein it is further preferred that the sequence of said genes comprise SEQ ID NOs: 68, 50, 74, 90, 91, 92 and 99. In a further embodiment the object of the invention is achieved by analysis of the methylation patterns of one or more genes taken from the group consisting STMN1, PITX2, PSA and CGA, and wherein it is further preferred that the sequence of said genes comprise SEQ ID NOs: 27, 83, 90 and 91. The object of the invention may also be achieved by analysis of the methylation patterns of one or more genes taken from the group consisting of STMN1, SFN, S100A2, TGFBR2, SYK, GRIN2D, PSA, COX7A2L, VTN and PRKCD, and wherein it is further preferred that the sequence of said genes comprise SEQ ID NOs: 27, 40, 41, 43, 78, 86, 90, 105, 115, 121. It is also an embodiment of the invention that the object is achieved by analysis of the methylation patterns of one or more genes taken from the group consisting ONECUT2, WBP11, CYP2D6, DAG1, ERBB2, S100A2, TFF1, TP53, TMEFF2, ESR1, SYK, RASSF1, PITX2, PSAT1, CGA and PCAF, and wherein it is further preferred that the sequence of said genes comprise SEQ ID NOs: 126, 137, 129, 125, 132, 122, 123, 131, 133, 134, 127, 130, 135, 124, 128 and 136.

Wherein the patient receives the treatment as an adjuvant therapy it is preferred that said genes are selected from the group consisting of TP53, PTGS2, PITX2, CYP2D6, MSMB, WBP11, TMEFF2, ESR1, PITX2 and PCAF, and wherein it is further preferred that the sequence of said genes comprise SEQ ID NOs: 131, 50, 135, 129, 99, 137, 133, 134, 135 and 136.

Also preferred are the following subsets of this group of genes:

TP53, PTGS2, CYP2D6 and MSMB, wherein it is further preferred that the sequence of said genes comprise SEQ ID NOs: 68, 50, 92 and 99.

PITX2, wherein it is further preferred that the sequence of said gene comprises SEQ ID NO: 83.

WBP11, TMEFF2, ERBB2, ESR1, PITX2 and PCAF, wherein it is further preferred that the sequence of said genes comprise SEQ ID NOs: 137, 132, 133, 134, 135 and 136.

Wherein the patient receives the treatment in response in a metastatic setting it is preferred that said genes are selected from the group consisting of STMN1, SFN, S100A2, TGFBR2, FGFR1, SYK, GRIN2D, PSA, CGA, COX7A2L, VTN, PRKCD, ONECUT2, CYP2D6, DAG1, ERBB2, S100A2, TFF1, TP53, SYK, RASSF1, PSAT1 and CGA, and wherein it is further preferred that the sequence of said genes comprise SEQ ID NOs: 27, 40, 122, 43, 74, 127, 86, 90, 128, 105, 115, 121, 126, 129, 125, 132, 122, 123, 131, 127, 130, 124 and 128.

Also preferred are the following subsets of this group of genes:

FGFR1, PSA and CGA, wherein it is further preferred that the sequence of said genes comprise SEQ ID NOs: 74, 90 and 91.

STMN1, PSA and CGA, wherein it is further preferred that the sequence of said genes comprise SEQ ID NOs: 27, 90 and 91.

STMN1, SFN, S100A2, TGFBR2, SYK, GRIN2D, PSA, COX7A2L, VTN and PRKCD, wherein it is further preferred that the sequence of said genes comprise SEQ ID NOs: 27, 40, 41, 43, 78, 86, 90, 105, 115, 121.

ONECUT2, CYP2D6, DAG1, S100A2, TFF1, TP53, SYK, RASSF1, PSAT1 and CGA, wherein it is further preferred that the sequence of said genes comprise SEQ ID NOs: 126, 129, 125, 122, 123, 131, 127, 130, 124 and 128.

In a preferred embodiment said method is achieved by contacting said nucleic acid sequences in a biological sample obtained from a subject with at least one reagent or a series of reagents, wherein said reagent or series of reagents, distinguishes between methylated and non methylated CpG dinucleotides within the target nucleic acid.

In a preferred embodiment, the method comprises the following steps:

In the first step of the method the genomic DNA sample must be isolated from sources such as cells or cellular components which contain DNA, sources of DNA comprising, for example, cell lines, histological slides, biopsies, tissue embedded in paraffin, breast tissues, blood, plasma, lymphatic fluid, lymphatic tissue, duct cells, ductal lavage fluid, nipple aspiration fluid, bone marrow and combinations thereof. Extraction may be by means that are standard to one skilled in the art, these include the use of detergent lysates, sonification and vortexing with glass beads. Once the nucleic acids have been extracted the genomic double stranded DNA is used in the analysis.

In a preferred embodiment the DNA may be cleaved prior to the next step of the method, this may be by any means standard in the state of the art, in particular, but not limited to, with restriction endonucleases.

In the second step of the method, the genomic DNA sample is treated in such a manner that cytosine bases which are unmethylated at the 5'-position are converted to uracil, thymine, or another base which is dissimilar to cytosine in terms of hybridisation behaviour. This will be understood as 'pretreatment' hereinafter.

The above described treatment of genomic DNA is preferably carried out with bisulfite (sulfite, disulfite) and subsequent alkaline hydrolysis which results in a conversion of non-methylated cytosine nucleobases to uracil or to another base which is dissimilar to cytosine in terms of base pairing behaviour. If bisulfite solution is used for the reaction, then an addition takes place at the non-methylated cytosine bases. Moreover, a denaturating reagent or solvent as well as a radical interceptor must be present. A subsequent alkaline hydrolysis then gives rise to the conversion of non-methylated cytosine nucleobases to uracil. The converted DNA is then used for the detection of methylated cytosines.

Fragments of the pretreated DNA are amplified, using sets of primer oligonucleotides, and a preferably heat-stable, polymerase. Because of statistical and practical considerations, preferably more than six different fragments having a length of 100-2000 base pairs are amplified. The amplification of several DNA segments can be carried out simultaneously in one and the same reaction vessel. Usually, the amplification is carried out by means of a polymerase chain reaction (PCR).

The design of such primers is obvious to one skilled in the art. These should include at least two oligonucleotides whose sequences are each reverse complementary or identical to an at least 18 base-pair long segment of the following base sequences specified in the appendix: SEQ ID NO 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794. Said primer oligonucleotides are preferably characterised in that they do not contain any CpG dinucleotides. In a particularly preferred embodiment of the method, the sequence of said primer oligonucleotides are designed so as to selectively anneal to and amplify, only the breast cell specific DNA of interest, thereby minimising the amplification of background or non relevant DNA. In the context of the present invention, background DNA is taken to mean genomic DNA which does not have a relevant tissue specific methylation pattern, in this case, the relevant tissue being breast tissues.

According to the present invention, it is preferred that at least one primer oligonucleotide is bound to a solid phase during amplification. The different oligonucleotide and/or PNA-oligomer sequences can be arranged on a plane solid phase in the form of a rectangular or hexagonal lattice, the solid phase surface preferably being composed of silicon, glass, polystyrene, aluminium, steel, iron, copper, nickel, silver, or gold, it being possible for other materials such as nitrocellulose or plastics to be used as well.

The fragments obtained by means of the amplification may carry a directly or indirectly detectable label. Preferred are labels in the form of fluorescence labels, radionuclides, or detachable molecule fragments having a typical mass which can be detected in a mass spectrometer, it being preferred that the fragments that are produced have a single positive or negative net charge for better detectability in the mass spectrometer. The detection may be carried out and visualised by means of matrix assisted laser desorption/ionisation mass spectrometry (MALDI) or using electron spray mass spectrometry (ESI).

In the next step the nucleic acid amplificates are analysed in order to determine the methylation status of the genomic DNA prior to treatment.

The post treatment analysis of the nucleic acids may be carried out using alternative methods. Several methods for the methylation status specific analysis of the treated nucleic acids are described below, other alternative methods will be obvious to one skilled in the art.

The analysis may be carried out during the amplification step of the method. In one such embodiment, the methylation status of preselected CpG positions within the genes xxSTMN1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF and/or their regulatory regions may be detected by use of methylation specific primer oligonucleotides. The term "MSP" (Methylation-specific PCR) refers to the art-recognised methylation assay described by Herman et al. *Proc. Natl. Acad. Sci. USA* 93:9821-9826, 1996, and also disclosed in U.S. Pat. No. 5,786,146 and No. 6,265,171. The use of methylation status specific primers for the amplification of bisulphite treated DNA allows the differentiation between methylated and unmethylated nucleic acids. MSP primers pairs contain at least one primer which hybridises to a bisulphite treated CpG dinucleotide. Therefore the sequence of said primers comprises at least one CG, TG or CA dinucleotide. MSP primers specific for non methylated DNA contain a 'T' at the 3' position of the C position in the CpG. According to the present invention, it is therefore preferred that the base sequence of said primers is required to comprise a sequence having a length of at least 9 nucleotides which hybridises to a pretreated nucleic acid sequence according to SEQ ID NOs.: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794 and sequences complementary thereto wherein the base sequence of said oligomers comprises at least one CG, TG or CA dinucleotide.

In one embodiment of the method the methylation status of the CpG positions may be determined by means of hybridisation analysis. In this embodiment of the method the amplificates obtained in the second step of the method are hybridised to an array or a set of oligonucleotides and/or PNA probes. In this context, the hybridisation takes place in the manner described as follows. The set of probes used during the hybridisation is preferably composed of at least 4 oligonucleotides or PNA-oligomers. In the process, the amplificates serve as probes which hybridise to oligonucleotides previously bonded to a solid phase. The non-hybridised fragments are subsequently removed. Said oligonucleotides contain at least one base sequence having a length of 10 nucleotides which is reverse complementary or identical to a segment of the base sequences specified in the appendix, the segment containing at least one CpG or TpG dinucleotide. In a further preferred embodiment the cytosine of the CpG dinucleotide, or in the case of TpG, the thiamine, is the $5^{th}$ to $9^{th}$ nucleotide from the 5'-end of the 10-mer. One oligonucleotide exists for each CpG or TpG dinucleotide.

The non-hybridised amplificates are then removed. In the final step of the method, the hybridised amplificates are detected. In this context, it is preferred that labels attached to the amplificates are identifiable at each position of the solid phase at which an oligonucleotide sequence is located.

In a further embodiment of the method the methylation status of the CpG positions may be determined by means of oligonucleotide probes that are hybridised to the treated DNA concurrently with the PCR amplification primers (wherein said primers may either be methylation specific or standard).

A particularly preferred embodiment of this method is the use of fluorescence-based Real Time Quantitative PCR (Heid et al., Genome Res. 6:986-994, 1996) employing a dual-labelled fluorescent oligonucleotide probe (TaqMan™ PCR, using an ABI Prism 7700 Sequence Detection System, Perkin Elmer Applied Biosystems, Foster City, Calif.). The Taq-Man™ PCR reaction employs the use of a nonextendible interrogating oligonucleotide, called a TaqMan™ probe, which is designed to hybridise to a GpC-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulphite treatment it is required that the probe be methylation specific, as described in U.S. Pat. No. 6,331,393, (hereby incorporated by reference) also known as the Methyl Light assay. Variations on the TaqMan™ detection methodology that are also suitable for use with the described invention include the use of dual probe technology (Lightcycle™) or fluorescent amplification primers (Sunrise™ technology). Both these techniques may be adapted in a manner suitable for use with bisulphite treated DNA, and moreover for methylation analysis within CpG dinucleotides.

A further suitable method for the use of probe oligonucleotides for the assessment of methylation by analysis of bisulphite treated nucleic acids is the use of blocker oligonucleotides. The use of such oligonucleotides has been described in BioTechniques 23(4), 1997, 714-720 D. Yu, M. Mukai, Q. Liu, C. Steinman. Blocking probe oligonucleotides are hybridised to the bisulphite treated nucleic acid concurrently with the PCR primers. PCR amplification of the nucleic acid is terminated at the 5' position of the blocking probe, thereby amplification of a nucleic acid is suppressed wherein the complementary sequence to the blocking probe is present. The probes may be designed to hybridise to the bisulphite treated nucleic acid in a methylation status specific manner. For example, for detection of methylated nucleic acids within a population of unmethylated nucleic acids suppression of the amplification of nucleic acids which are unmethylated at the position in question would be carried out by the use of blocking probes comprising a 'CG' at the position in question, as opposed to a 'CA'.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivatised at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker-a process that normally results in degradation of the hybridised blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridises to a pretreated nucleic acid sequence according to one of SEQ ID NOs: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794 and sequences complementary thereto, wherein the base sequence of said oligonucleotides comprises at least one CpG, TpG or CpA dinucleotide.

In a further preferred embodiment of the method the determination of the methylation status of the CpG positions is carried out by the use of template directed oligonucleotide extension, such as MS SNuPE as described by Gonzalgo and Jones (Nucleic Acids Res. 25:2529-2531).

In a further embodiment of the method the determination of the methylation status of the CpG positions is enabled by sequencing and subsequent sequence analysis of the amplificate generated in the second step of the method (Sanger F., et al., 1977 PNAS USA 74: 5463-5467).

The method according to the invention may be enabled by any combination of the above means. In a particularly preferred mode of the invention the use of real time detection probes is concurrently combined with MSP and/or blocker oligonucleotides.

A further embodiment of the invention is a method for the analysis of the methylation status of genomic DNA without the need for pretreatment. In the first and second steps of the method the genomic DNA sample must be obtained and isolated from tissue or cellular sources. Such sources may include cell lines, histological slides, body fluids, or tissue embedded in paraffin. Extraction may be by means that are standard to one skilled in the art, these include the use of detergent lysates, sonification and vortexing with glass beads.

Once the nucleic acids have been extracted the genomic double stranded DNA is used in the analysis.

In a preferred embodiment the DNA may be cleaved prior to the treatment, this may be by any means standard in the state of the art, in particular with restriction endonucleases. In the third step, the DNA is then digested with one or more methylation sensitive restriction enzymes. The digestion is carried out such that hydrolysis of the DNA at the restriction site is informative of the methylation status of a specific CpG dinucleotide.

In a preferred embodiment the restriction fragments are amplified. In a further preferred embodiment this is carried out using the polymerase chain reaction.

In the final step the amplificates are detected. The detection may be by any means standard in the art, for example, but not limited to, gel electrophoresis analysis, hybridisation analysis, incorporation of detectable tags within the PCR products, DNA array analysis, MALDI or ESI analysis.

The aforementioned method is preferably used for ascertaining genetic and/or epigenetic parameters of genomic DNA.

In order to enable this method, the invention further provides the modified DNA of one or a combination of genes taken from the group STMN1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF as well as oligonucleotides and/or PNA-oligomers for detecting cytosine methylations within said genes. The present invention is based on the discovery that genetic and epigenetic parameters and, in particular, the cytosine methylation patterns of said genomic DNAs are particularly suitable for improved treatment and monitoring of breast cell proliferative disorders.

The nucleic acids according to the present invention can be used for the analysis of genetic and/or epigenetic parameters of genomic DNA.

This objective according to the present invention is achieved using a nucleic acid containing a sequence of at least 18 bases in length of the pretreated genomic DNA according to one of SEQ ID NOs: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794 and sequences complementary thereto.

The objective of the disclosed invention may also be achieved by using a nucleic acid containing a sequence of at least 18 bases in length of the pretreated genomic DNA according to one of SEQ ID NOs: 345, 346, 381, 382, 393, 394, 425, 426, 427, 428, 429, 430, 443, 444, 619, 620, 655, 656, 667, 668, 699, 700, 701, 702, 703, 704, 717 and 718 and sequences complementary thereto.

The objective of the disclosed invention may also be achieved by using a nucleic acid containing a sequence of at least 18 bases in length of the pretreated genomic DNA according to one of SEQ ID NOs: 299, 300, 411, 412, 425, 426, 427, 428, 573, 574, 685, 686, 699, 700, 701 and 702 and sequences complementary thereto.

The objective of the disclosed invention may also be achieved by using a nucleic acid containing a sequence of at least 18 bases in length of the pretreated genomic DNA according to one of SEQ ID NOs: 299, 300, 325, 326, 327, 328, 331, 332, 401, 402, 417, 418, 425, 426, 455, 456, 475, 476, 487, 488, 573, 574, 599, 600, 601, 602, 605, 606, 675, 676, 691, 692, 699, 700, 729, 730, 749, 750, 761, 762 and sequences complementary thereto.

The objective of the disclosed invention may also be achieved by using a nucleic acid containing a sequence of at least 18 bases in length of the pretreated genomic DNA according to one of SEQ ID NOs: 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794 and sequences complementary thereto.

The modified nucleic acids could heretofore not be connected with the ascertainment of disease relevant genetic and epigenetic parameters.

The object of the present invention is further achieved by an oligonucleotide or oligomer for the analysis of pretreated DNA, for detecting the genomic cytosine methylation state, said oligonucleotide containing at least one base sequence having a length of at least 10 nucleotides which hybridises to a pretreated genomic DNA according to SEQ ID NOs: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794. The oligomer probes according to the present invention constitute important and effective tools which, for the first time, make it possible to ascertain specific genetic and epigenetic parameters during the analysis of biological samples for features associated with a patient's response to endocrine treatment. Said oligonucleotides allow the improved treatment and monitoring of breast cell proliferative disorders. The base sequence of the oligomers preferably contains at least one CpG or TpG dinucleotide. The probes may also exist in the form of a PNA (peptide nucleic acid) which has particularly preferred pairing properties. Particularly preferred are oligonucleotides according to the present invention in which the cytosine of the CpG dinucleotide is within the middle third of said oligonucleotide e.g. the $5^{th}$-$9^{th}$ nucleotide from the 5'-end of a 13-mer oligonucleotide; or in the case of PNA-oligomers, it is preferred for the cytosine of the CpG dinucleotide to be the $4^{th}$-$6^{th}$ nucleotide from the 5'-end of the 9-mer.

The oligomers according to the present invention are normally used in so called "sets" which contain at least two oligomers and up to one oligomer for each of the CpG dinucleotides within SEQ ID NOs: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794.

In a particularly preferred embodiment of the method, the oligomers according to SEQ ID NOs: 1733-1736, 1967-1994, 2003-2024, 2031-2034, 2045-2134 are used for predicting a subject's response to endocrine treatment in an metastatic setting.

In a further embodiment of the method the oligomers according to SEQ ID NOs: 2011, 2012, 2017-2024 and 2031-2034 are used for predicting a subject's response to endocrine treatment in an metastatic setting.

In a further embodiment of the method the oligomers according to SEQ ID NOs: 2003-2024 are used for predicting a subject's response to endocrine treatment in an metastatic setting.

In a further embodiment of the method the oligomers according to SEQ ID NOs: 2003-2020 and 2045-2112 are used for predicting a subject's response to endocrine treatment in an meta-static setting.

In a further embodiment of the method the oligomers according to SEQ ID NOs: 1733-1736, 1967-1994, 2011-2025, 2045-2052, 2069-2078 and 2127-2134 are used for predicting a subject's response to endocrine treatment in an metastatic setting.

In a particularly preferred embodiment of the method the oligomers according to SEQ ID NOs: 1691-1692, 1925-1932, 1941-1954, 1965-1966, 1995-2002, 2025-2030, 2035-2044 and 2135-2142 are used for predicting a subject's response to endocrine treatment in an adjuvant setting.

In a further embodiment of the method the oligomers according to SEQ ID NOs: 2035-2044 are used for predicting a subject's response to endocrine treatment in an adjuvant setting.

In a further embodiment of the method the oligomers according to SEQ ID NOs: 2025-2030 are used for predicting a subject's response to endocrine treatment in an adjuvant setting.

In a further embodiment of the method the oligomers according to SEQ ID NOs: 1691-1692, 1925-1932, 1941-1954, 1965-1966, 1995-2002 and 2135-2142 are used for predicting a subject's response to endocrine treatment in an adjuvant setting.

In the case of the sets of oligonucleotides according to the present invention, it is preferred that at least one oligonucleotide is bound to a solid phase. It is further preferred that all the oligonucleotides of one set are bound to a solid phase.

The present invention further relates to a set of at least 2 n (oligonucleotides and/or PNA-oligomers) used for detecting the cytosine methylation state of genomic DNA, by analysis of said sequence or treated versions of said sequence (of the genes STMN1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF, as detailed in the sequence listing and Table 1) and sequences complementary thereto). These probes enable improved treatment and monitoring of breast cell proliferative disorders.

The set of oligomers may also be used for detecting single nucleotide polymorphisms (SNPs) by analysis of said sequence or treated versions of said sequence of the genes STMN 1, SFN, S100A2, TGFBR2, TP53, PTGS2, FGFR1, SYK, PITX2, GRIN2D, PSA, CGA, CYP2D6, MSMB, COX7A2L, VTN, PRKCD, ONECUT2, WBP11, CYP2D6, DAG1, ERBB2, S100A2, TFF1, TP53, TMEFF2, ESR1, SYK, RASSF1, PITX2, PSAT1, CGA and PCAF.

It will be obvious to one skilled in the art that the method according to the invention will be improved and supplemented by the incorporation of markers and clinical indicators known in the state of the art and currently used as predictive of the outcome of therapies which target endocrine or endocrine associated pathways. More preferably said markers include node status, age, menopausal status, grade, estrogen and progesterone receptors.

The genes that form the basis of the present invention may be used to form a "gene panel", i.e. a collection comprising the particular genetic sequences of the present invention and/or their respective informative methylation sites. The formation of gene panels allows for a quick and specific analysis of specific aspects of breast cancer treatment. The gene panel(s) as described and employed in this invention can be used with surprisingly high efficiency for the treatment of breast cell proliferative disorders by prediction of the outcome of treatment with a therapy comprising one or more drugs which target the estrogen receptor pathway or are involved in estrogen metabolism, production, or secretion. The analysis of each gene of the panel contributes to the evaluation of patient responsiveness, however, in a less preferred embodiment the patient evaluation may be achieved by analysis of only a single gene. The analysis of a single member of the 'gene panel' would enable a cheap but less accurate means of evaluating patient responsiveness, the analysis of multiple members of the panel would provide a rather more expensive means of carrying out the method, but with a higher accuracy (the technically preferred solution).

The efficiency of the method according to the invention is improved when applied to patients who have not been treated with chemotherapy. Accordingly, it is a particularly preferred embodiment of the method wherein the method is used for the assessment of subjects who have not undergone chemotherapy.

According to the present invention, it is preferred that an arrangement of different oligonucleotides and/or PNA-oligomers (a so-called "array") made available by the present invention is present in a manner that it is likewise bound to a solid phase. This array of different oligonucleotide- and/or PNA-oligomer sequences can be characterised in that it is arranged on the solid phase in the form of a rectangular or hexagonal lattice. The solid phase surface is preferably composed of silicon, glass, polystyrene, aluminium, steel, iron, copper, nickel, silver, or gold. However, nitrocellulose as well as plastics such as nylon which can exist in the form of pellets or also as resin matrices are suitable alternatives.

Therefore, a further subject matter of the present invention is a method for manufacturing an array fixed to a carrier material for the improved treatment and monitoring of breast cell proliferative disorders. In said method at least one oligomer according to the present invention is coupled to a solid phase. Methods for manufacturing such arrays are known, for example, from U.S. Pat. No. 5,744,305 by means of solid-phase chemistry and photolabile protecting groups.

A further subject matter of the present invention relates to a DNA chip for the improved treatment and monitoring of breast cell proliferative disorders. The DNA chip contains at least one nucleic acid according to the present invention. DNA chips are known, for example, in U.S. Pat. No. 5,837,832.

Moreover, a subject matter of the present invention is a kit which may be composed, for example, of a bisulfite-containing reagent, a set of primer oligonucleotides containing at least two oligonucleotides whose sequences in each case correspond to or are complementary to a 18 base long segment of the base sequences specified in SEQ ID NOs: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794 and/or PNA-oligomers as well as instructions for carrying out and evaluating the described method.

In a further preferred embodiment said kit may further comprise standard reagents for performing a CpG position specific methylation analysis wherein said analysis comprises one or more of the following techniques: MS-SNuPE, MSP, Methyl light, Heavy Methyl, and nucleic acid sequencing. However, a kit along the lines of the present invention can also contain only part of the aforementioned components.

Typical reagents (e.g., as might be found in a typical MethyLight® based kit) for MethyLight® analysis may include, but are not limited to: PCR primers for specific gene (or methylation-altered DNA sequence or CpG island); TaqMan® probes; optimised PCR buffers and deoxynucleotides; and Taq polymerase.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimised PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The oligomers according to the present invention or arrays thereof as well as a kit according to the present invention are intended to be used for the improved treatment and monitoring of breast cell proliferative disorders. According to the present invention, the method is preferably used for the analysis of important genetic and/or epigenetic parameters within genomic DNA, in particular for use in improved treatment and monitoring of breast cell proliferative disorders.

The methods according to the present invention are used, for improved treatment and monitoring of breast cell proliferative disorder by enabling more informed treatment regimens.

The present invention moreover relates to the diagnosis and/or prognosis of events which are disadvantageous or relevant to patients or individuals in which important genetic and/or epigenetic parameters within genomic DNA, said parameters obtained by means of the present invention may be compared to another set of genetic and/or epigenetic parameters, the differences serving as the basis for the diagnosis and/or prognosis of events which are disadvantageous or relevant to patients or individuals.

In the context of the present invention the term "hybridisation" is to be understood as a bond of an oligonucleotide to a completely complementary sequence along the lines of the Watson-Crick base pairings in the sample DNA, forming a duplex structure.

In the context of the present invention, "genetic parameters" are mutations and polymorphisms of genomic DNA and sequences further required for their regulation. To be designated as mutations are, in particular, insertions, deletions, point mutations, inversions and polymorphisms and, particularly preferred, SNPs (single nucleotide polymorphisms).

In the context of the present invention the term "methylation state" is taken to mean the degree of methylation present in a nucleic acid of interest, this may be expressed in absolute or relative terms i.e. as a percentage or other numerical value or by comparison to another tissue and therein described as hypermethylated, hypomethylated or as having significantly similar or identical methylation status.

In the context of the present invention the term "regulatory region" of a gene is taken to mean nucleotide sequences which affect the expression of a gene. Said regulatory regions may be located within, proximal or distal to said gene. Said regulatory regions include but are not limited to constitutive promoters, tissue-specific promoters, developmental-specific promoters, inducible promoters and the like. Promoter regulatory elements may also include certain enhancer sequence elements that control transcriptional or translational efficiency of the gene.

In the context of the present invention the term "chemotherapy" is taken to mean the use of drugs or chemical substances to treat cancer. This definition excludes radiation therapy (treatment with high energy rays or particles), hormone therapy (treatment with hormones or hormone analogues (synthetic substitutes) and surgical treatment.

In the context of the present invention, "epigenetic parameters" are, in particular, cytosine methylations and further modifications of DNA bases of genomic DNA and sequences further required for their regulation. Further epigenetic parameters include, for example, the acetylation of histones which, cannot be directly analysed using the described method but which, in turn, correlates with the DNA methylation.

In the context of the present invention the term "adjuvant treatment" is taken to mean a therapy of a cancer patient immediately following an initial non chemotherapeutical therapy, e.g. surgery. In general, the purpose of an adjuvant therapy is to provide a significantly smaller risk of recurrences compared without the adjuvant therapy.

In the context of the present invention the term "estrogen and/or progesterone receptor positive" is taken to mean cells that express on their surface receptors that are susceptible to the binding of estrogens and/or progesterones.

BRIEF DESCRIPTION OF THE DRAWINGS

In the following, the present invention will be explained in greater detail on the basis of the sequences, figures and examples without being limited thereto.

FIGS. 5 to 12 show a ranked matrix of additional data obtained according to Example 1 (Dataset 1) according to CpG methylation differences between the two classes of tissues, using an algorithm. FIGS. 5, 7, 9 and 11 are shown in greyscale, wherein the most significant CpG positions are at the bottom of the matrix with significance decreasing towards the top. Black indicates total methylation at a given CpG position, white represents no methylation at the particular position, with degrees of methylation represented in grey, from light (low proportion of methylation) to dark (high proportion of methylation). Each row represents one specific CpG position within a gene and each column shows the methylation profile for the different CpGs for one sample. On the left side the gene name is shown, on the right side p values for the individual CpG positions are shown. The p values are the probabilities that the observed distribution occurred by chance in the data set. FIGS. 6, 8, 10 and 12 are true black and white copies of the original red-green versions of the preceding figures (i.e. FIGS. 5, 7, 9 and 11 respectively).

Figure 1:
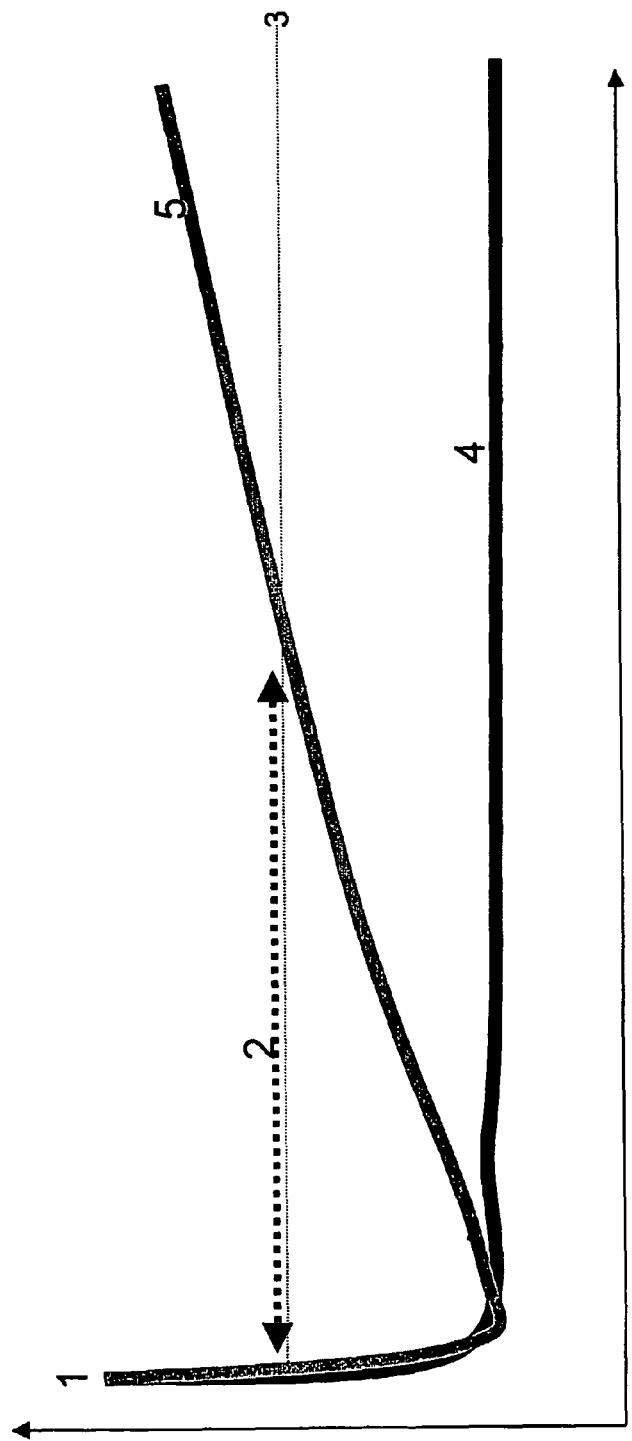
FIG. 1 shows a preferred application of the method according to the invention. The X axis shows the tumour(s) mass, wherein the line '3' shows the limit of detectability. The Y-axis shows time. Accordingly said figure illustrates a simplified model of endocrine treatment of an Stage 1-3 breast tumour wherein primary treatment was surgery (at point 1), followed by adjuvant therapy with Tamoxifen. In a first scenario a responder to treatment (4) is shown as remaining below the limit of detectability for the duration of the observation. A non responder to the treatment (5) has a period of disease free survival (2) followed by relapse when the carcinoma mass reaches the level of detectability.

SEQ ID NOS: 27, 40, 122, 43, 131, 50, 74, 127, 135, 86, 90, 128, 129, 99, 105, 115, 121, 126, 137, 129, 125, 132, 122, 123, 131, 133, 134, 127, 130, 135, 124, 128 and 136 represent 5' and/or regulatory regions and/or CpG rich regions of the genes according to Table 1. These sequences are derived from Genbank and will be taken to include all minor variations of the sequence material which are currently unforeseen, for example, but not limited to, minor deletions and SNPs.

SEQ ID NOS: 299, 300, 325, 326, 327, 328, 331, 332, 345, 346, 381, 382, 393, 394, 401, 402, 411, 412, 417, 418, 425, 426, 427, 428, 429, 430, 443, 444, 455, 456, 475, 476, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 573, 574, 599, 600, 601, 602, 605, 606, 619, 620, 655, 656, 667, 668, 675, 676, 685, 686, 691, 692, 699, 700, 701, 702, 703, 704, 717, 718, 729, 730, 749, 750, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793 and 794 exhibit the pretreated sequence of DNA derived from the genomic sequence according to Table 1. These sequences will be taken to include all minor variations of the sequence material which are currently unforeseen, for example, but not limited to, minor deletions and SNPs.

SEQ ID NO: 2003, 2003, 2003, 2003, 2004, 2004, 2004, 2004, 2005, 2005, 2005, 2005, 2006, 2006, 2006, 2006, 2007, 2007, 2007, 2007, 2008, 2008, 2008, 2008, 2009, 2009, 2009, 2009, 2010, 2010, 2010, 2010, 2011, 2011, 2011, 2012, 2012, 2012, 2013, 2013, 2014, 2014, 2015, 2015, 2016, 2016, 2017, 2017, 2017, 2018, 2018, 2018, 2019, 2019, 2019, 2020, 2020, 2020, 2021, 2021, 2022, 2022, 2023, 2023, 2024, 2024, 2025, 2025, 2026, 2026, 2027, 2027, 2028, 2028, 2029, 2029, 2030, 2030-2035, 2035, 2036, 2036, 2037, 2037, 2038, 2038-2045, 2045, 2046, 2046, 2047, 2047, 2048, 2048, 2049, 2049, 2050, 2050, 2051, 2051, 2052, 2052, 2053, 2053, 2054, 2054, 2055, 2055, 2056, 2056, 2057, 2057, 2058, 2058, 2059, 2059, 2060, 2060-2073, 2073, 2074, 2074-2077, 2077, 2078, 2078-2081, 2081, 2082, 2082-2095, 2095, 2096, 2096, 2097, 2097, 2098, 2098, 2099, 2099, 2100, 2100, 2101, 2101, 2102, 2102, 2103, 2103, 2104, 2104-2109, 2109, 2110, 2110, 2111, 2111, 2112, 2112, 2113, 2113, 2114, 2114-2123, 2123, 2124, 2124, 2125, 2125, 2126 and 2126-2142 exhibit the sequence of oligomers which are useful for the analysis of CpG positions within genomic DNA according to SEQ ID NO: 1 to SEQ ID NO: 63 according to Tables 2 and 3.

SEQ ID NO 2001 to SEQ ID NO 2140 exhibit the sequence of oligomers which are particularly useful for the analysis of the methylation status of CpG positions of genomic DNA according to SEQ ID NOS: 27, 40, 122, 43, 131, 50, 74, 127, 135, 86, 90, 128, 129, 99, 105, 115, 121, 126, 137, 129, 125, 132, 122, 123, 131, 133, 134, 127, 130, 135, 124, 128 and 136.

SEQ ID NO: 54, SEQ ID NO: 56 and SEQ ID NO: 133 represent genomic sequences of gene TMEFF2 and SEQ ID NOs: 349, 350, 353, 354, 511, 623, 624, 627, 628, 785 and 786 represent the pretreated sequence thereof.

SEQ ID NOs: 56, 70 and 136 represent genomic sequences of gene ESR1 and SEQ ID Nos:357, 358, 385, 386, 515, 514, 631, 632, 659, 660, 787 and 788 represent the pretreated sequence thereof.

SEQ ID NO: 135 and SEQ ID NO: 83 represent the genomic sequence of gene PITX2 and SEQ ID NOs: 411, 412, 515, 516, 685, 686, 789 and 790 represent the pretreated sequence thereof.

SEQ ID NO: 119 and SEQ ID NO: 136 represent genomic sequences of gene PCAF and SEQ ID Nos:483, 484, 517, 518, 757, 758, 791, 792 represent the pretreated sequence thereof.

SEQ ID NO: 137 represents the genomic sequence of gene WBP11 and SEQ ID NOs: 519, 520, 793 and 794 represent the pretreated sequence thereof.

SEQ ID NO:27 represents the genomic sequence of gene STMN1 and SEQ ID NOs: 299, 300, 573 and 574 represent the pretreated sequence thereof.

SEQ ID NO: 90 and SEQ ID NO: 124 represent genomic sequence of gene PSA also known as PSAT1 and SEQ ID NOs: 425, 426, 699, 700, 493, 494, 767 and 768 represent the pre-treated sequence thereof.

SEQ ID NO: 91 and SEQ ID NO: 128 represent genomic sequence of gene CGA and SEQ ID NOs: 427, 428, 501, 502, 701, 702, 775 and 776 represent the pretreated sequence thereof.

SEQ ID NO: 74 represents the genomic sequence of gene FGFR1 and SEQ ID NOs: 393, 394, 667 and 668 represent the pretreated sequence thereof.

SEQ ID NO:50 represents the genomic sequence of gene PTGS2 and SEQ ID NOs: 345, 346, 619 and 620 represent the pretreated sequence thereof.

SEQ ID NO: 90 represents the genomic sequence of gene MSMB and SEQ ID NOs: 443, 444, 717 and 718 represent the pretreated sequence thereof.

SEQ ID NO: 68 and SEQ ID NO: 131 represent genomic sequence of gene TP53 and SEQ ID NOs: 381, 382, 507, 508, 655, 656, 781 and 782 represent the pretreated sequence thereof.

SEQ ID NO: 92 represents the genomic sequence of gene CYP2D6 and SEQ ID NOs: 429, 430, 703 and 704 represent the pretreated sequence thereof.

SEQ ID NO: 41 and SEQ ID NO: 122 represent genomic sequence of gene S100A2 and SEQ ID NOs: 327, 328, 489, 490. 601, 601, 763 and 764 represent the pretreated sequence thereof.

SEQ ID NO: 121 represents the genomic sequence of gene PRKCD and SEQ ID NOs: 487, 488, 761 and 762 represent the pretreated sequence thereof.

SEQ ID NO: 78 and SEQ ID NO: 127 represents the genomic sequence of gene SYK and SEQ ID NOs: 401, 402, 499, 500, 675, 676, 773 and 774 represent the pretreated sequence thereof.

SEQ ID NO: 115 represents the genomic sequence of gene VTN and SEQ ID NOs: 475, 476, 749, 750 represent the pretreated sequence thereof.

SEQ ID NO: 86 represents the genomic sequence of gene GRIN2D and SEQ ID NOs: 417, 418, 691 and 692 represent the pretreated sequence thereof.

SEQ ID NO: 43 represents the genomic sequence of gene TGFBR2 and SEQ ID NOs: 331, 332, 605 and 606 represent the pretreated sequence thereof.

SEQ ID NO: 105 represents the genomic sequence of gene COX7A2L and SEQ ID NOs: 455, 456, 729 and 730 represent the pretreated sequence thereof.

SEQ ID NO: 42 and SEQ ID NO: 123 represent genomic sequence of gene TFF1 and SEQ ID NOs: 329, 330, 491, 492, 603, 604, 765 and 766 represent the pretreated sequence thereof.

SEQ ID NO: 125 represents the genomic sequence of gene DAG1 and SEQ ID NOs: 495, 496, 769 and 770 represent the pretreated sequence thereof.

SEQ ID NO: 126 represents the genomic sequence of gene onecut and SEQ ID NOs: 497, 498, 771 and 772 represent the pretreated sequence thereof.

SEQ ID NO: 129 represents the genomic sequence of gene CYP2D6 and SEQ ID NOs: 503, 504, 777 and 778 represent the pretreated sequence thereof.

SEQ ID NO: 59 and SEQ ID NO: 130 represent genomic sequence of gene RASSF1 and SEQ ID Nos:363, 364, 505, 506, 637, 638, 779, 780 represent the pretreated sequence thereof.

SEQ ID NO: 132 represents the genomic sequence of gene ERBB2 and SEQ ID NOs: 509, 510, 783 and 784 represent the pretreated sequence thereof.

EXAMPLE 1

DNA samples were extracted using the Wizzard Kit (Promega), samples from 200 patients were analysed, four data analyses were carried out on a selection of candidate markers.

Bisulfite Treatment and mPCR

Total genomic DNA of all samples was bisulfite treated converting unmethylated cytosines to uracil. Methylated cytosines remained conserved. Bisulfite treatment was performed with minor modifications according to the protocol described in Olek et al. (1996). After bisulfitation 10 ng of each DNA sample was used in subsequent mPCR reactions containing 6-8 primer pairs.

Each reaction contained the following:

400 µM dNTPs 2 pmol each primer

1 U Hot Star Taq (Qiagen)

10 ng DNA (bisulfite treated)

Further details of the primers are shown in TABLE 1.

Forty cycles were carried out as follows: Denaturation at 95° C. for 15 min, followed by annealing at 55° C. for 45 sec., primer elongation at 65° C. for 2 min. A final elongation at 65° C. was carried out for 10 min.

Hybridisation

All PCR products from each individual sample were then hybridised to glass slides carrying a pair of immobilised oligonucleotides for each CpG position under analysis. Each of these detection oligonucleotides was designed to hybridise to the bisulphite converted sequence around one CpG site which was either originally unmethylated (TG) or methylated (CG). See Table 2 for further details of hybridisation oligonucleotides used. Hybridisation conditions were selected to allow the detection of the single nucleotide differences between the TG and CG variants.

5 µl volume of each multiplex PCR product was diluted in 10×Ssarc buffer (10×Ssarc:230 ml 20×SSC, 180 ml sodium lauroyl sarcosinate solution 20%, dilute to 1000 ml with dH2O). The reaction mixture was then hybridised to the detection oligonucleotides as follows. Denaturation at 95° C., cooling down to 10° C., hybridisation at 42° C. overnight followed by washing with 10×Ssarc and dH2O at 42° C. Further details of the hybridisation oligonucleotides are shown in TABLE 2.

Fluorescent signals from each hybridised oligonucleotide were detected using genepix scanner and software. Ratios for the two signals (from the CG oligonucleotide and the TG oligonucleotide used to analyse each CpG position) were calculated based on comparison of intensity of the fluorescent signals.

Data Analysis Methods

Analysis of the chip data: From raw hybridisation intensities to methylation ratios; The log methylation ratio (log(CG/TG)) at each CpG position is determined according to a standardised preprocessing pipeline that includes the following steps: For each spot the median background pixel intensity is subtracted from the median foreground pixel intensity (this gives a good estimate of background corrected hybridisation intensities): For both CG and TG detection oligonucleotides of each CpG position the background corrected median of the 4 redundant spot intensities is taken; For each chip and each CpG position the log(CG/TG) ratio is calculated; For each sample the median of log(CG/TG) intensities over the redundant chip repetitions is taken. This ratio has the property that the hybridisation noise has approximately constant variance over the full range of possible methylation rates (Huber et al., 2002).

Principle Component Analysis

The principle component analysis (PCA) projects measurement vectors (e.g. chip data, methylation profiles on several CpGs etc.) onto a new coordinate system. The new coordinate axes are referred to as principal components. The first principal component spans the direction of the largest variance of the data. Subsequent components are ordered by decreasing variance and are orthogonal to each other. Different CpG positions contribute with different weights to the extension of the data cloud along different components. PCA is an unsupervised technique, i.e., it does not take into account the labels of the data points (for further details see e.g. Ripley (1996)).

PCA is typically used to project high dimensional data (in our case methylation-array data) onto lower dimensional subspaces in order to visualise or extract features with high variance from the data. In the present report we use 2 dimensional projections for statistical quality control of the data. We investigate the effect of different process parameters on the chip data and exclude that changing process parameters cause large alterations in the measurement values.

A robust version of PCA is used to detect single outlier chips and exclude them from further analysis (Model et al., 2002).

Hypothesis Testing

The main task is to identify markers that show significant differences in the average degree of methylation between two classes. A significant difference is detected when the nullhypothesis that the average methylation of the two classes is identical can be rejected with $p<0.05$. Because we apply this test to a whole set of potential markers we have to correct the p-values for multiple testing: This was done by applying the False Discovery Rate (FDR) method (Dudoit et al., 2002).

For testing the null hypothesis that the methylation levels in the two classes are identical we used the likelihood ratio test for logistic regression models (Venables and Ripley, 2002). The logistic regression model for a single marker is a linear combination of methylation measurements from all CpG positions in the respective genomic region of interest (ROI). A significant p-value for a marker means that this ROI has some systematic correlation to the question of interest as given by the two classes. However, at least formally it makes no statement about the actual predictive power of the marker.

Class Prediction by Supervised Learning

In order to give a reliable estimate of how well the CpG ensemble of a selected marker can differentiate between different tissue classes we can determine its prediction accuracy by classification. For that purpose we calculate a methylation profile based prediction function using a certain set of tissue samples with their class label. This step is called training and it exploits the prior knowledge represented by the data labels. The prediction accuracy of that function is then tested by cross-validation or on a set of independent samples. As a method of choice, we use the support vector machine (SVM) algorithm (Duda (2001), Christiannini (2000)) to learn the prediction function. If not stated otherwise, for this report the risk associated with false positive or false negative classifications are set to be equal relative to the respective class sizes. It follows that the learning algorithm obtains a class prediction function with the objective to optimise accuracy on an independent test sample set. Therefore sensitivity and specificity of the resulting classifier can be expected to be approximately equal.

Data Analysis

Data sets 1 and 2 (FIGS. 5 to 13)

The data is then sorted into a ranked matrix according to CpG methylation differences between the two classes of tissues, using an algorithm. FIGS. 5, 7, 9 and 11 to 13 are shown in greyscale, wherein the most significant CpG positions are at the bottom of the matrix with significance decreasing towards the top. Black indicates total methylation at a given CpG position, white represents no methylation at the particular position, with degrees of methylation represented in grey, from light (low proportion of methylation) to dark (high proportion of methylation). Each row represents one specific CpG position within a gene and each column shows the methylation profile for the different CpGs for one sample. On the left side a CpG and gene identifier is shown this may be cross referenced with the accompanying table (Table 5) in order to ascertain the gene in question and the detection oligomer used. On the right side p values for the individual CpG positions are shown. The p values are the probabilities that the observed distribution occurred by chance in the data set. FIGS. 6, 8, 10 and 12 are the original red-green versions of the preceding figures (i.e. FIGS. 5, 7, 9 and 11 respectively). Dark grey indicates total methylation at a given CpG position, light grey represents no methylation at the particular position.

Data Set 1: Adjuvant Setting

Analysis of the methylation patterns of patient samples treated with Tamoxifen as an adjuvant therapy immediately following surgery (see FIG. 1) is shown in the matrices according to FIGS. 5 to 8. In this analysis it can be seen that the genes PTGS2, MSMB, TP53 and CYP2D6 were significantly differentially methylated between the two classes of tissues (responders to therapy and non responders to therapy).

Figure 3:
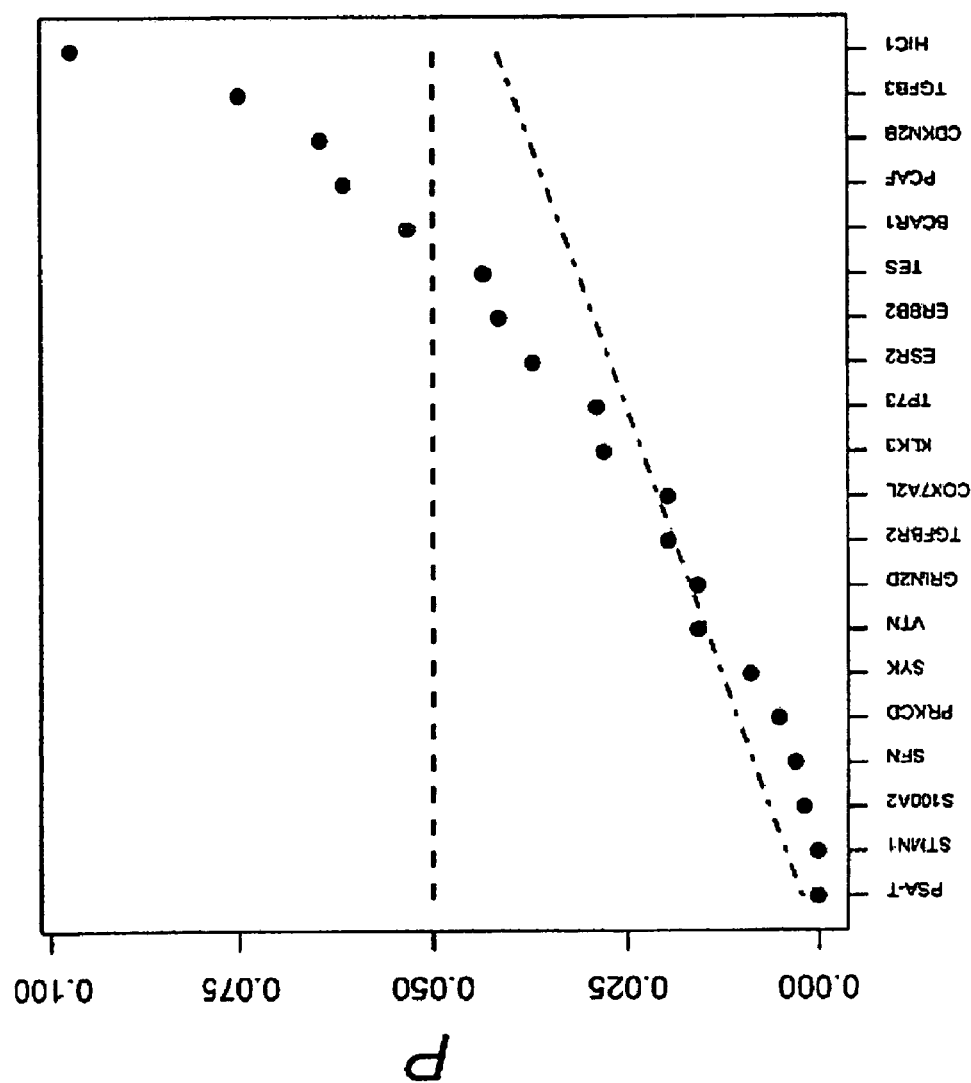
FIG. 3 shows the methylation analysis of CpG islands according to Example 1. CpG islands per gene were grouped and their correlation with objective response determined by Hotelling's $T^2$ statistics. Black dots indicate the P-value of the indicated gene. The 20 most informative genes, ranked from left to right with increasing P-value, are shown. The top dotted line marks the uncorrected significance value (P<0.05). The lower dotted line marks significance after false discovery rate correction of 25%. All genes with a P-value smaller or equal to the gene with the largest P-value that is below the lower line (in this case COX7A2L) are considered significant. The FDR correction chosen guarantees that the identified genes are with 75% chance true discoveries.
Figure 4:
FIG. 4 shows the raw CpG dinucleotide methylation data of the 10 genes that significantly correlated with the overall response rate as determined in FIG. 3 (Example 1). Tumours from objective responders (CR+PR) are show on the left; tumours from patients with progressive disease (PD) are shown on the right. The shades of grey represents the relative distance of the CpG dinucleotide methylation status from the mean value. CpG dinucleotides are grouped per gene. The indicated genes are ordered from top to bottom with increasing significance. Light grey represents a hypomethylated CpG dinucleotide while darker grey indicates a hypermethylated CpG dinucleotide. Methylation data are centred and normalised to one standard deviation for every individual CpG dinucleotide.
Figure 5:
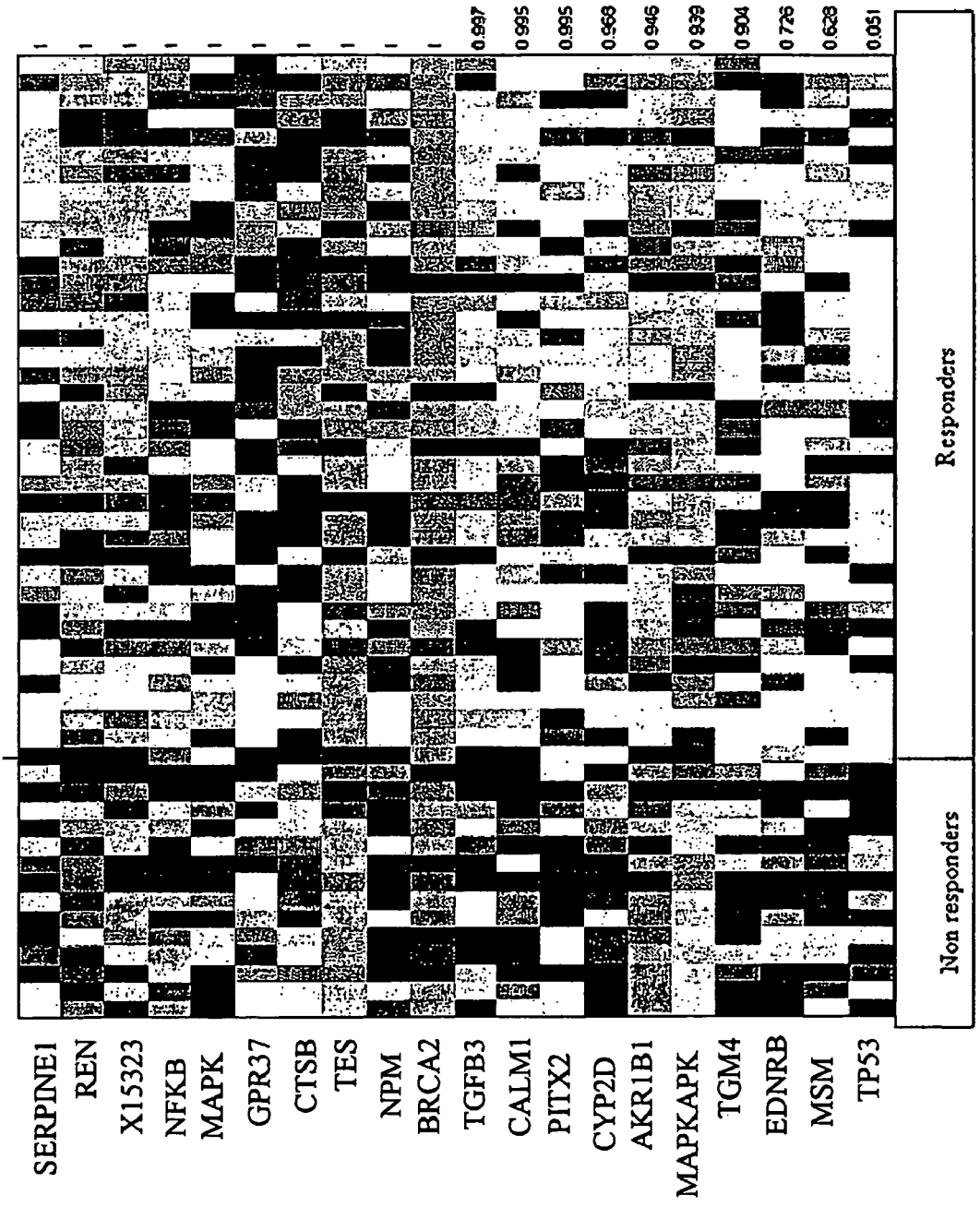
Figure 6:
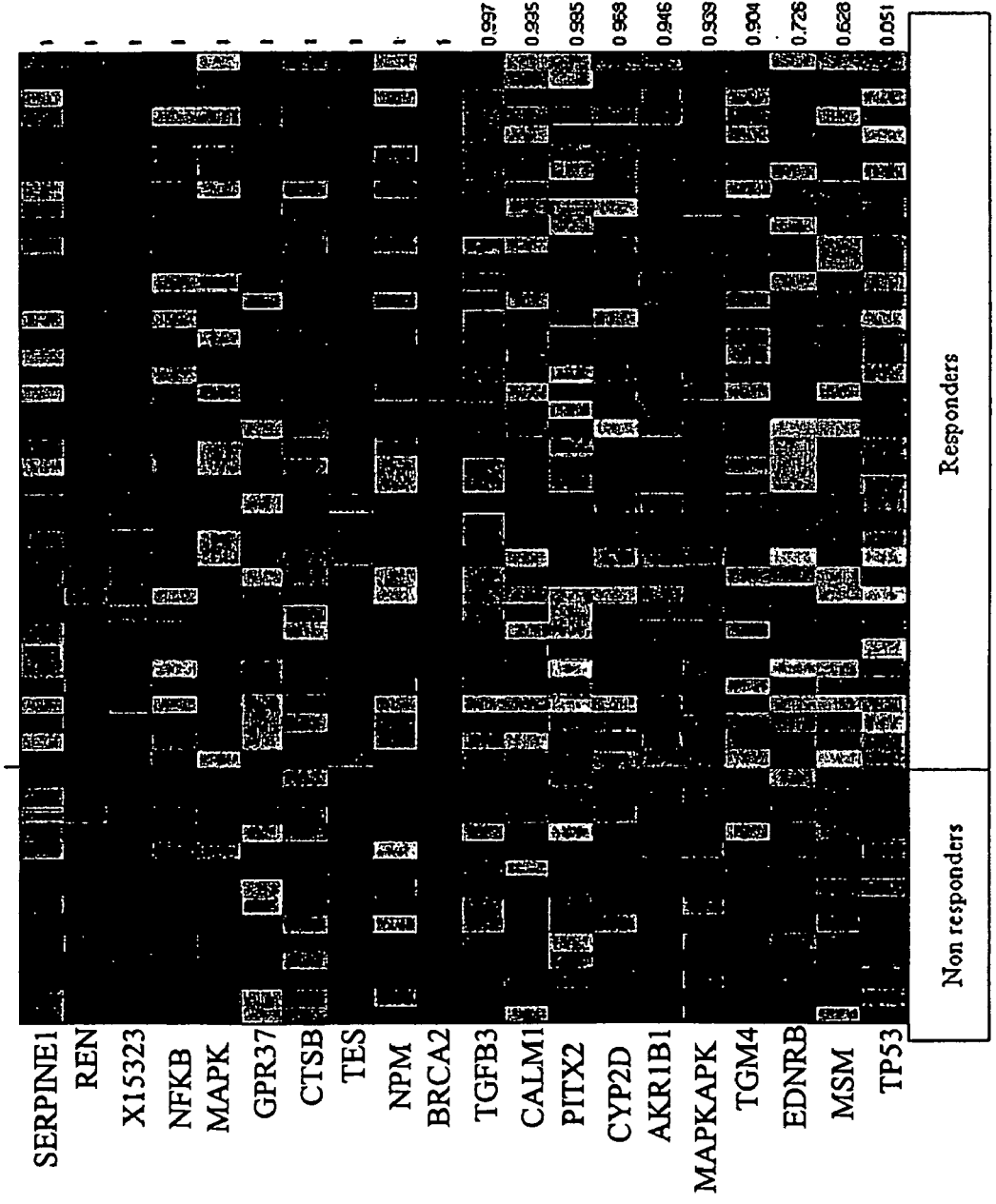

In the classification shown in FIGS. 3 and 4 the genes TP53 and MSMB were significantly more methylated in non-responders to the drug Tamoxifen, wherein subjects with a disease free survival of less than 36 months were classified as non responders and subjects with a disease free survival of greater than 60 months were classified as responders. This classification was carried out with a sensitivity of 0.84 and a sensitivity of 0.16.

Figure 7:
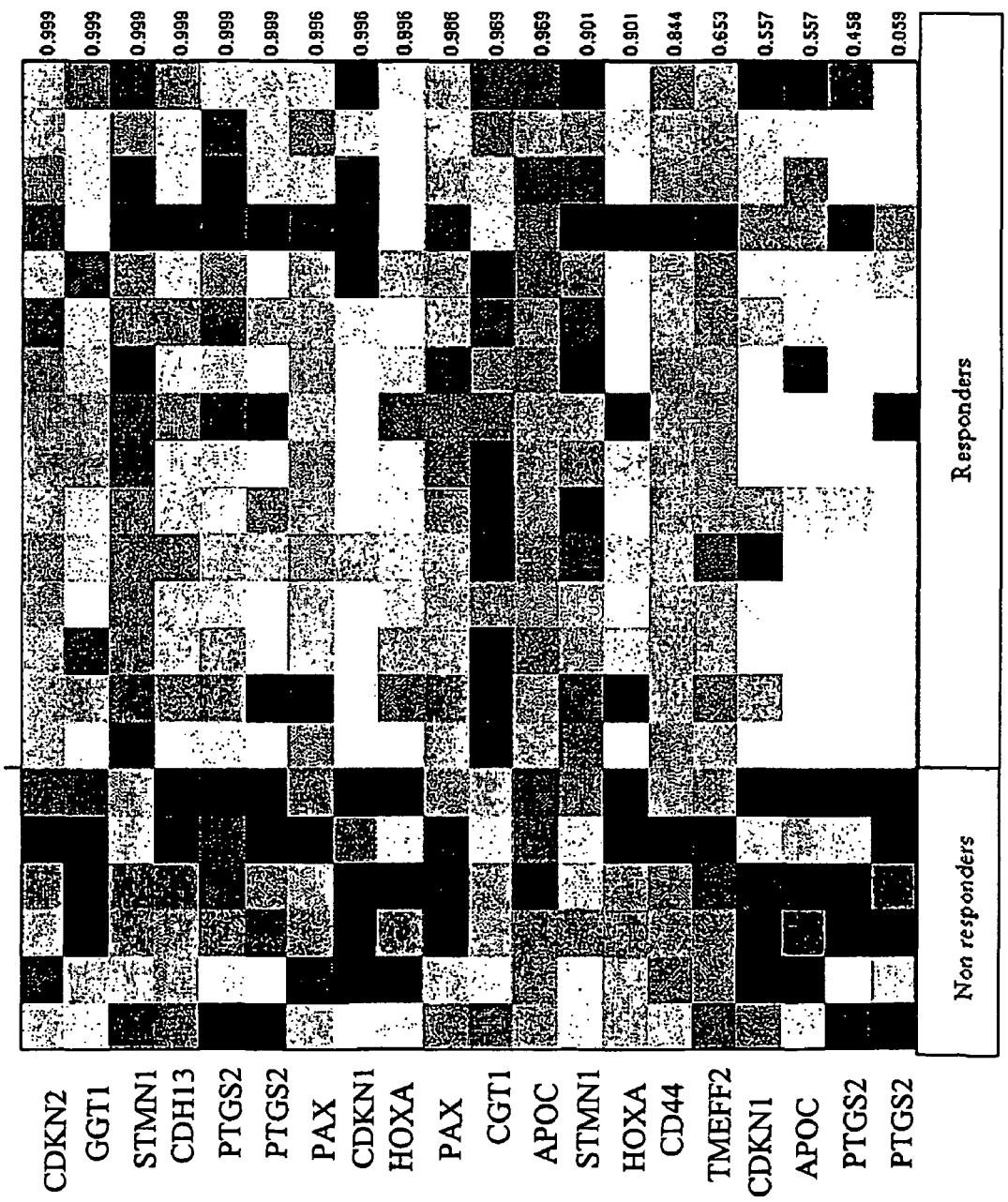
Figure 8:
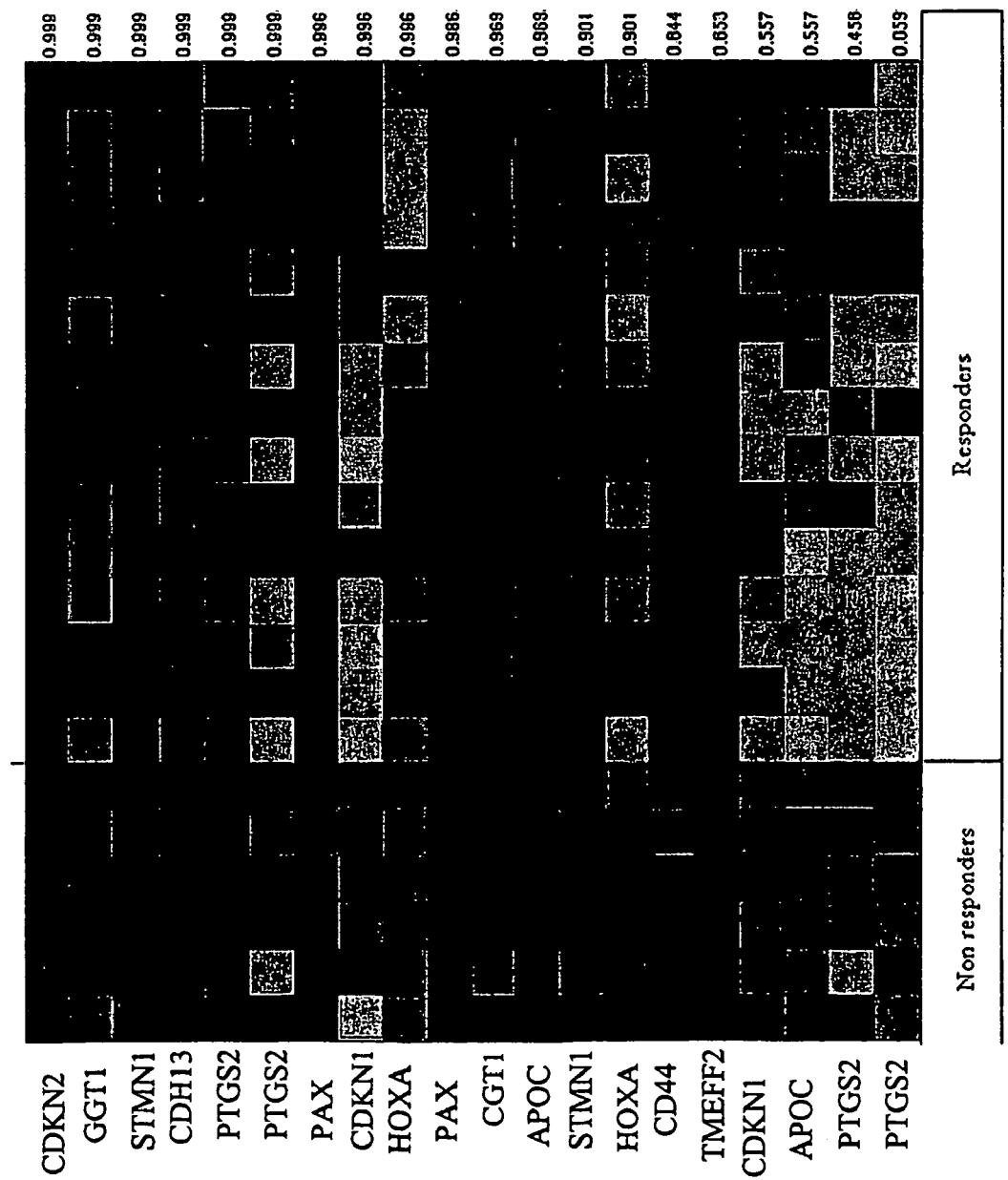

In the classification shown in FIGS. 7 and 8 the gene PTGS2 was significantly more methylated in non responders to the drug Tamoxifen wherein subjects with a disease free survival of less than 24 months were classified as non responders and subjects with a disease free survival of greater than 100 months were classified as responders. This classification was carried out with a sensitivity of 0.89 and a sensitivity of 0.48.

Data Set 1: Metastatic Setting

Figure 2:
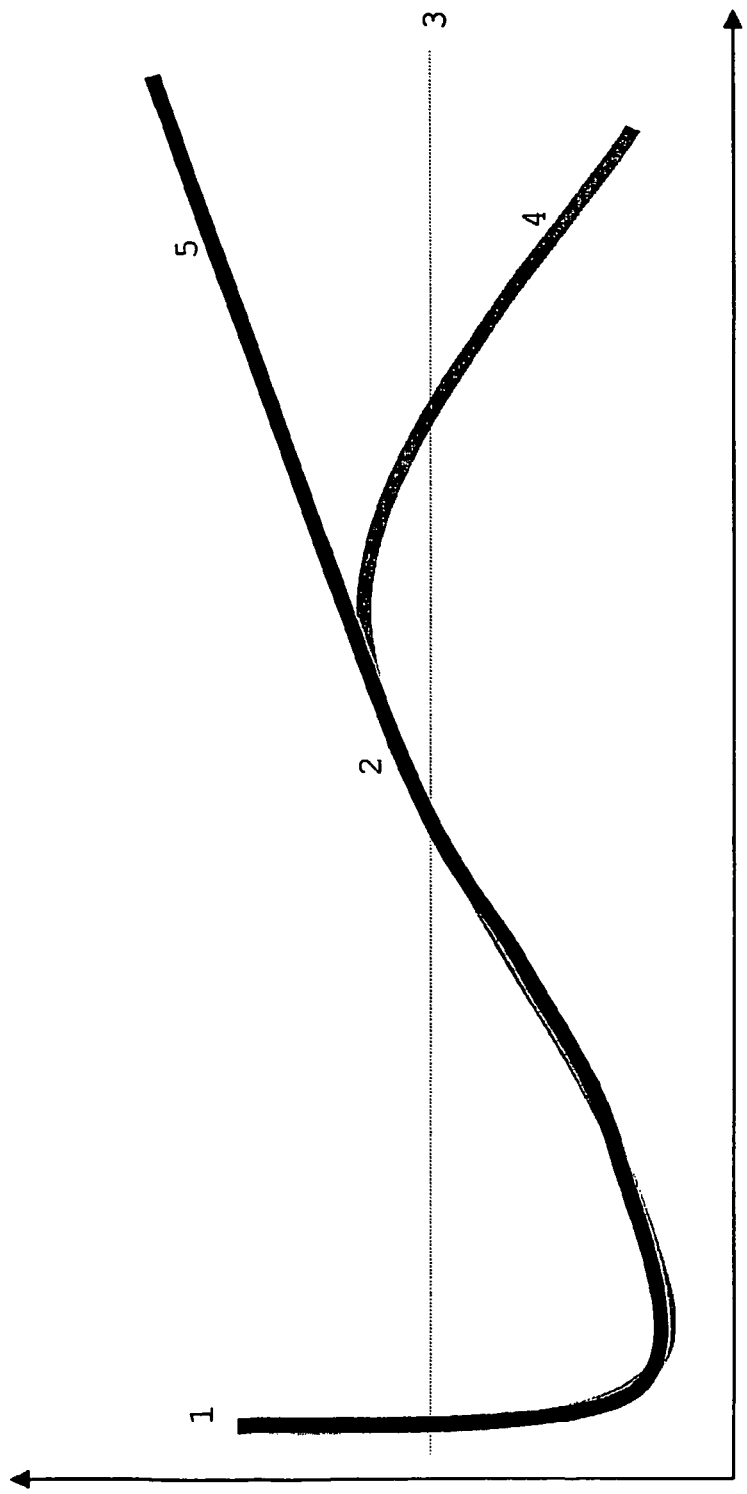
FIG. 2 shows another preferred application of the method according to the invention. The X axis shows the tumour(s) mass, wherein the line '3' shows the limit of detectability. The Y-axis shows time. Accordingly said figure illustrates a simplified model of Endocrine treatment of an late stage breast tumour wherein primary treatment was surgery (at point 1), followed by relapse which is treated by Tamoxifen (2). In a first scenario a responder to treatment (4) is shown as remaining below the limit of detectability for the duration of the observation. A non responder to the treatment (5) does not recover from the relapse.

Analysis of the methylation patterns of patient samples treated with Tamoxifen in a metastatic setting (see FIG. 2) is shown in the matrices according to FIGS. 9 to 12. The subjects analysed in this classification had relapsed following an initial treatment, the subsequent metastasis being treated by Tamoxifen.

Figure 9:
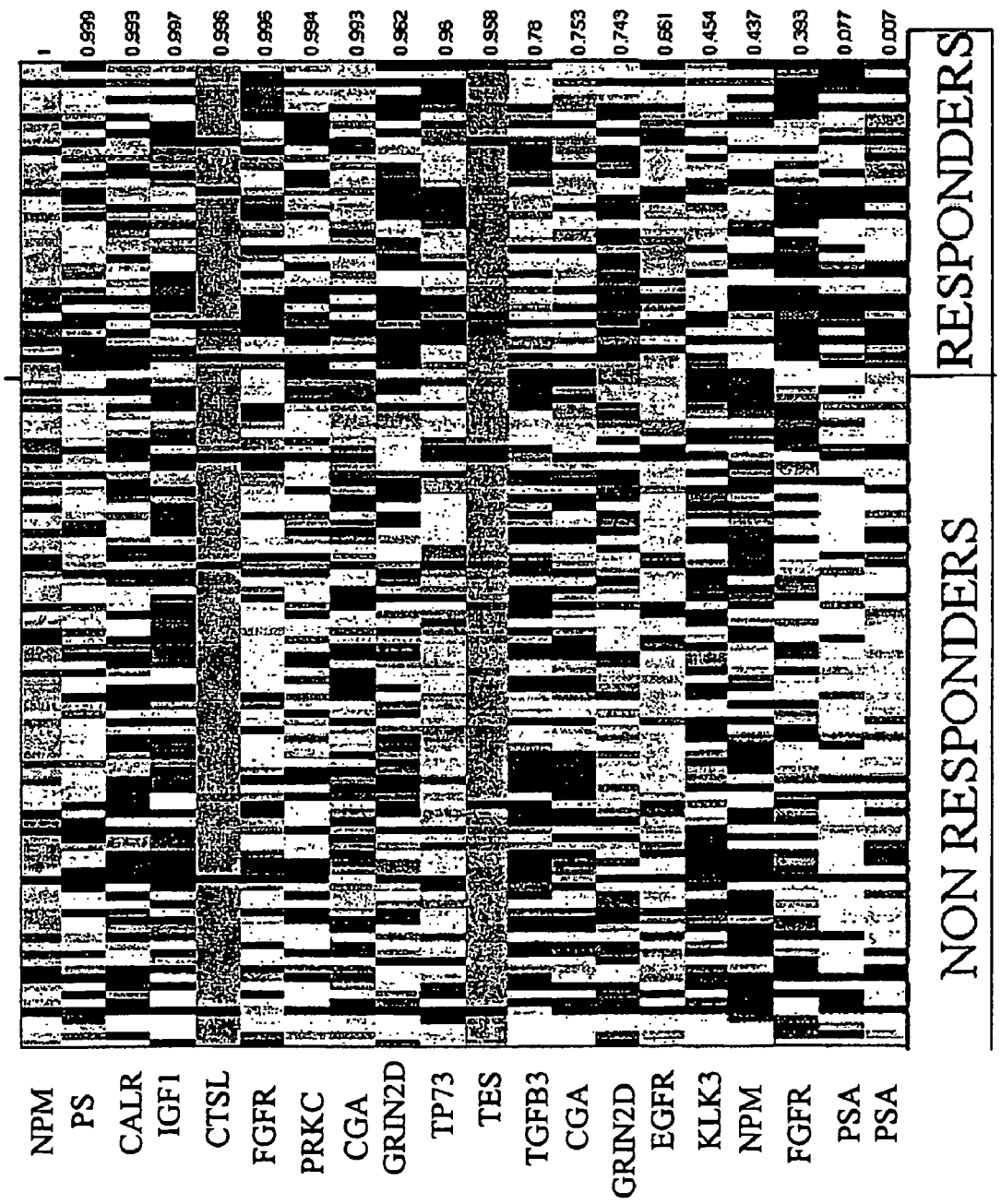
Figure 10:
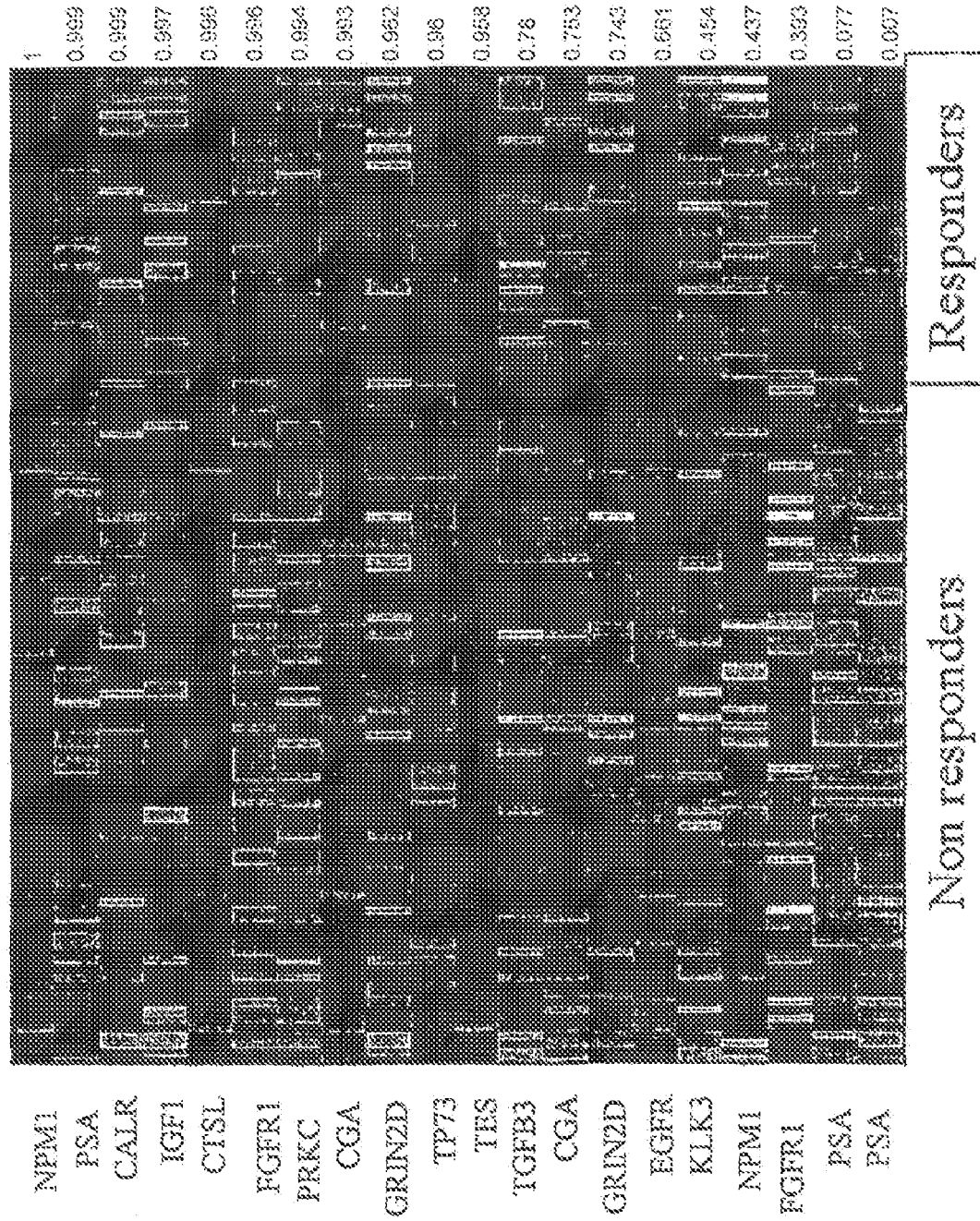
Figure 11:
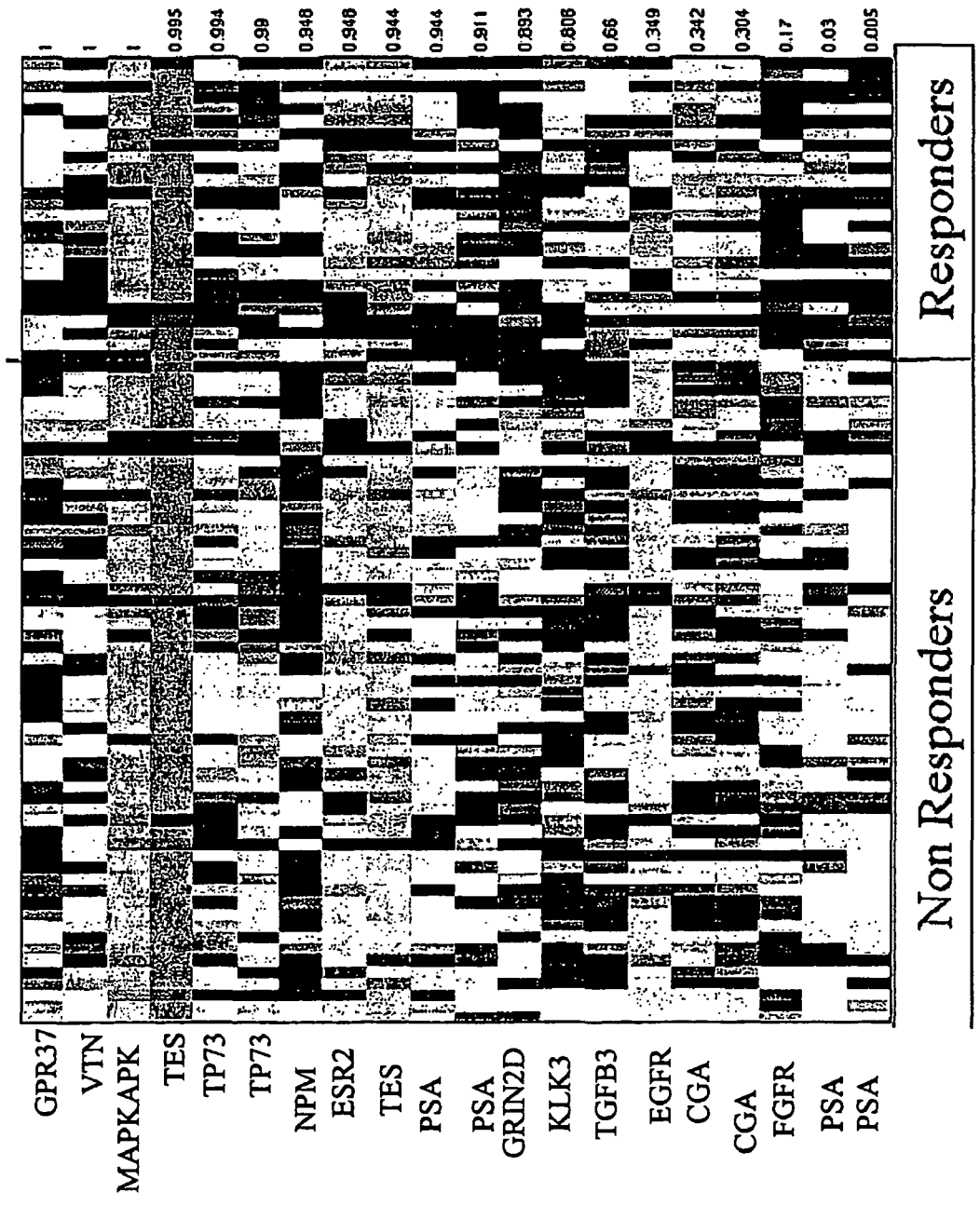

In the classification shown in FIGS. 9 and 10 the genes FGFR1 and PSA were significantly less methylated in non responders to the drug Tamoxifen. Subjects with a progressive disease were classified as non responders and subjects who achieved partial or complete remission were classified as responders. This classification was carried out with a sensitivity of 0.45 and a sensitivity of 0.81.

The sensitivity of this classification could be improved by only analysing those patients who had not undergone chemotherapy. In this classification, shown in FIGS. 11 and 12 the genes FGFR1, PSA and CGA were significantly less methylated in non responders to the drug Tamoxifen. The sensitivity of the classification was thereby improved to 0.54 and the specificity to 0.85.

Data Set 2: Metastatic Setting

Figure 12:
FIGS. 12 and 13 show a ranked matrix of data obtained according to Example 3 according to CpG methylation differences between the two classes of tissues (responder and non-responder to endocrine treatment in a metastatic setting), using an algorithm. The Figures are shown in greyscale, wherein the most significant CpG positions are at the bottom of the matrix with significance decreasing towards the top. Black indicates total methylation at a given CpG position, white represents no methylation at the particular position, with degrees of methylation represented in grey, from light (low proportion of methylation) to dark (high proportion of methylation). Each row represents one specific CpG position within a gene and each column shows the methylation profile for the different CpGs for one sample. On the left side, the gene name is shown, on the right side p values for the individual CpG positions are shown. The p values are the probabilities that the observed distribution occurred by chance in the data set.
Figure 13:
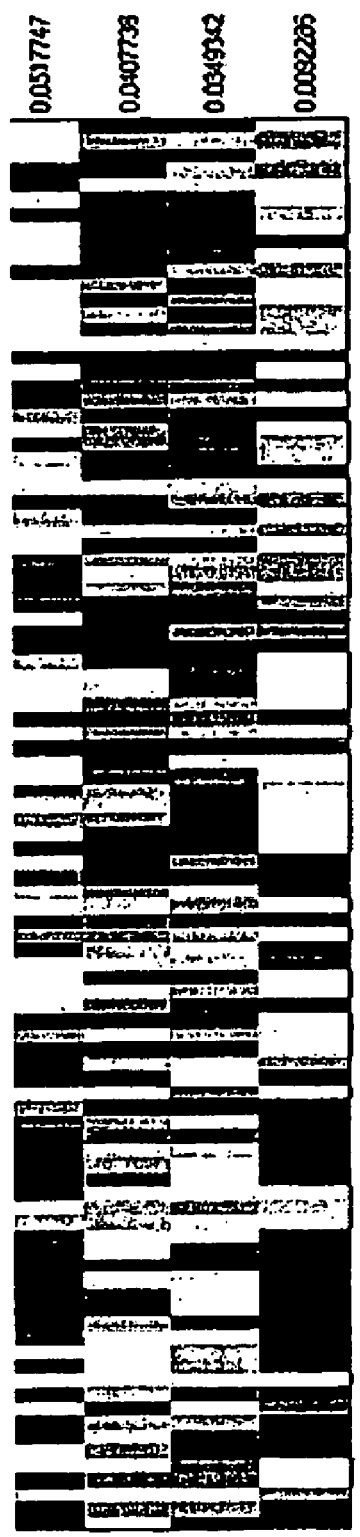

FIG. 12 shows the analysis of the total sample set wherein responders to the drug and compared to non responders, significant differences in methylation between the two classes of tissue were observed in the genes STMN 1 and PSA.

Wherein patients who had received chemotherapy as an additional therapy were excluded from the data set, an additional marker was observed CGA (see FIG. 13).

Data Set 2: Adjuvant Setting

Every CpG was put into a Cox proportional hazard model together with the known predictive markers N-stage and tumour size. The best marker was the gene PITX 2.

The Cox model for the best marker (oligonucleotide number 3522:2087) is:

|  | coef | Exp(coef) | Se(coef) | z | P |
|---|---|---|---|---|---|
| nStage | 1.677 | 5.35 | 0.5390 | 3.11 | 0.00190 |
| 3522:2087 | 2.885 | 17.90 | 0.8211 | 3.51 | 0.00044 |
| Tumour Size | 0.120 | 1.13 | 0.0926 | 1.30 | 0.19000 |

This shows that 3522:2087 gives information about survival time independent of nStage. The tumour size has no significant predictive power for expected survival time.

Data Set 4: Metastatic Setting

In order to determine the ability of each gene promoter to predict success or failure of Tamoxifen treatment, the individual CpGs measured were combined per gene using Hotelling's $T^2$ statistics. Several genes were significantly associated with response to tamoxifen after correcting for multiple comparison with a moderate conservative false discovery rate of 25% (see FIG. 3). The genes were ONECUT2, WBP11, CYP2D6, DAG1, ERBB2, S100A2, TFF1, TP53, TMEFF2, ESR1, SYK, RASSF1, PITX2, PSAT1, CGA and PCAF.

Figure 15:
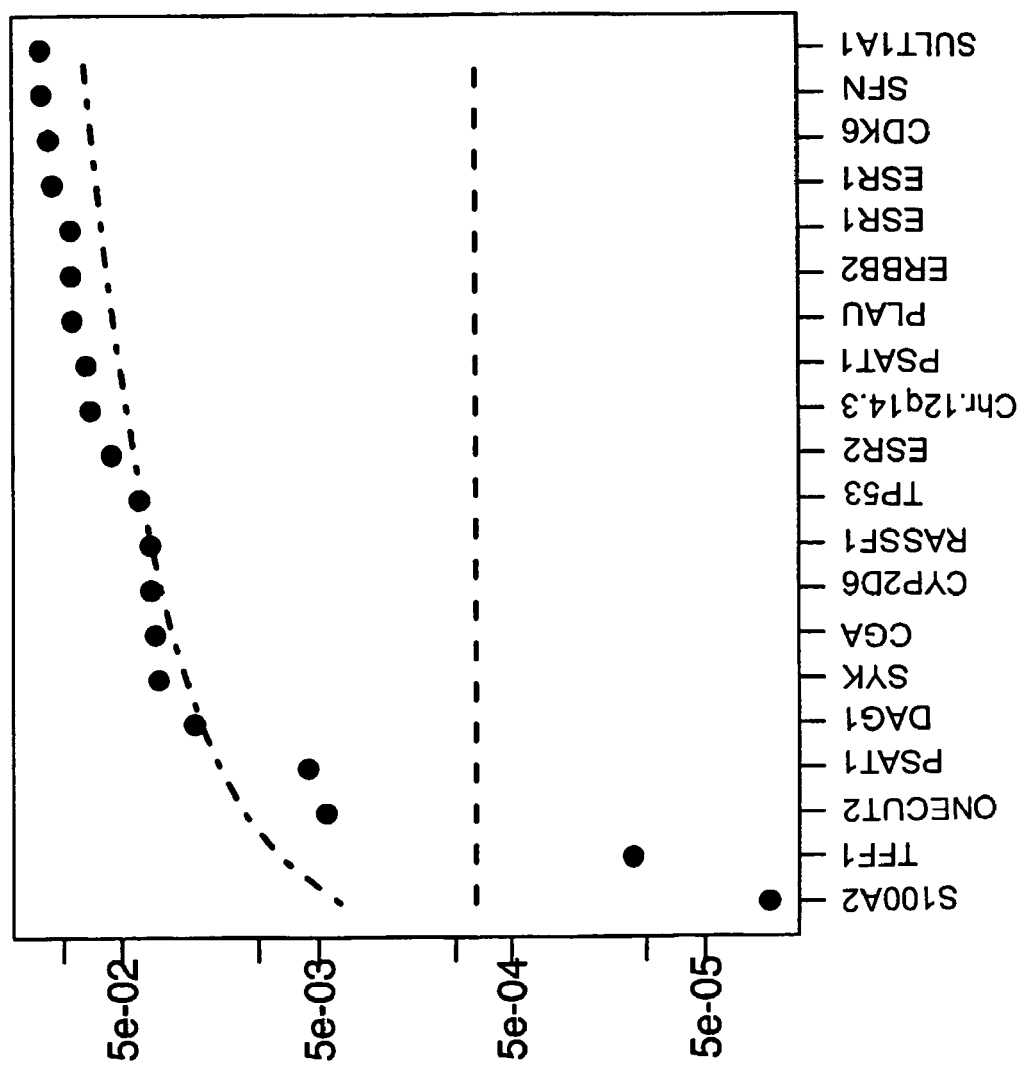
FIG. 15 shows the uncorrected p-values on a log-scale. P-values were calculated from Likelihood ratio (LR) tests from multivariate logistic regression models. Each individual genomic region of interest is represented as a point, the upper dotted line represents the cut off point for the 25% false discovery rate, the lower dotted line shows the Bonferroni corrected 5% limit.

FIG. 15 shows the uncorrected p-values on a log-scale. P-values were calculated from Likelihood ratio (LR) tests from multivariate logistic regression models. Each individual genomic region of interest is represented as a point, the upper dotted line represents the cut off point for the 25% false discovery rate, the lower dotted line shows the Bonferroni corrected 5% limit.

Figure 16:
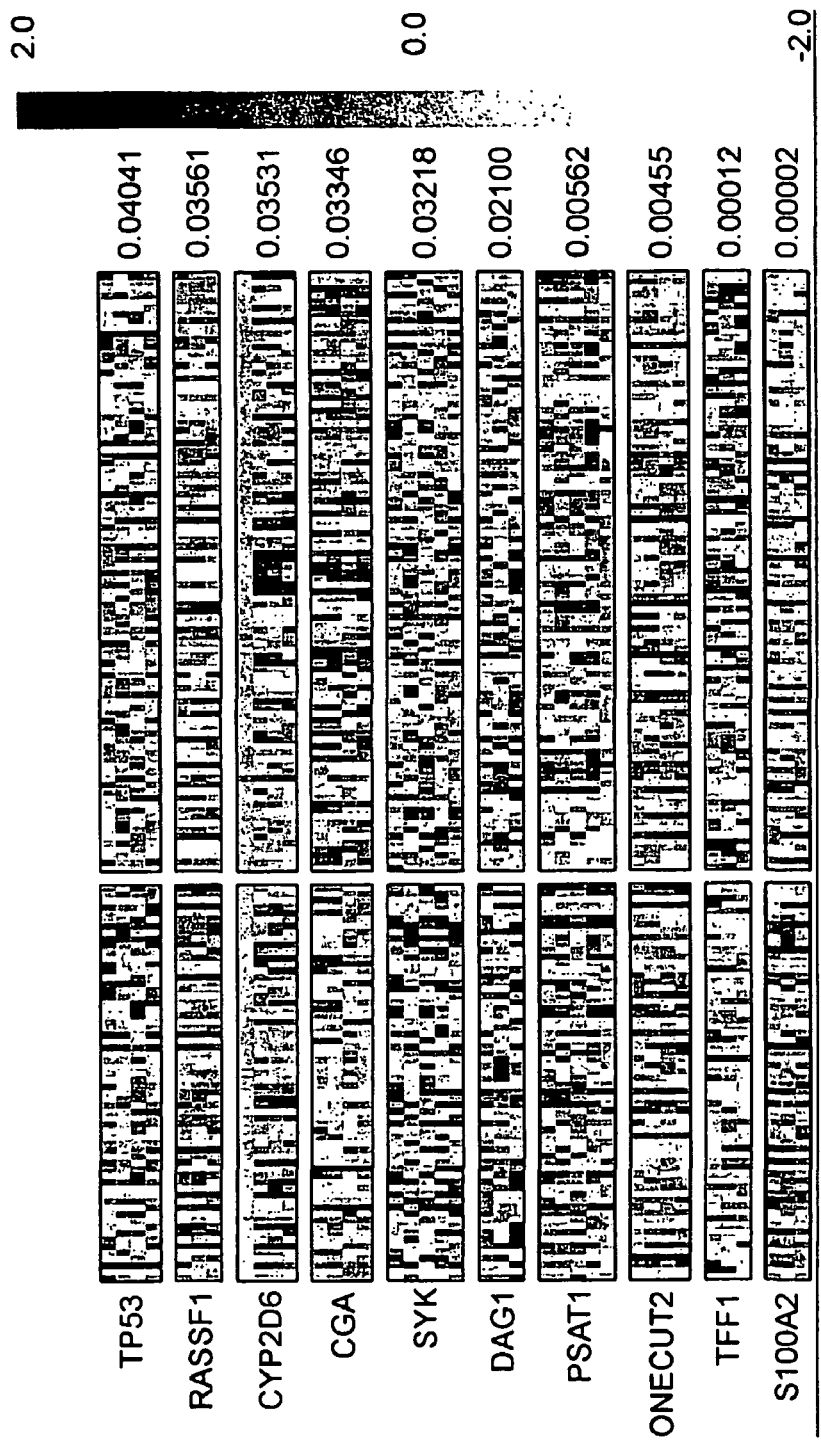
FIG. 16 shows a ranked matrix of the best 10 amplificates of data obtained according to Example 1 (Dataset 4). P-values were calculated from Likelihood ratio (LR) tests from multivariate logistic regression models. The figure is shown in greyscale, wherein the most significant CpG positions are at the bottom of the matrix with significance decreasing towards the top. Black indicates total methylation at a given CpG position, white represents no methylation at the particular position, with degrees of methylation represented in grey, from light (low proportion of methylation) to dark (high proportion of methylation). Each row represents one specific CpG position within a gene and each column shows the methylation profile for the different CpGs for one sample. The p-values for the individual CpG positions are shown on the right side. The p-values are the probabilities that the observed distribution occurred by chance in the data set.
Figure 17:
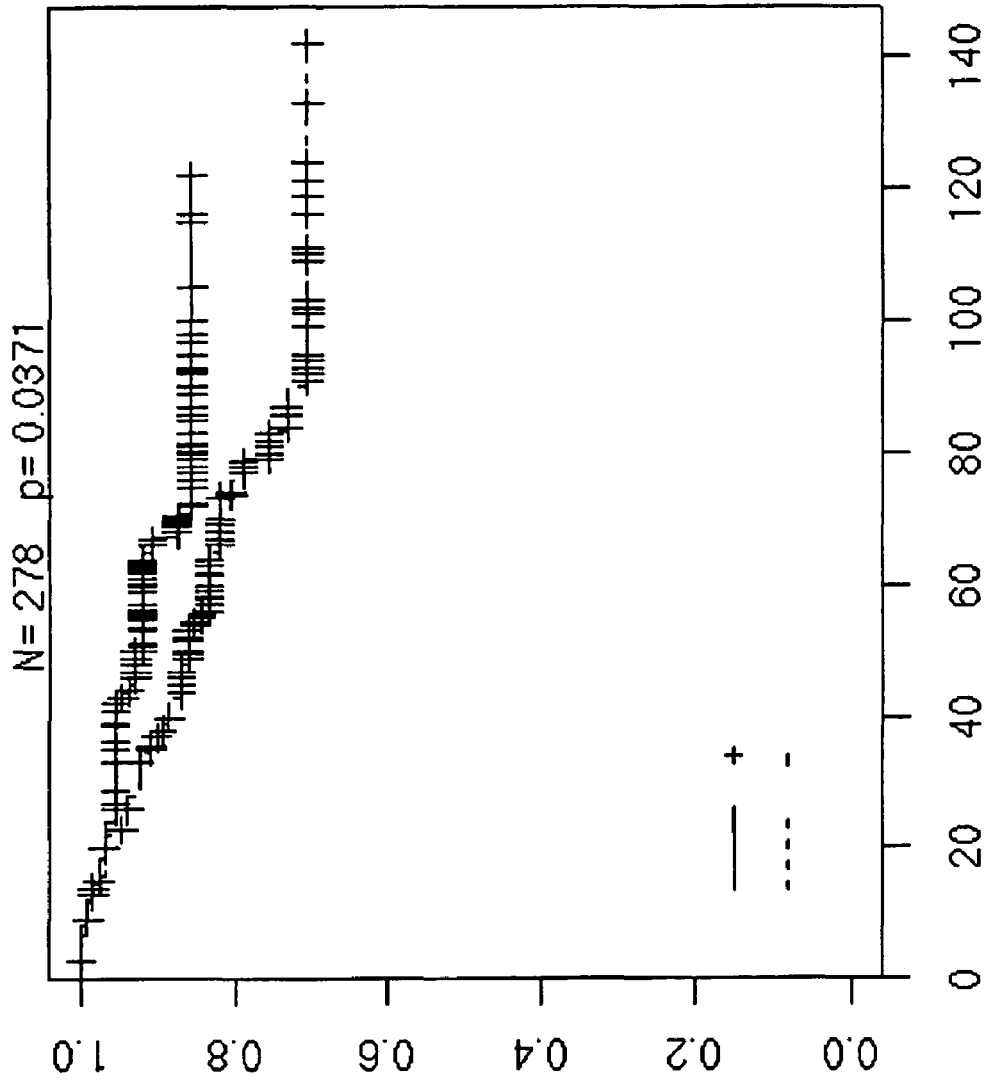
FIG. 17 shows the Kaplan-Meier estimated disease-free survival curves for the gene ESR1, the dotted line (lower curve) shows non-responders whereas the unbroken line (upper curve) shows responders.
Figure 18:
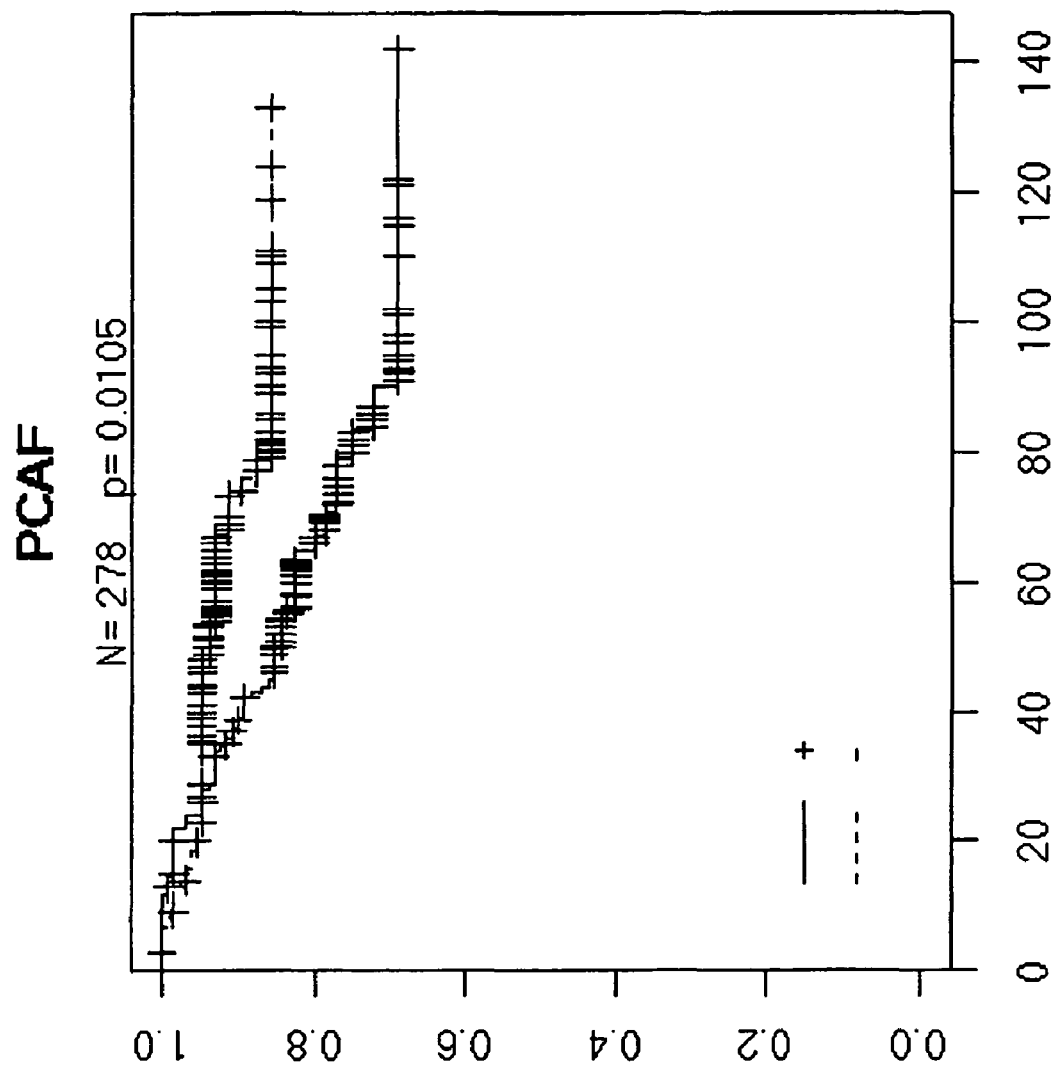
FIG. 18 shows the Kaplan-Meier estimated disease-free survival curves for the gene PCAF, the dotted line (upper curve) shows non-responders whereas the unbroken line (lower curve) shows responders.
Figure 19:
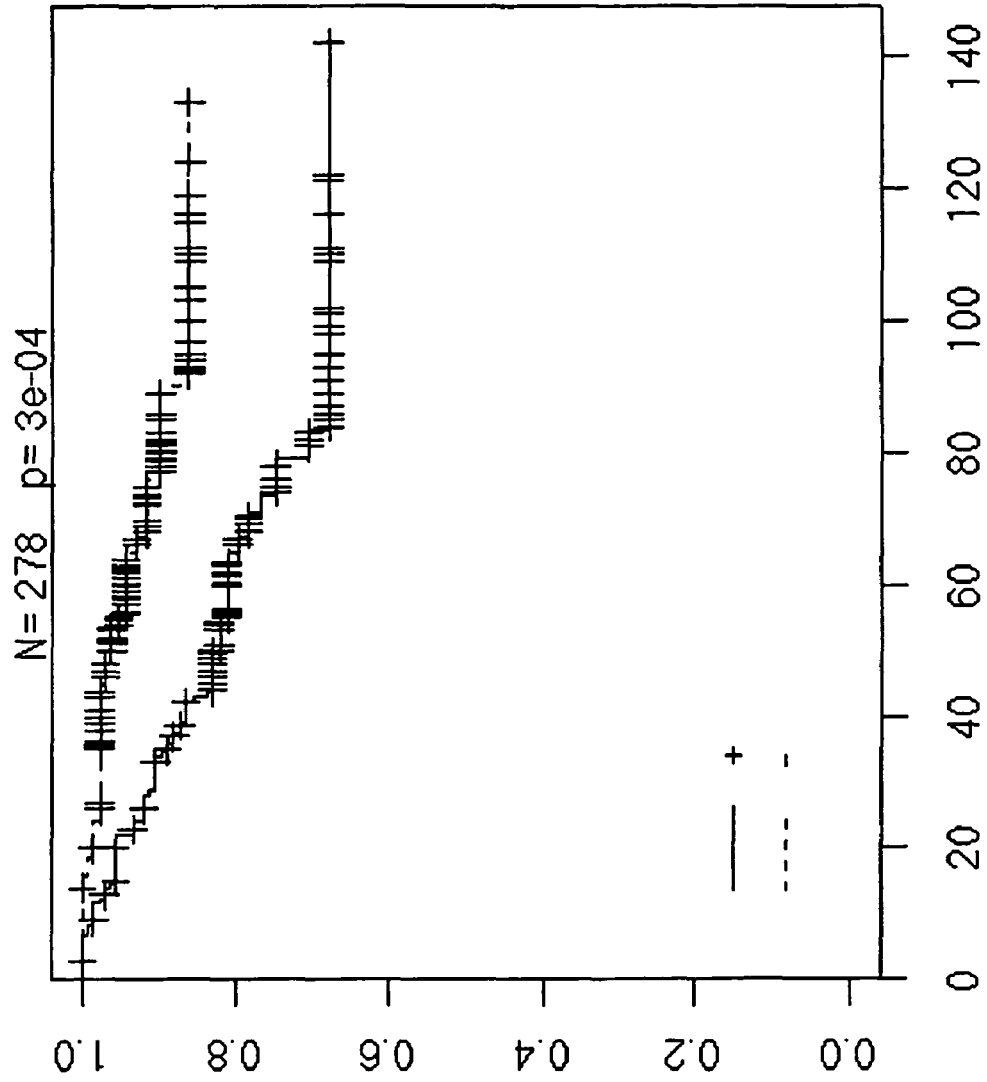
FIG. 19 shows the Kaplan-Meier estimated disease-free survival curves for the gene PITX2, the dotted line (upper curve) shows responders whereas the unbroken line (lower curve) shows non-responders.
Figure 20:
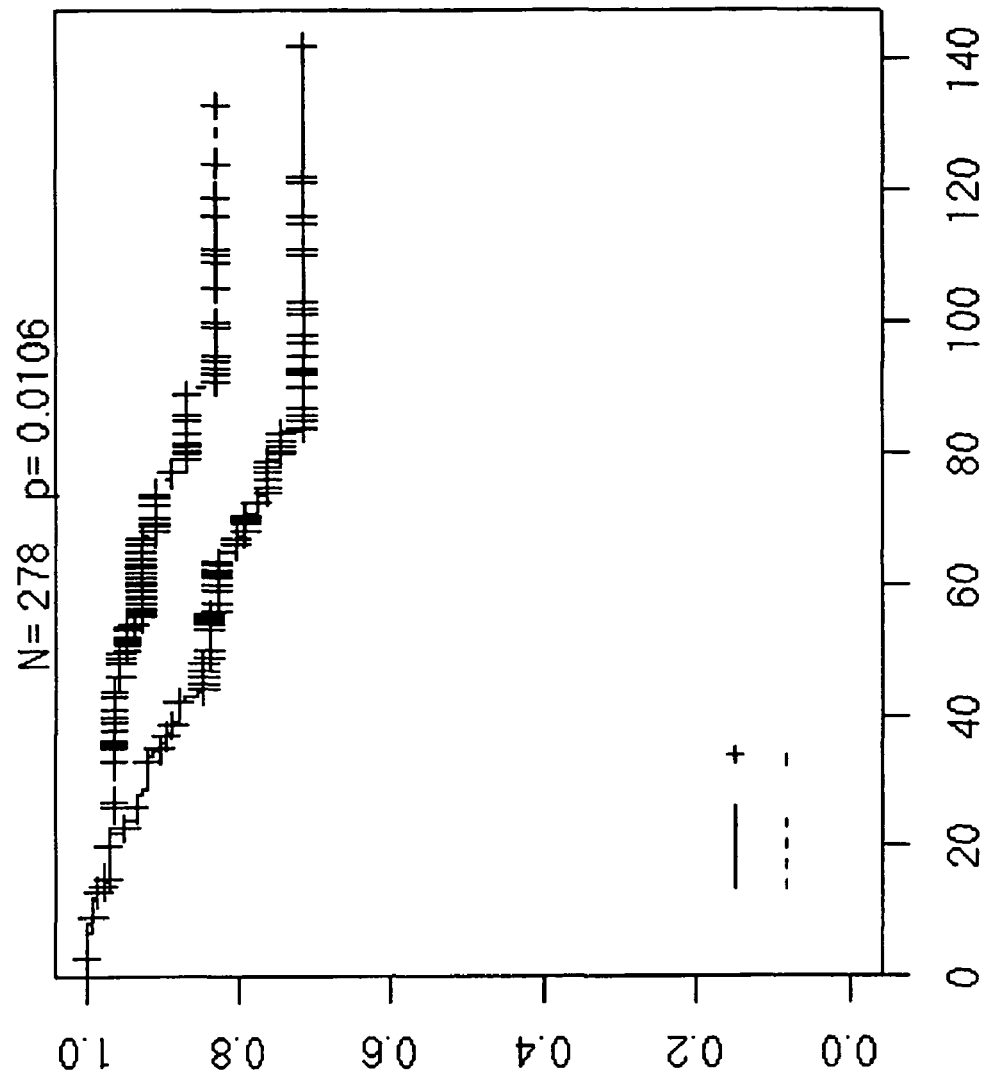
FIG. 20 shows the Kaplan-Meier estimated disease-free survival curves for the gene TMEFF2, the dotted line (upper curve) shows non-responders whereas the unbroken line (lower curve) shows responders.
Figure 21:
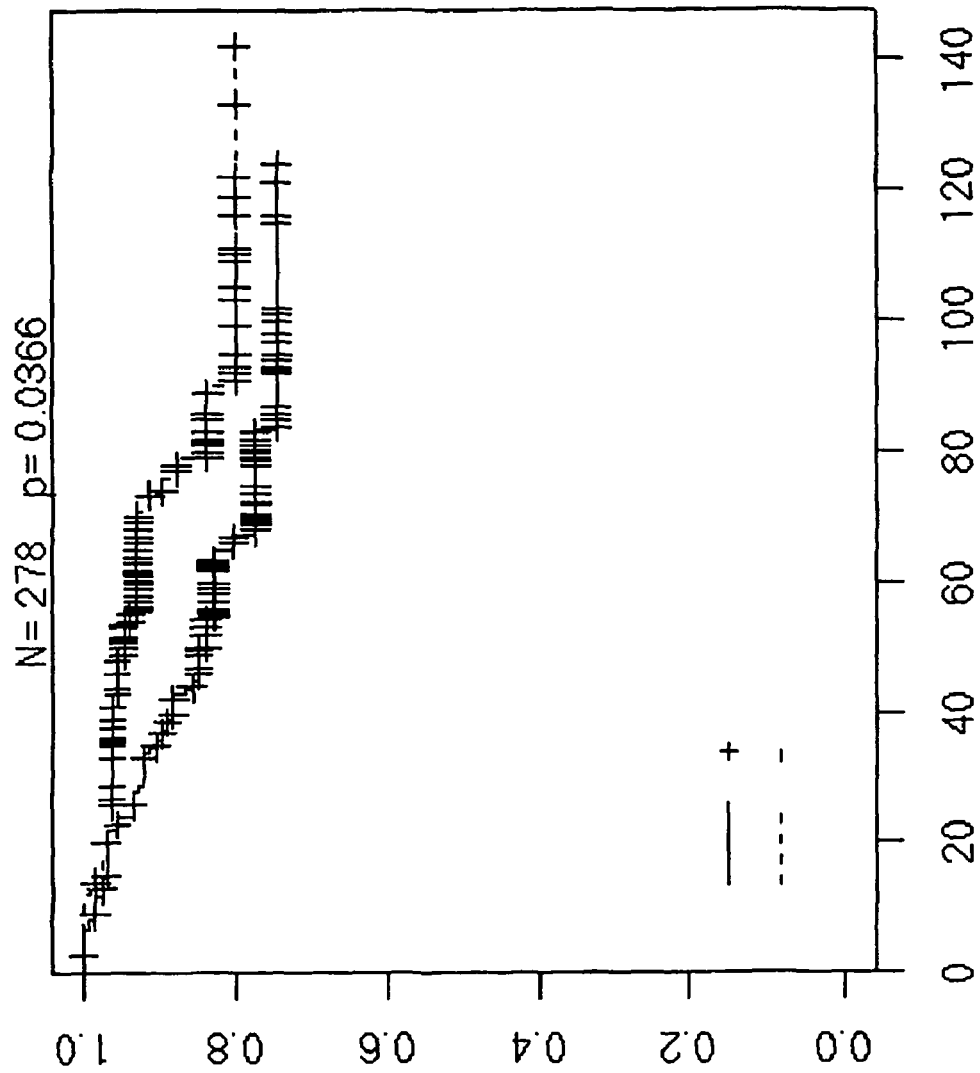
FIG. 21 shows the Kaplan-Meier estimated disease-free survival curves for the gene WBP11, the dotted line (lower curve) shows non-responders whereas the unbroken line (upper curve) shows responders.
Figure 22:
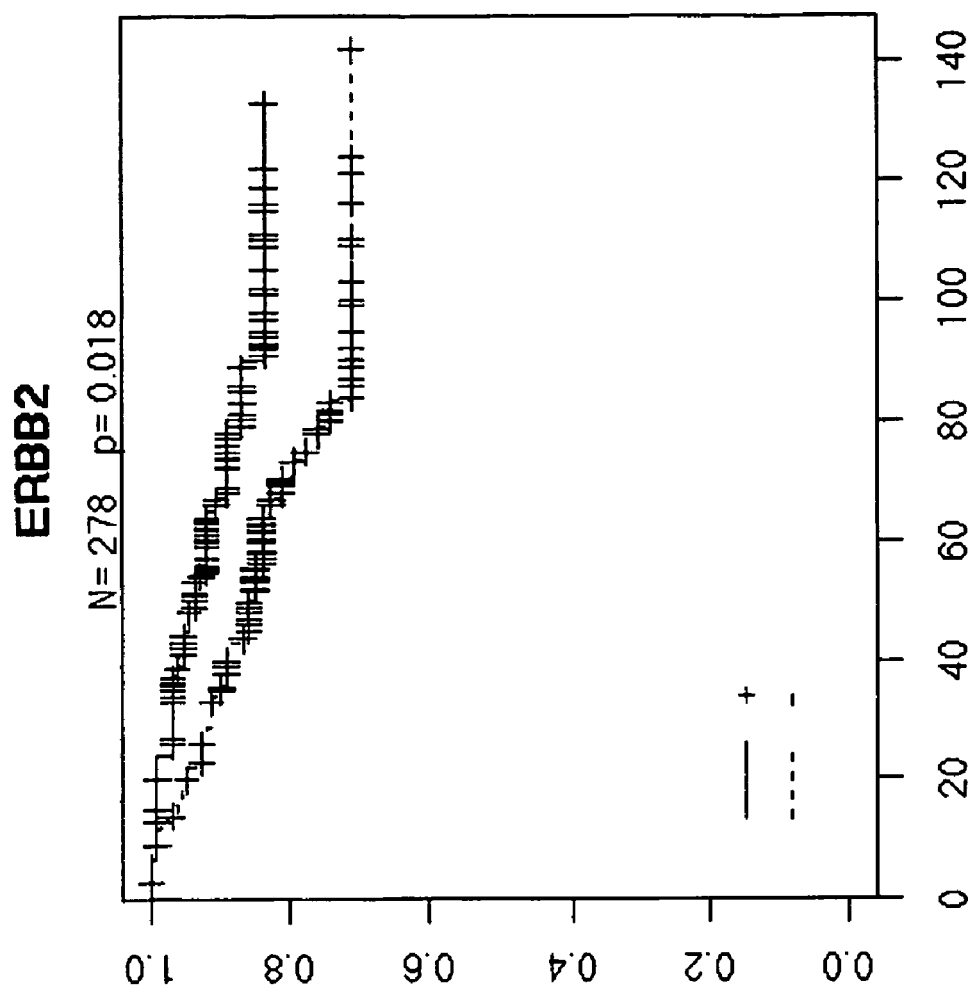
FIG. 22 shows the Kaplan-Meier estimated disease-free survival curves for the gene ERBB2, the dotted line (lower curve) shows non-responders whereas the unbroken line (upper curve) shows responders.

FIG. 16 shows a ranked matrix of the best 11 amplificates of data obtained according to Example 1 (Dataset 4). P-values were calculated from Likelihood ratio (LR) tests from multivariate logistic regression models. The figure is shown in greyscale, wherein the most significant CpG positions are at the bottom of the matrix with significance decreasing towards the top. Black indicates total methylation at a given CpG position, white represents no methylation at the particular position, with degrees of methylation represented in grey, from light (low proportion of methylation) to dark (high proportion of methylation). Each row represents one specific CpG position within a gene and each column shows the methylation profile for the different CpGs for one sample. The p-values for the individual CpG positions are shown on the right side. The p-values are the probabilities that the observed distribution occurred by chance in the data set.

Data Set 4: Adjuvant Setting

For each amplificate, the mean methylation over all oligo-pairs for that amplificate was calculated and the population split into equal sized groups according to their mean methylation values. The results are shown in FIGS. 17 to 21, as Kaplan-Meier estimated disease-free survival curves. The p-values were:

| | |
|---|---|
| ESR1: | p = 0.0371 |
| PCAF: | p = 0.0105 |
| PITX2: | p = 3e−04 |
| TMEFF2: | p = 0.0106 |
| WBP11: | p = 0.0366 |
| ERBB2: | p = 0.018 |

Data Set 3

In order to determine the ability of each gene promoter to predict success or failure of Tamoxifen treatment, the individual CpGs measured were combined per gene using Hotelling's $T^2$ statistics. To identify potential markers, the inventors performed our initial analysis on those 123 patients who showed the extreme types of response; either an objective response (CR+PR, 45 patients) or a progressive disease right from the start of treatment (PD, 78 patients). Several genes were significantly associated with response to tamoxifen after correcting for multiple comparison with a moderate conservative false discovery rate of 25% (see FIG. 3). The genes were STMN1, SFN, S100A2, TGFBR2, SYK, GRIN2D, PSA, COX7A2L, VTN and PRKCD.

From the DNA methylation data matrices we concluded that for the majority of the genes CpG island hypermethylation was correlated with favourable response to tamoxifen treatment, while for stathimin 1/oncoprotein 18 (STMN1) and stratifin/14-3-3 protein σ (SFN) hypomethylation was associated with remission.

Subsequently, all 200 patients including those with an intermediate type of response (59 patients with stable disease (SD, no change of disease for more than 6 months) and 18 patients with stable disease for 6 months or less) were analysed in logistic regression analysis. For each of the selected genes, we combined per gene the estimates from the logistic regression for overall response (=objective response+SD) of the different CpG dinucleotides measured. In the whole cohort, for all ten genes, the response rate to tamoxifen treatment was approximately 15 to 20% higher (odd ratios [OR's] ranging from 1.5 to 3.5) for patients whose tumours had a favourable DNA methylation status than those with an unfavourable status. In concordance, for the marker genes, the median PFS in the former group of patients was on average 1.8 times longer than that in the latter group (hazard ratios (HR's) ranging from 0.54 to 0.77). Thus, also in the complete cohort, these marker genes were associated with disease outcome after tamoxifen treatment.

Prediction of response to tamoxifen treatment in advanced breast cancer patients is based traditionally on the patient, disease, and tumour characteristics, i.e., age, first dominant site of relapse, disease-free interval, and ER status. We compared a predictive score calculated with the multivariable estimates of the traditional predictive factors (traditional factors-based score) with a score derived from DNA methylation data only (DNA methylation-based score). For a DNA methylation-based score, we included only genes whose DNA methylation status predicted response independent of each other. To establish this, we added the DNA methylation status information of each of the marker genes simultaneously to a multivariable logistic regression model. After backward elimination of the non-significant genes (P<0.05), the genes STMN1, SFN, S100A2, TGFBR2, SYK, GRIN2D, PSA, COX7A2L, VTN and PRKCD, were statistically significant and predicted response, independent of one another. The DNA methylation-based score that was subsequently compared to the traditional factors-based score was derived from the multivariable estimates of these genes.

The score for each tumour based on either traditional predictive factors or DNA methylation status was used to divide the patients into 4 groups by its 25th, 50th, and 75th percentile values (Table 3). The DNA methylation-based score showed a much better discriminatory strength with overall response than the traditional factors-based score (Table 3). The overall response rates in the DNA methylation-based score increased from 26% for the patients in the first quarter (q1) (OR set at 1.0), 34% for in the second quarter (q2) (OR=1.5), 66% in third for q3 (OR=5.5) and 82% and last quarter for q4 (OR=13.0) (P<0.001) while for the traditional factors-based score the rates increased only from 36% (OR, set at 1.0) for q1 of this score, via 46% (OR=1.5) (q2) to 64% (OR=3.2) and 62% (OR=2.9) (q3) (q4), respectively (P=0.013) (Table 3).

Figure 14:
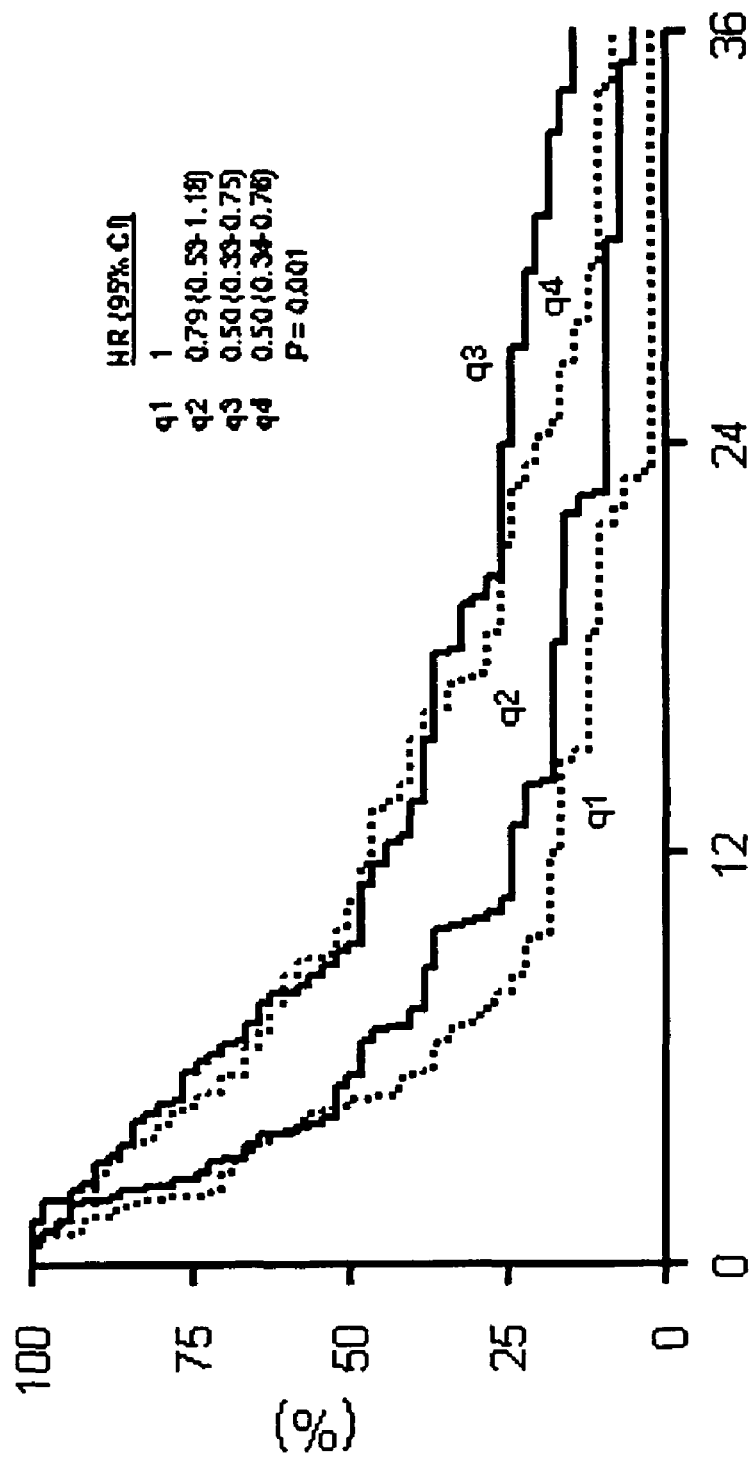
FIG. 14 shows the progression-free survival (PFS) curves of combination scores according to Example 1 (Dataset 3). PFS curves after start of tamoxifen treatment of patients are shown. They are grouped using a predictive score ($\chi^2$=14.0; 3 degrees of freedom) based on the traditional predictive markers age, dominant site of relapse, disease-free interval and ER level (A). A DNA methylation-based score ($\chi^2$=27.5; 3 degrees of freedom) is presented comprising the statistically independent predicting genes phosphoserine amino transferase (PSA-T), stathmin (STMN1), S100 protein A2 (S100A2, transforming growth factor β receptor II (TGFBR2), and glutamate receptor 2D (GRIN2D) (B). Survival curves were generated and significance calculated as described in Example 1. The calculated predictive scores were divided into 4 groups (q1-q4) with 50 patients each and using the $25^{th}$, $50^{th}$, and $75^{th}$ percentile of the values. The numbers below the X-axis represent the number of patients at risk in each group at the indicated time points of 0, 12, 24, and 36 months. Progression free survival (in percentage) is plotted on the Y-axis and time to progression (in months) is plotted on the X-axis.
Figure 14:
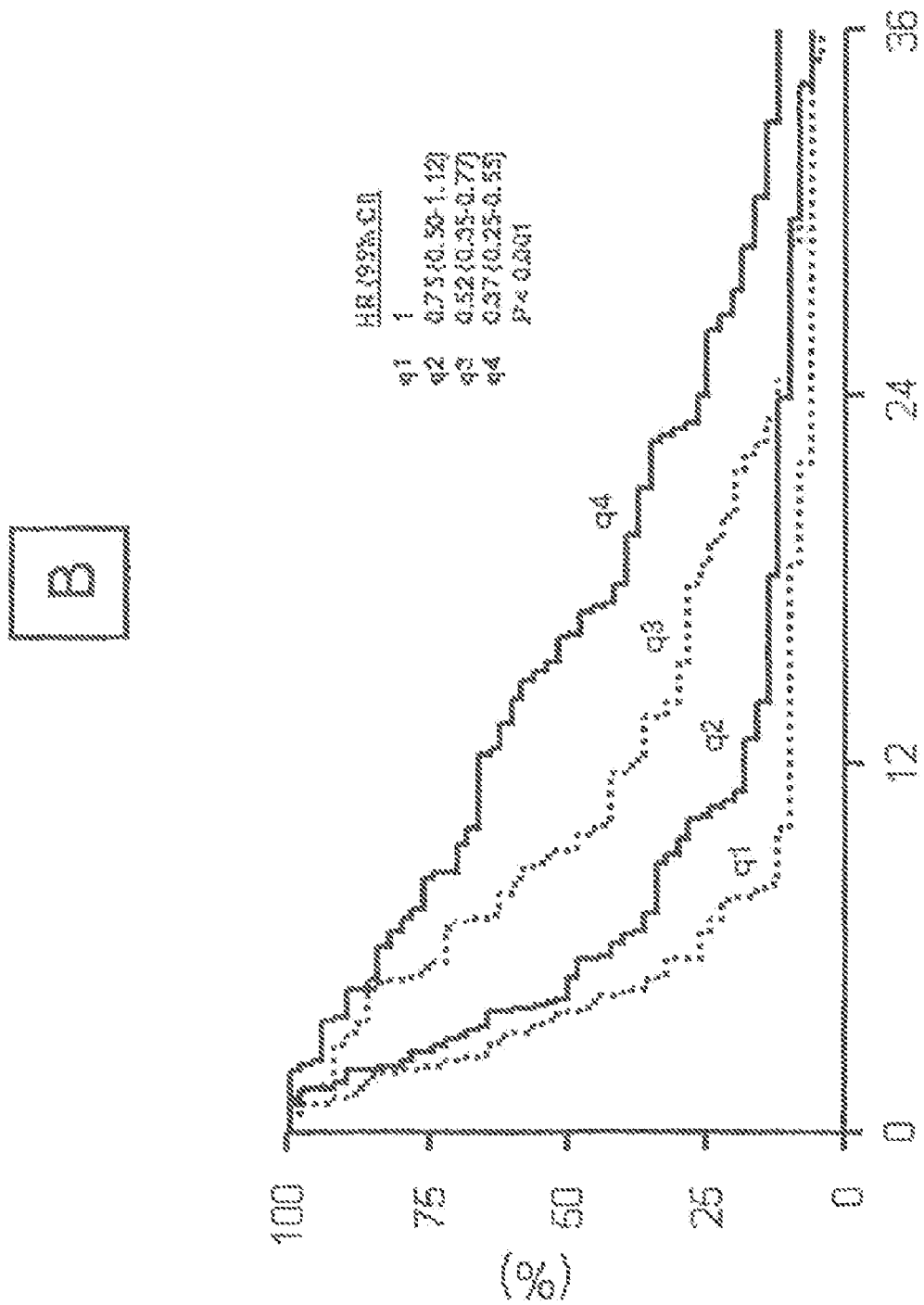

Similarly, median PFS in the extreme quarters for the DNA methylation-based score differed 4.2 times (from 3.8 to 16.1 months) while for the traditional factors-based score the difference between the two extreme quarters was only half of that (2.1 times; from 4.7 to 9.7 months) (compare curves of FIG. 14A with FIG. 14B).

Hence, we have shown for the first time that an epigenetic profile based on the CpG island DNA methylation status of promoter regions of just five genes can predict the likelihood of therapy response in patients with ER-positive advanced breast cancer treated with tamoxifen therapy. Furthermore, it appeared that this prediction was much more accurate than the prediction based on commonly used traditional predictive factors, suggesting that DNA methylation analysis may be useful for clinical therapy decisions. Epigenetic profiling of tumour tissue DNA can therefore be a competitive and simple alternative for tedious mRNA profiling that is highly dependent on well-preserved tumour tissue material. Besides that epigenetic DNA profiles are very stable, are localised to specific sites (the promoter region of a gene) and can be easily amplified by PCR. Above and beyond, DNA methylation status determination can be performed on archived frozen or easily accessible paraffin-embedded tumour tissue material, making it widely applicable in the routine clinical setting.

EXAMPLE 2

Lightcycler Assay

In the following example the Tamoxifen response relevant methylation status of the gene PSAT1 was verified by analysis of 24 patient samples using a Real-Time assay comprising a blocker oligonucleotide and Lightcycler probes.

| Primer: | TAGGTTGGTAGGGGTAG | (SEQ ID NO: 2143) |
| Primer: | AAAACTCACATCCCCATTAA | (SEQ ID NO: 2144) |
| Probe: | TTTTTTGTATTGATTAAAAATGGGGGTTGAAATAGTA | (SEQ ID NO: 2145) |
| Methylation specific Probe: | CGCGAGGAGGAGTAATTGTTTC | (SEQ ID NO: 2146) |
| Methylation specific Probe: | TGTGAGGAGGAGTAATTGtTTTGATTT | (SEQ ID NO: 2147) |

The reactions were each run in triplicate on each DNA sample with the following assay conditions:

Reaction Solution:

| Qiagen HotStarTaq | 5 U |
| 10× PCR-buffer | 1× |
| MgCl₂ | 3 mM |
| Primers | 300 nM each |
| Probes | 250 nM each |
| dNTPs | 200 nM each |
| BSA | 0.25 mg/ml |
| template-DNA | 10 ng |

Cycling Profile:
95° C. denaturation for 15 minutes
55 cycles: 95° C. 10 seconds, 55° C. 20 seconds, 57° C. 3 seconds, 72° C. 20 seconds. Results are shown in Table 4.

TABLE 1

| No. | Gene: | Primer: | Amplificate Length: |
|---|---|---|---|
| 1 | ABCB1 (SEQ ID NO: 1) | TAAGTATGTTGAAGAAAGATTATTGTAG (SEQ ID NO: 795) TAAAAACTATCCCATAATAACTCCCAAC (SEQ ID NO: 796) | 633 |
| 2 | APOC2 (SEQ ID NO: 2) | ATGAGTAGAAGAGGTGATAT (SEQ ID NO: 797) CCCTAAATCCCTTTCTTACC (SEQ ID NO: 798) | 533 |
| 3 | CACNA1G (SEQ ID NO: 3) | GGGATTTAAGAGAAATTGAGGTA (SEQ ID NO: 799) AAACCCCAAACATCCTTTAT (SEQ ID NO: 800) | 707 |
| 4 | EGR4 (SEQ ID NO: 4) | AGGGGGATTGAGTGTTAAGT (SEQ ID NO: 802) CCCAAACATAAAGACAAAAT (SEQ ID NO: 801) | 293 |
| 5 | AR (SEQ ID NO: 5) | GTAGTAGTAGTAGTAAGAGA (SEQ ID NO: 803) ACCCCCTAAATAATTATCCT (SEQ ID NO: 804) | 460 |
| 6 | RB1 (SEQ ID NO: 6) | TTTAAGTTTGTTTTTGTTTTGGT (SEQ ID NO: 805) TCCTACTCTAAATCCTCCTCAA (SEQ ID NO: 806) | 718 |
| 7 | GP1BB (SEQ ID NO: 7) | GGTGATAGGAGAATAATGTTGG (SEQ ID NO: 807) TCTCCCAACTACAACCAAAC (SEQ ID NO: 808) | 379 |
| 8 | WT1 (SEQ ID NO: 8) | AAAGGGAAATTAAGTGTTGT (SEQ ID NO: 810) TAACTACCCTCAACTTCCC (SEQ ID NO: 809) | 747 |
| 9 | HLA-F (SEQ ID NO: 9) | TTGTTGTTTTTAGGGGTTTTGG (SEQ ID NO: 811) TCCTTCCCATTCTCCAAATATC (SEQ ID NO: 812) | 946 |

TABLE 1-continued

| No. | Gene: | Primer: | Amplificate Length: |
|---|---|---|---|
| 10 | ELK1 (SEQ ID NO: 10) | AAGTGTTTTAGTTTTTAATGGGTA (SEQ ID NO: 813) CAAACCCAAAACTCAGCTAT (SEQ ID NO: 814) | 966 |
| 11 | ARHI (SEQ ID NO: 12) | GTGAGTTTTGGGGTGTTTA (SEQ ID NO: 815) TCAATCTTACTTTCACACTACATAA (SEQ ID NO: 816) | 442 |
| 12 | BCL2 (SEQ ID NO: 13) | GTATTTTATGTTAAGGGGGAAA (SEQ ID NO: 817) AAAAACCACAATCCTCCC (SEQ ID NO: 818) | 640 |
| 13 | BRCA1 (SEQ ID NO: 14) | TGGATGGGAATTGTAGTTTT (SEQ ID NO: 819) TTAACCACCCAATCTACCC (SEQ ID NO: 820) | 537 |
| 14 | CALCA (SEQ ID NO: 15) | GTTTTGGAAGTATGAGGGTG (SEQ ID NO: 821) CCAAATTCTAAACCAATTTCC (SEQ ID NO: 822) | 614 |
| 15 | CCND2 (SEQ ID NO: 16) | TTTTGGTATGTAGGTTGGATG (SEQ ID NO: 823) CCTAACCTCCTTCCTTTAACT (SEQ ID NO: 824) | 426 |
| 16 | CDH1 (SEQ ID NO: 17) | GAGGTTGGGGTTAGAGGAT (SEQ ID NO: 825) CAAACTCACAAATACTTTACAATTC (SEQ ID NO: 826) | 478 |
| 17 | CDKN1B (SEQ ID NO: 18) | GTGGGGAGGTAGTTGAAGA (SEQ ID NO: 827) ATACACCCCTAACCCAAAAT (SEQ ID NO: 828) | 478 |
| 18 | CDKN2A (SEQ ID NO: 19) | TTGAAAATTAAGGGTTGAGG (SEQ ID NO: 829) CACCCTCTAATAACCAACCA (SEQ ID NO: 830) | 598 |
| 19 | CDKN2A (SEQ ID NO: 19) | GGGGTTGGTTGGTTATTAGA (SEQ ID NO: 831) AACCCTCTACCCACCTAAAT (SEQ ID NO: 832) | 256 |
| 20 | CDKN2B (SEQ ID NO: 20) | GGTTGGTTGAAGGAATAGAAAT (SEQ ID NO: 833) CCCACTAAACATACCCTTATTC (SEQ ID NO: 834) | 708 |
| 21 | CD44 (SEQ ID NO: 21) | GAAAGGAGAGGTTAAAGGTTG (SEQ ID NO: 835) AACTCACTTAACTCCAATCCC (SEQ ID NO: 836) | 696 |
| 22 | CSPG2 (SEQ ID NO: 22) | GGATAGGAGTTGGGATTAAGAT (SEQ ID NO: 837) AAATCTTTTTCAACACCAAAAT (SEQ ID NO: 838) | 414 |
| 23 | DAPK1 (SEQ ID NO: 23) | AACCCTTTCTTCAAATTACAAA (SEQ ID NO: 839) TGATTGGGTTTTAGGGAAATA (SEQ ID NO: 840) | 348 |
| 24 | GGT1 (SEQ ID NO: 24) | GTGAAGGGTGTGAGTTGTTTA (SEQ ID NO: 841) CACAATCAATTTCCCACAA (SEQ ID NO: 842) | 562 |

TABLE 1-continued

| No. | Gene: | Primer: | Amplificate Length: |
|---|---|---|---|
| 25 | GSTP1 (SEQ ID NO: 25) | ATTTGGGAAAGAGGGAAAG (SEQ ID NO: 843) TAAAAACTCTAAACCCCATCC (SEQ ID NO: 844) | 300 |
| 26 | HIC1 (SEQ ID NO: 26) | TGGGTTGGAGAAGAAGTTTA (SEQ ID NO: 845) TCATATTTCCAAAAACACACC (SEQ ID NO: 846) | 280 |
| 27 | STMN1 (SEQ ID NO: 27) | GAGTTTGTATTTAAGTTGAGTGGTT (SEQ ID NO: 847) AACAAAACAATACCCCTTCTAA (SEQ ID NO: 848) | 334 |
| 28 | STK11 (SEQ ID NO: 28) | TAAAAGAAGGATTTTTGATTGG (SEQ ID NO: 850) CATCTTATTTACCTCCCTCCC (SEQ ID NO: 849) | 528 |
| 29 | ING4 (SEQ ID NO: 29) | ATTAGGGATGAGAGGATTTGTA (SEQ ID NO: 851) TCTTCCTAACCATACACACTAACC (SEQ ID NO: 852) | 212 |
| 30 | MGMT (SEQ ID NO: 30) | AAGGTTTTAGGGAAGAGTGTTT (SEQ ID NO: 853) ACCTTTTCCTATCACAAAAATAA (SEQ ID NO: 854) | 636 |
| 31 | MLH1 (SEQ ID NO: 31) | TAAGGGGAGAGGAGGAGTTT (SEQ ID NO: 855) ACCAATTCTCAATCATCTCTTT (SEQ ID NO: 856) | 545 |
| 32 | MYC (SEQ ID NO: 33) | AGAGGGAGTAAAAGAAAATGGT (SEQ ID NO: 857) CCAAATAAACAAAATAACCTCC (SEQ ID NO: 858) | 712 |
| 33 | N33 (SEQ ID NO: 35) | TTTTAGATTGAGGTTTTAGGGT (SEQ ID NO: 859) ATCCATTCTACCTCCTTTTTCT (SEQ ID NO: 860) | 497 |
| 34 | PAX6 (SEQ ID NO: 36) | GGAGGGGAGAGGGTTATG (SEQ ID NO: 861) TACTATACACACCCCAAAACAA (SEQ ID NO: 862) | 374 |
| 35 | X51730 PGR (SEQ ID NO: 67) | TTTGGGAATGGGTTGTAT (SEQ ID NO: 921) CTACCCTTAACCTCCATCCTA (SEQ ID NO: 922) | 369 |
| 36 | PTEN (SEQ ID NO: 38) | TTTTAGGTAGTFATATTGGGTATGTT (SEQ ID NO: 865) TCAACTCTCAAACTTCCATCA (SEQ ID NO: 866) | 346 |
| 37 | RARB (SEQ ID NO: 39) | TGTTGGGAGTTTTTAAGTTTT (SEQ ID NO: 867) CAAATTCTCCTTCCAAATAAAT (SEQ ID NO: 868) | 353 |
| 38 | SFN (SEQ ID NO: 40) | GAAGAGAGGAGAGGGAGGTA (SEQ ID NO: 870) CTATCCAACAAACCCAACA (SEQ ID NO: 869) | 489 |
| 39 | S100A2 (SEQ ID NO: 41) | GTTTTTAAGTTGGAGAAGAGGA (SEQ ID NO: 1031) ACCTATAAATCACAACCCACTC (SEQ ID NO: 1032) | 460 |

TABLE 1-continued

| No. | Gene: | Primer: | Amplificate Length: |
|---|---|---|---|
| 40 | TGFBR2 (SEQ ID NO: 43) | GTAATTTGAAGAAAGTTGAGGG (SEQ ID NO: 874) CCAACAACTAAACAAAACCTCT (SEQ ID NO: 874) | 296 |
| 41 | TIMP3 (SEQ ID NO: 44) | TGAGAAAATTGTTGTTTGAAGT (SEQ ID NO: 875) CAAAATACCCTAAAAACCACTC (SEQ ID NO: 876) | 306 |
| 42 | VHL (SEQ ID NO: 45) | TGTAAAATGAATAAAGTTAATGAGTG (SEQ ID NO: 877) TCCTAAATTCAAATAATCCTCCT (SEQ ID NO: 878) | 362 |
| 43 | CDKN1C (SEQ ID NO: 46) | GGGGAGGTAGATATTTGGATAA (SEQ ID NO: 879) AACTACACCATTTATATTCCCAC (SEQ ID NO: 880) | 300 |
| 44 | CAV1 (SEQ ID NO: 47) | GTTAGTATGTTTGGGGGTAAAT (SEQ ID NO: 882) ATAAATAACACCTTCGACCCTA (SEQ ID NO: 881) | 435 |
| 45 | CDH13 (SEQ ID NO: 48) | TTTGTATTAGGTTGGAAGTGGT (SEQ ID NO: 883) CCCAAATAAATCAACAACAACA (SEQ ID NO: 884) | 286 |
| 46 | NDRG1 (SEQ ID NO: 49) | GGTTTTGGGTTTAGTGGTAAAT (SEQ ID NO: 886) AACTTTCATAACTCACCCTTTC (SEQ ID NO: 885) | 416 |
| 47 | PTGS2 (SEQ ID NO: 50) | GATTTTTGGAGAGGAAGTTAAG (SEQ ID NO: 888) AAAACTAAAAACCAAACCCATA (SEQ ID NO: 887) | 381 |
| 48 | THBS1 (SEQ ID NO: 51) | TGGGGTTAGTTTAGGATAGG (SEQ ID NO: 889) CTTAAAAACACTAAAACTTCTCAAA (SEQ ID NO: 890) | 398 |
| 49 | TMEFF2 (SEQ ID NO: 52) | TTGTTTGGGTTAATAAATGGA (SEQ ID NO: 891) CTTCTCTCTTCTCCCCTCTG (SEQ ID NO: 892) | 295 |
| 50 | PLAU (SEQ ID NO: 53) | TATTATAGGAGGATTGAGGAGG (SEQ ID NO: 893) CCCATAAAATCATACCACTTCT (SEQ ID NO: 894) | 499 |
| 51 | TMEFF2 (SEQ ID NO: 54) | TGTTGGTTGTTGTTGTTGTT (SEQ ID NO: 1037) CTTTCTACCCATCCCAAAA (SEQ ID NO: 1038) | 319 |
| 52 | DNMT1 (SEQ ID NO: 55) | TCCCCATCACACCTAAAA (SEQ ID NO: 897) GGGAGGAGGGGATGTATT (SEQ ID NO: 898) | 210 |
| 53 | ESR1 (SEQ ID NO: 70) | AGGGGGAATTAAATAGAAAGAG (SEQ ID NO: 927) CAATAAAACCATCCCAAATACT (SEQ ID NO: 928) | 662 |
| 54 | APAF1 (SEQ ID NO: 57) | AGATATGTTTGGAGATTTTAGGA (SEQ ID NO: 901) AACTCCGCACCTCTAATTCTAT (SEQ ID NO: 902) | 674 |

TABLE 1-continued

| No. | Gene: | Primer: | Amplificate Length: |
|---|---|---|---|
| 55 | HOXA5 (SEQ ID NO: 58) | AAACCCCAAACAACCTCTAT (SEQ ID NO: 904) GAAGGGGAAAGTTATTTAGTTA (SEQ ID NO: 903) | 392 |
| 56 | RASSF1 (SEQ ID NO: 59) | ACCTCTCTACAAATTACAAATTCA (SEQ ID NO: 905) AGTTTGGGTTAGTTTGGGTT (SEQ ID NO: 906) | 347 |
| 57 | BRCA2 (SEQ ID NO: 60) | ACCCACCCAAACCTAACT (SEQ ID NO: 908) GGTTGGTAGAGATAAAAGGGTA (SEQ ID NO: 907) | 388 |
| 58 | CCND1 (SEQ ID NO: 61) | GATTATAGGGGAGTTTTGTTGA (SEQ ID NO: 909) CACCTCCAACATCCAAATA (SEQ ID NO: 910) | 404 |
| 59 | EDNRB (SEQ ID NO: 62) | TCAAAACATCCTCTATCTCTCC (SEQ ID NO: 912) ATAATTGGGGGTTGTATGTATT (SEQ ID NO: 911) | 484 |
| 60 | EGFR (SEQ ID NO: 63) | GGGTTTGGTTGTAATATGGATT (SEQ ID NO: 913) CCCAACAGTACCCCTCTAA (SEQ ID NO: 914) | 732 |
| 61 | ERBB2 (SEQ ID NO: 64) | GAGGTAGAGGTTGTGGTGAGT (SEQ ID NO: 915) TCCCAACTTCACTTTCTCC (SEQ ID NO: 916) | 528 |
| 62 | FOS (SEQ ID NO: 65) | ATCCTCCACTITITCTACTTCCA (SEQ ID NO: 918) TTTTAGGGTTATAGGGAAAGGT (SEQ ID NO: 917) | 500 |
| 63 | NFKB1 (SEQ ID NO: 66) | TTTGTAGAATGAAAAGTAGAGTGTG (SEQ ID NO: 919) ACCTTAAAAACCCCAACAAT (SEQ ID NO: 920) | 485 |
| 64 | X51730 PGR (SEQ ID NO: 67) | TTTTGGGAATGGGTTGTAT (SEQ ID NO: 921) CTACCCTTAACCTCCATCCTA (SEQ ID NO: 922) | 369 |
| 65 | TP53 (SEQ ID NO: 68) | GAGTAGGTAGTTGTTGGGTTTC (SEQ ID NO: 923) ACCCCTAATTTAACACTTCTCA (SEQ ID NO: 924) | 702 |
| 66 | TP73 (SEQ ID NO: 69) | AGTAAATAGTGGGTGAGTTATGAA (SEQ ID NO: 925) GAAAAACCTCTAAAAACTACTCTCC (SEQ ID NO: 926) | 607 |
| 67 | ESR1 (SEQ ID NO: 70) | AGGGGGAATTAAATAGAAAGAG (SEQ ID NO: 927) CAATAAAACCATCCCAAATACT (SEQ ID NO: 928) | 662 |
| 68 | SERPINE1 (SEQ ID NO: 71) | GGGGTATAGAGAGAGTTTGGAT (SEQ ID NO: 929) ACAATTAAACAAACCCCAATAA (SEQ ID NO: 930) | 492 |
| 69 | CALM1 (SEQ ID NO: 72) | AAAAACTCTAACCCTTCTCAAA (SEQ ID NO: 932) TATTTTTAGTTTGGGGTGTTGT (SEQ ID NO: 931) | 414 |

TABLE 1-continued

| No. | Gene: | Primer: | Amplificate Length: |
|---|---|---|---|
| 70 | CSNK2B (SEQ ID NO: 73) | TACCCCTCACCATTACTCTAAC (SEQ ID NO: 934) TAGTTTTGTGTTTATTGGGTGA (SEQ ID NO: 933) | 437 |
| 71 | FGFR1 (SEQ ID NO: 74) | AGGGAGTTAGTGGTGTGGTAT (SEQ ID NO: 935) CCTTTACCCTTCTCAAATCTAA (SEQ ID NO: 936) | 367 |
| 72 | MK167 (SEQ ID NO: 75) | CCAATACTCTACAACCATCAAA (SEQ ID NO: 938) GGGAAGTTGAAGTAGGAAGAT (SEQ ID NO: 937) | 499 |
| 73 | NPM1 (SEQ ID NO: 76) | AAGGAAGGAGGAAGTAATTTGT (SEQ ID NO: 939) TTACACCAACCCCTAAACTAAC (SEQ ID NO: 940) | 454 |
| 74 | MAPK1 (SEQ ID NO: 77) | TTTAGATAATTTTAGGATGGGG (SEQ ID NO: 941) TTCTCATTCACAAAAACAAAAA (SEQ ID NO: 942 | 743 |
| 75 | SYK (SEQ ID NO: 78) | GTGGGTTTTGGGTAGTTATAGA (SEQ ID NO: 1041) TAACCTCCTCTCCTTACCAA (SEQ ID NO: 1042) | 485 |
| 76 | TK2 (SEQ ID NO: 79) | ATACAACCTCAAATCCTATCCA (SEQ ID NO: 946) AGGGAGAAGGAAGTTATTTGTT (SEQ ID NO: 945) | 485 |
| 77 | HSPB1 (SEQ ID NO: 80) | CCTACCTCTACCACTTCTCAAT (SEQ ID NO: 948) AAGAGGGTTTAGTTTTTATTTGG (SEQ ID NO: 947) | 216 |
| 78 | TES (SEQ ID NO: 81) | AGGTTGGGGATTTTAGTTTTT (SEQ ID NO: 949) ACCTTCTTCACTTTATTTTCCA (SEQ ID NO: 950) | 448 |
| 79 | SDC4 (SEQ ID NO: 82) | CCTAACTACCCTCATTCCTTT (SEQ ID NO: 952) AGTTGGGGAAATTAAGGTTTAG (SEQ ID NO: 951) | 269 |
| 80 | PITX2 (SEQ ID NO: 83) | TCCTCAACTCTACAAACCTAAAA (SEQ ID NO: 1056) GTAGGGGAGGGAAGTAGATGT (SEQ ID NO: 1055) | 408 |
| 81 | GPR37 (SEQ ID NO: 84) | ACTTATTTTCTTTTGCTGTAAAAAC (SEQ ID NO: 956) TATGGTTTGGTGAGGGTATATT (SEQ ID NO: 955) | 489 |
| 82 | FGF1 (SEQ ID NO: 85) | AGTTGTGTTTAATTGGGAAGAG (SEQ ID NO: 957) CTTATCCCATCCACTATACCAT (SEQ ID NO: 958) | 420 |
| 83 | GRIN2D (SEQ ID NO: 86) | ATAGTTTGTGGTTTGGATTTTT (SEQ ID NO: 959) AAAACCTTTCCCTAACTTCAAT (SEQ ID NO: 960) | 435 |
| 84 | CTSB (SEQ ID NO: 87) | AAAATTCCATCAAATAACCATAA (SEQ ID NO: 962) AAAAAGGAAGGTAGTAGGATTGT (SEQ ID NO: 961) | 450 |

TABLE 1-continued

| No. | Gene | Primer | Amplificate Length |
|---|---|---|---|
| 85 | CTSD (SEQ ID NO: 88) | ATACAACCCTCCAACCTTCTAC (SEQ ID NO: 964) AAGGGGTTTTTAAGGAAATG (SEQ ID NO: 963) | 498 |
| 86 | PLAUR (SEQ ID NO: 89) | TGGTTAAAATGGAGGGTTTAAT (SEQ ID NO: 965) CCCCAAATTACCTAAATACAAA (SEQ ID NO: 966) | 348 |
| 87 | PSA (SEQ ID NO: 90) | TAAGAGAGAGGAGTTGAGGTTT (SEQ ID NO: 967) CCAAAATTAACCACCTACCTAA (SEQ ID NO: 968) | 478 |
| 88 | CGA (SEQ ID NO: 91) | TAGTGGTATAAGTTTGGAAATGTT (SEQ ID NO: 1047) TCCACCTACATCTAAACCCTAA (SEQ ID NO: 1048) | 364 |
| 89 | CYP2D6 (SEQ ID NO: 92) | TAAGGGTTTGGAGTAGGAAGTA (SEQ ID NO: 971) CACATACAACAAAATTACCCAA (SEQ ID NO: 972) | 403 |
| 90 | CYP3A4 (SEQ ID NO: 93) | TATCACCACCTTCCCATATTTA (SEQ ID NO: 974) GTTTGATGAATGGATTGTATGA (SEQ ID NO: 973) | 484 |
| 91 | TK1 (SEQ ID NO: 94) | ACCTCTACAAACATCTTATTCCA (SEQ ID NO: 976) TTGGGGGAGTTAGGTAGTATAG (SEQ ID NO: 975) | 487 |
| 92 | RENBP (SEQ ID NO: 95) | TTTGGTAGGGTTAAGGTTTTTA (SEQ ID NO: 977) CTTACTCATCCCTCCTACTCC (SEQ ID NO: 978) | 350 |
| 93 | F12 (SEQ ID NO: 96) | TAGGTTTAGGAGGGTAGTTTGA (SEQ ID NO: 979) CTCTCACAACCCAAAAATACA (SEQ ID NO: 980) | 450 |
| 94 | REN (SEQ ID NO: 97) | ACCTACTCCAAAAATCACAAAA (SEQ ID NO: 982) TATGTGGAAAAGTTAGGGTGTT (SEQ ID NO: 981) | 489 |
| 95 | EBAG9 (SEQ ID NO: 98) | CCAAAACTCATTAACTCCCA (SEQ ID NO: 984) AATGTTTTAGAGGTTAGGGTTG (SEQ ID NO: 983) | 463 |
| 96 | MSMB (SEQ ID NO: 99) | GTTTTGTAGGATGGTTTGATTT (SEQ ID NO: 985) TATATTTACCTTATCCCCACCC (SEQ ID NO: 986) | 324 |
| 97 | X15323 angiotensinogen gene 5' region and exon 1 (SEQ ID NO: 100) | AAACTCTCCCCTACCCTCTAC (SEQ ID NO: 988) GATGGAGTTGTTTTTAGGTTGT (SEQ ID NO: 987) | 374 |
| 98 | ZNF147 (SEQ ID NO: 101) | TTTGTGTAAATAAGATGTGGGA (SEQ ID NO: 989) TAAACCCCTACAAAACTACCAA (SEQ ID NO: 990) | 484 |
| 99 | EBBP (SEQ ID NO: 102) | GTATTTGTTTTTGGTGAGGGT (SEQ ID NO: 991) ATCATCTTCCTAAACATTCCAA (SEQ ID NO: 992) | 482 |

TABLE 1-continued

| No. | Gene: | Primer: | Amplificate Length: |
|---|---|---|---|
| 100 | CALR (SEQ ID NO: 103) | TAAATCACAACCATTAACCAAA (SEQ ID NO: 994) ATAAGAGGGGAGGAAGGTTTA (SEQ ID NO: 993) | 490 |
| 101 | BCAR1 (SEQ ID NO: 104) | AATTCTTCCTTCTATCTCCCTC (SEQ ID NO: 996) TTTATTTTTGGGAAGGTTGTT (SEQ ID NO: 995) | 499 |
| 102 | COX7A2L (SEQ ID NO: 105) | AATCCTAAAAACCCTAACTTTTAAT (SEQ ID NO: 998) GGAGGTGTAAGGAGAATAGAGA (SEQ ID NO: 997) | 398 |
| 103 | AF174646 glandular kallikrein gene, promoter region and partial sequence (SEQ ID NO: 106) | CCAATTCATCATTCAACATCTA (SEQ ID NO: 1000) ATTTATTTGGGAGGATAGTGG (SEQ ID NO: 999) | 325 |
| 104 | KLK3 (SEQ ID NO: 107) | TTGGAGTGTAAAGGATTTAGGT (SEQ ID NO: 1001) AACCCACATAATAACACAACTCT (SEQ ID NO: 1002) | 387 |
| 105 | AKR1B1 (SEQ ID NO: 108) | CAACAAAAACATTCTTCTAAACTC (SEQ ID NO: 1004) AGGTATTTAATTTTAGGATGGGT (SEQ ID NO: 1003) | 446 |
| 106 | TGM4 (SEQ ID NO: 109) | AATCCTAACTTTTAATCACCCA (SEQ ID NO: 1006) GAGAGGGTAATGGTTTTAGGTA (SEQ ID NO: 1005) | 435 |
| 107 | AR (SEQ ID NO: 110) | AATATAGGGAGGTTTAGGGTTT (SEQ ID NO: 1007) TAACCATACATTTCTCATCCAA (SEQ ID NO: 1008) | 424 |
| 108 | HSPA1A (SEQ ID NO: 111) | AACCTTTCAAATTCACAATCA (SEQ ID NO: 1010) GGATTTATTGGAGGGGATAG (SEQ ID NO: 1009) | 495 |
| 109 | FKBP4 (SEQ ID NO: 112) | TTTTTAAGTAGGGAAGGGTTT (SEQ ID NO: 1011) TCCTTCTAACTACCTACCCCC (SEQ ID NO: 1012) | 308 |
| 110 | ESR2 (SEQ ID NO: 113) | AAACCTTCCCAATAACCTCTTA (SEQ ID NO: 1014) TAGAGGGGAGTAGTGTTTGAGT (SEQ ID NO: 1013) | 471 |
| 111 | IGF1 (SEQ ID NO: 114) | TACCCTTCTCCCAAAATAATAA (SEQ ID NO: 1016) GTATTAAAGGAATATGGGGAT (SEQ ID NO: 1015) | 402 |
| 112 | VTN (SEQ ID NO: 115) | GTTATTTGGGTTAATGTAGGGA (SEQ ID NO: 1017) TCTATCCCCTCAAACTTAAAAA (SEQ ID NO: 1018) | 492 |
| 113 | CTSL (SEQ ID NO: 116) | CTACACCCACCCTTAAATAAAA (SEQ ID NO: 1020) TTAGTGGATTTGGAGGAAGTAG (SEQ ID NO: 1019) | 328 |
| 114 | TGFB3 (SEQ ID NO: 117) | CCTACTAAAAATCAAAACCCAA (SEQ ID NO: 1022) AAGGTGGTGTAAGTGGATAGAG (SEQ ID NO: 1021) | 369 |

TABLE 1-continued

| No. | Gene: | Primer: | Amplificate Length: |
|---|---|---|---|
| 115 | MAPKAPK5 (SEQ ID NO: 118) | AAACCTACCTCCCCAACTAA (SEQ ID NO: 1024) ATTTTTGGTTTTAGGGTTGTAA (SEQ ID NO: 1023) | 495 |
| 116 | PCAF (SEQ ID NO: 119) | GGATAAATGATTGAGAGGTTGT (SEQ ID NO: 1057) CCTCCCTTAATTCTCCTACC (SEQ ID NO: 1058) | 369 |
| 117 | NCOA3 (SEQ ID NO: 120) | AAGGGGGTGTTTGTTAGATT (SEQ ID NO: 1027) CCTAACCCTACCCTTAATTTTT (SEQ ID NO: 1028) | 330 |
| 118 | PRKCD (SEQ ID NO: 121) | CTTAACCCATCCCAATCA (SEQ ID NO: 1030) GATAGAAGGATTTTAGTTTTTATTGTT (SEQ ID NO: 1029) | 322 |
| 119 | S100A2 (SEQ ID NO: 41) | GTTTTTAAGTTGGAGAAGAGGA (SEQ ID NO: 1031) ACCTATAAATCACAACCCACTC (SEQ ID NO: 1032) | 460 |
| 120 | PSA (SEQ ID NO: 90) | GTAGGTGGTTAATTTTGGGTT (SEQ ID NO: 1033) CTCATTCACACTATATCCATTCA (SEQ ID NO: 1034) | 500 |
| 121 | ESR1 (SEQ ID NO: 70) | CTATCAATTCCCCCAACTACT (SEQ ID NO: 1036) TTGTTGGATAGAGGTTGAGTTT (SEQ ID NO: 1035) | 349 |
| 122 | TMEFF2 (SEQ ID NO: 54) | TGTTGGTTGTTGTTGTTGTT (SEQ ID NO: 1037) CTTTCTACCCATCCCAAAA (SEQ ID NO: 1038) | 319 |
| 123 | TP53 (SEQ ID NO: 68) | TTGATGAGAAGAAAGGATTTAGT (SEQ ID NO: 1039) TCAAATTCAATCAAAAACTTACC (SEQ ID NO: 1040) | 496 |
| 124 | SYK (SEQ ID NO: 78) | GTGGGTTTTGGGTAGTTATAGA (SEQ ID NO: 1041) TAACCTCCTCTCCTTACCAA (SEQ ID NO: 1042) | 485 |
| 125 | DAG1 (SEQ ID NO: 125) | AATACCAACCCAAACATCTACC (SEQ ID NO: 1044) TTTGGTTATGTGGAGTTTATTGT (SEQ ID NO: 1043) | 315 |
| 126 | ONECUT2 (SEQ ID NO: 126) | TTTGTTGGGATTTGTTAGGAT (SEQ ID NO: 1045) AAACATTTTACCCCTCTAAACC (SEQ ID NO: 1046) | 467 |
| 127 | CGA (SEQ ID NO: 91) | TAGTGGTATAAGTTTGGAAATGTT (SEQ ID NO: 1047) TCCACCTACATCTAAACCCTAA (SEQ ID NO: 1048) | 364 |
| 128 | CYP2D6 (SEQ ID NO: 129) | AATTTCCTAACCCACTATCCTC (SEQ ID NO: 1050) ATTTGTAGTTTGGGGTGATTT (SEQ ID NO: 1049) | 379 |
| 129 | RASSF1 (SEQ ID NO: 59) | AGTGGGTAGGTTAAGTGTGTTG (SEQ ID NO: 1051) CCCCAAAATCCAAACTAAA (SEQ ID NO: 1052) | 319 |

TABLE 1-continued

| No. | Gene: | Primer: | Amplificate Length: |
|---|---|---|---|
| 130 | ERBB2 (SEQ ID NO: 64) | GGAGGGGGTAGAGTTATTAGTT (SEQ ID NO: 1053) TATACTTCCTCAAACAACCCTC (SEQ ID NO: 1054) | 258 |
| 131 | PITX2 (SEQ ID NO: 83) | TCCTCAACTCTACAAACCTAAAA (SEQ ID NO: 1056) GTAGGGGAGGGAAGTAGATGT (SEQ ID NO: 1055) | 408 |
| 132 | PCAF (SEQ ID NO: 119) | GGATAAATGATTGAGAGGTTGT (SEQ ID NO: 1057) CCTCCCTTAATTCTCCTACC (SEQ ID NO: 1058) | 369 |
| 133 | WBP11 (SEQ ID NO: 137) | AAGAGGTGAGGAAGAGTAGTAAAT (SEQ ID NO: 1059) CTCCCAACAACTAAATCAAAAT (SEQ ID NO: 1060) | 437 |

TABLE 2

| NO: | Gene | Oligo: |
|---|---|---|
| 1 | STMN1 (SEQ ID NO: 27) | GTTATCGGTTCGGGAATT (SEQ ID NO: 2001) |
| 2 | STMN1 (SEQ ID NO: 27) | GTTATTGGTTTGGGAATT (SEQ ID NO: 2002) |
| 3 | STMN1 (SEQ ID NO: 27) | GTTATCGGTTCGGGAATT (SEQ ID NO: 2001) |
| 4 | STMN1 (SEQ ID NO: 27) | GTTATTGGTTTGGGAATT (SEQ ID NO: 2002) |
| 5 | STMN1 (SEQ ID NO: 27) | GTAAGAACGTATATAGTGAG (SEQ ID NO: 2003) |
| 6 | STMN1 (SEQ ID NO: 27) | GTAAGAATGTATATAGTGAG (SEQ ID NO: 2004) |
| 7 | STMN1 (SEQ ID NO: 27) | GTAAGAACGTATATAGTGAG (SEQ ID NO: 2003) |
| 8 | STMN1 (SEQ ID NO: 27) | GTAAGAATGTATATAGTGAG (SEQ ID NO: 2004) |
| 9 | STMN1 (SEQ ID NO: 27) | AGAAATTACGATGATGTTAT (SEQ ID NO: 2005) |
| 10 | STMN1 (SEQ ID NO: 27) | AGAAATTATGATGATGTTAT (SEQ ID NO: 2006) |
| 11 | STMN1 (SEQ ID NO: 27) | AGAAATTACGATGATGTTAT (SEQ ID NO: 2005) |
| 12 | STMN1 (SEQ ID NO: 27) | AGAAATTATGATGATGTTAT (SEQ ID NO: 2006) |
| 13 | STMN1 (SEQ ID NO: 27) | ATGGGTGATACGTCGGTG (SEQ ID NO: 2007) |
| 14 | STMN1 (SEQ ID NO: 27) | ATGGGTGATATGTTGGTG (SEQ ID NO: 2008) |
| 15 | STMN1 (SEQ ID NO: 27) | ATGGGTGATACGTCGGTG (SEQ ID NO: 2007) |
| 16 | STMN1 (SEQ ID NO: 27) | ATGGGTGATATGTTGGTG (SEQ ID NO: 2008) |
| 17 | PSA (SEQ ID NO: 90) | TTTCGATTCGGTTTAGA (SEQ ID NO: 2009) |
| 18 | PSA (SEQ ID NO: 90) | AATTGTTTTGATTTGGTT (SEQ ID NO: 2010) |
| 19 | PSA (SEQ ID NO: 90) | TAATGGGGCGTCGATT (SEQ ID NO: 2011) |
| 20 | PSA (SEQ ID NO: 90) | TTAATGGGGTGTTGATT (SEQ ID NO: 2012) |
| 21 | PSA (SEQ ID NO: 90) | TATCGTAGCGGTTAGG (SEQ ID NO: 2013) |
| 22 | PSA (SEQ ID NO: 90) | TATTGTAGTGGTTAGGAA (SEQ ID NO: 2014) |
| 23 | PSA (SEQ ID NO: 90) | AGGAACGTTAGTCGTT (SEQ ID NO: 2015) |
| 24 | PSA (SEQ ID NO: 90) | TAGGAATGTTAGTTGTTT (SEQ ID NO: 2016) |
| 25 | PSA (SEQ ID NO: 90) | GGTCGTCGTATTATGGA (SEQ ID NO: 2017) |
| 26 | PSA (SEQ ID NO: 90) | TGGTTGTTGTATTATGGA (SEQ ID NO: 2018) |
| 27 | CGA (SEQ ID NO: 91) | TAAATTGACGTTATGGTA (SEQ ID NO: 2019) |
| 28 | CGA (SEQ ID NO: 91) | AAAATTGATGTTATGGTAAA (SEQ ID NO: 2020) |
| 29 | CGA (SEQ ID NO: 91) | AATTGACGTTATGGTAAT (SEQ ID NO: 2021) |
| 30 | CGA (SEQ ID NO: 91) | TAAAAATTGATGTTATGGT (SEQ ID NO: 2022) |
| 31 | PITX2 (SEQ ID NO: 83) | AGTCGGGAGAGCGAAA (SEQ ID NO: 2023) |
| 32 | PITX2 (SEQ ID NO: 83) | AGTTGGGAGAGTGAAA (SEQ ID NO: 2024) |
| 33 | PITX2 (SEQ ID NO: 83) | AGTCGGGAGAGCGAAA (SEQ ID NO: 2023) |

TABLE 2-continued

| NO: | Gene | Oligo: |
|---|---|---|
| 34 | PITX2 (SEQ ID NO: 83) | AGTTGGGAGAGTGAAA (SEQ ID NO: 2024) |
| 35 | PITX2 (SEQ ID NO: 83) | AAGAGTCGGGAGTCGGA (SEQ ID NO: 2025) |
| 36 | PITX2 (SEQ ID NO: 83) | AAGAGTTGGGAGTTGGA (SEQ ID NO: 2026) |
| 37 | PITX2 (SEQ ID NO: 83) | AAGAGTCGGGAGTCGGA (SEQ ID NO: 2025) |
| 38 | PITX2 (SEQ ID NO: 83) | AAGAGTTGGGAGTTGGA (SEQ ID NO: 2026) |
| 39 | PITX2 (SEQ ID NO: 83) | GGTCGAAGAGTCGGGA (SEQ ID NO: 2027) |
| 40 | PITX2 (SEQ ID NO: 83) | GGTTGAAGAGTTGGGA (SEQ ID NO: 2028) |
| 41 | PITX2 (SEQ ID NO: 83) | GGTCGAAGAGTCGGGA (SEQ ID NO: 2027) |
| 42 | PITX2 (SEQ ID NO: 83) | GGTTGAAGAGTTGGGA (SEQ ID NO: 2028) |
| 43 | FGFR1 (SEQ ID NO: 74) | GTATTTCGTTGGTTAAGT (SEQ ID NO: 2029) |
| 44 | FGFR1 (SEQ ID NO: 74) | GTGTATTTTGTTGGTTAA (SEQ ID NO: 2030) |
| 45 | FGFR1 (SEQ ID NO: 74) | ATGTGAACGAAGTTAAG (SEQ ID NO: 2031) |
| 46 | FGFR1 (SEQ ID NO: 74) | ATGTGAATGAAGTTAAGA (SEQ ID NO: 2032) |
| 47 | PSA (SEQ ID NO: 90) | TTTCGATTCGGTTTAGA (SEQ ID NO: 2009) |
| 48 | PSA (SEQ ID NO: 90) | AATTGTTTTGATTTGGTT (SEQ ID NO: 2010) |
| 49 | PSA (SEQ ID NO: 90) | AGGAACGTTAGTGGTT (SEQ ID NO: 2015) |
| 50 | PSA (SEQ ID NO: 90) | TAGGAATGTTAGTTGTTT (SEQ ID NO: 2016) |
| 51 | PSA (SEQ ID NO: 90) | GGTCGTCGTATTATGGA (SEQ ID NO: 2017) |
| 52 | PSA (SEQ ID NO: 90) | TGGTTGTTGTATTATGGA (SEQ ID NO: 2018) |
| 53 | CGA (SEQ ID NO: 91) | TAAATTGACGTTATGGTA (SEQ ID NO: 2019) |
| 54 | CGA (SEQ ID NO: 91) | AAATTGATGTTATGGTAAA (SEQ ID NO: 2020) |
| 55 | CGA (SEQ ID NO: 91) | AATTGACGTTATGGTAAT (SEQ ID NO: 2021) |
| 56 | CGA (SEQ ID NO: 91) | TAAAAATTGATGTTATGGT (SEQ ID NO: 2022) |
| 57 | PTGS2 (SEQ ID NO: 50) | TTTATCGGGTTTACGTAATT (SEQ ID NO: 2033) |
| 58 | PTGS2 (SEQ ID NO: 50) | TTTATTGGGTTTATGTAATT (SEQ ID NO: 2034) |
| 59 | PTGS2 (SEQ ID NO: 50) | TTTATCGGGTTTACGTAATT (SEQ ID NO: 2033) |
| 60 | PTGS2 (SEQ ID NO: 50) | TTTATTGGGTTTATGTAATT (SEQ ID NO: 2034) |
| 61 | PTGS2 (SEQ ID NO: 50) | GTACGAAAAGGCGGAAAG (SEQ ID NO: 2035) |
| 62 | PTGS2 (SEQ ID NO: 50) | GTATGAAAAGGTGGAAAG (SEQ ID NO: 2036) |
| 63 | PTGS2 (SEQ ID NO: 50) | GTACGAAAAGGCGGAAAG (SEQ ID NO: 2035) |
| 64 | PTGS2 (SEQ ID NO: 50) | GTATGAAAAGGTGGAAAG (SEQ ID NO: 2036) |
| 65 | MSMB (SEQ ID NO: 99) | ATAGGGCGAAGGTTTA (SEQ ID NO: 2037) |
| 66 | MSMB (SEQ ID NO: 99) | ATAGGGTGAAGGTTTAG (SEQ ID NO: 2038) |
| 67 | TP53 (SEQ ID NO: 68) | TTTTTACGACGGTGAT (SEQ ID NO: 2039) |
| 68 | TP53 (SEQ ID NO: 68) | TGTTTTTTATGATGGTGA (SEQ ID NO: 2040) |
| 69 | CYP2D6 (SEQ ID NO: 92) | AAGTAGCGGTAAGGAT (SEQ ID NO: 2041) |
| 70 | CYP2D6 (SEQ ID NO: 92) | GAAGTAGTGGTAAGGAT (SEQ ID NO: 2042) |
| 71 | STMN1 (SEQ ID NO: 27) | GTTATCGGTTCGGGAATT (SEQ ID NO: 2001) |
| 72 | STMN1 (SEQ ID NO: 27) | GTTATTGGTTTGGGAATT (SEQ ID NO: 2002) |
| 73 | STMN1 (SEQ ID NO: 27) | GTTATCGGTTCGGGAATT (SEQ ID NO: 2001) |
| 74 | STMN1 (SEQ ID NO: 27) | GTTATTGGTTTGGGAATT (SEQ ID NO: 2002) |
| 75 | STMN1 (SEQ ID NO: 27) | GTAAGAACGTATATAGTGAG (SEQ ID NO: 2003) |
| 76 | STMN1 (SEQ ID NO: 27) | GTAAGAATGTATATAGTGAG (SEQ ID NO: 2004) |
| 77 | STMN1 (SEQ ID NO: 27) | GTAAGAACGTATATAGTGAG (SEQ ID NO: 2003) |
| 78 | STMN1 (SEQ ID NO: 27) | GTAAGAATGTATATAGTGAG (SEQ ID NO: 2004) |
| 79 | STMN1 (SEQ ID NO: 27) | AGAAATTACGATGATGTTAT (SEQ ID NO: 2005) |
| 80 | STMN1 (SEQ ID NO: 27) | AGAAATTATGATGATGTTAT (SEQ ID NO: 2006) |
| 81 | STMN1 (SEQ ID NO: 27) | AGAAATTACGATGATGTTAT (SEQ ID NO: 2005) |
| 82 | STMN1 (SEQ ID NO: 27) | AGAAATTATGATGATGTTAT (SEQ ID NO: 2006) |
| 83 | STMN1 (SEQ ID NO: 27) | ATGGGTGATACGTCGGTG (SEQ ID NO: 2007) |
| 84 | STMN1 (SEQ ID NO: 27) | ATGGGTGATATGTTGGTG (SEQ ID NO: 2008) |
| 85 | STMN1 (SEQ ID NO: 27) | ATGGGTGATACGTCGGTG (SEQ ID NO: 2007) |

TABLE 2-continued

| NO: | Gene | Oligo: |
|---|---|---|
| 86 | STMN1 (SEQ ID NO: 27) | ATGGGTGATATGTTGGTG (SEQ ID NO: 2008) |
| 87 | PSA (SEQ ID NO: 90) | TTTCGATTCGGTTTAGA (SEQ ID NO: 2009) |
| 88 | PSA (SEQ ID NO: 90) | AATTGTTTTGATTTGGTT (SEQ ID NO: 2010) |
| 89 | PSA (SEQ ID NO: 90) | TAATGGGGCGTCGATT (SEQ ID NO: 2011) |
| 90 | PSA (SEQ ID NO: 90) | TTAATGGGGTGTTGATT (SEQ ID NO: 2012) |
| 91 | PSA (SEQ ID NO: 90) | TATCGTAGCGGTTAGG (SEQ ID NO: 2013) |
| 92 | PSA (SEQ ID NO: 90) | TATTGTAGTGGTTAGGAA (SEQ ID NO: 2014) |
| 93 | PSA (SEQ ID NO: 90) | AGGAACGTTAGTCGTTT (SEQ ID NO: 2015) |
| 94 | PSA (SEQ ID NO: 90) | TAGGAATGTTAGTTGTTT (SEQ ID NO: 2016) |
| 95 | PSA (SEQ ID NO: 90) | GGTCGTCGTATTATGGA (SEQ ID NO: 2017) |
| 96 | PSA (SEQ ID NO: 90) | TGGTTGTTGTATTATGGA (SEQ ID NO: 2018) |
| 97 | S100A2 (SEQ ID NO: 41) | TTTAATTGCGGTTGTGTG (SEQ ID NO: 2043) |
| 98 | S100A2 (SEQ ID NO: 41) | TTTAATTGTGGTTGTGTG (SEQ ID NO: 2044) |
| 99 | S100A2 (SEQ ID NO: 41) | TTTAATTGCGGTTGTGTG (SEQ ID NO: 2043) |
| 100 | S100A2 (SEQ ID NO: 41) | TTTAATTGTGGTTGTGTG (SEQ ID NO: 2044) |
| 101 | S100A2 (SEQ ID NO: 41) | TATATAGGCGTATGTATG (SEQ ID NO: 2045) |
| 102 | S100A2 (SEQ ID NO: 41) | TATATAGGTGTATGTATG (SEQ ID NO: 2046) |
| 103 | S100A2 (SEQ ID NO: 41) | TATATAGGCGTATGTATG (SEQ ID NO: 2045) |
| 104 | S100A2 (SEQ ID NO: 41) | TATATAGGTGTATGTATG (SEQ ID NO: 2046) |
| 105 | S100A2 (SEQ ID NO: 41) | TATGTATACGAGTATTGGAT (SEQ ID NO: 2047) |
| 106 | S100A2 (SEQ ID NO: 41) | TATGTATATGAGTATTGGAT (SEQ ID NO: 2048) |
| 107 | S100A2 (SEQ ID NO: 41) | TATGTATACGAGTATTGGAT (SEQ ID NO: 2047) |
| 108 | S100A2 (SEQ ID NO: 41) | TATGTATATGAGTATTGGAT (SEQ ID NO: 2048) |
| 109 | S100A2 (SEQ ID NO: 41) | AGTTTTAGCGTGTGTTTA (SEQ ID NO: 2049) |
| 110 | S100A2 (SEQ ID NO: 41) | AGTTTTAGTGTGTGTTTA (SEQ ID NO: 2050) |
| 111 | S100A2 (SEQ ID NO: 41) | AGTTTTAGCGTGTGTTTA (SEQ ID NO: 2049) |
| 112 | S100A2 (SEQ ID NO: 41) | AGTTTTAGTGTGTGTTTA (SEQ ID NO: 2050) |
| 113 | SFN (SEQ ID NO: 40) | GAGTAGGTCGAACGTTAT (SEQ ID NO: 2051) |
| 114 | SFN (SEQ ID NO: 40) | GAGTAGGTTGAATGTTAT (SEQ ID NO: 2052) |
| 115 | SFN (SEQ ID NO: 40) | GAGTAGGTCGAACGTTAT (SEQ ID NO: 2051) |
| 116 | SFN (SEQ ID NO: 40) | GAGTAGGTTGAATGTTAT (SEQ ID NO: 2052) |
| 117 | SFN (SEQ ID NO: 40) | TTTGCGAAGAGCGAAATT (SEQ ID NO: 2053) |
| 118 | SFN (SEQ ID NO: 40) | TTTGTGAAGAGTGAAATT (SEQ ID NO: 2054) |
| 119 | SFN (SEQ ID NO: 40) | TTTGCGAAGAGCGAAATT (SEQ ID NO: 2053) |
| 120 | SFN (SEQ ID NO: 40) | TTTGTGAAGAGTGAAATT (SEQ ID NO: 2054) |
| 121 | SFN (SEQ ID NO: 40) | TAACGAGGAGGGTTCGGA (SEQ ID NO: 2055) |
| 122 | SFN (SEQ ID NO: 40) | TAATGAGGAGGGTTTGGA (SEQ ID NO: 2056) |
| 123 | SFN (SEQ ID NO: 40) | TAACGAGGAGGGTTCGGA (SEQ ID NO: 2055) |
| 124 | SFN (SEQ ID NO: 40) | TAATGAGGAGGGTTTGGA (SEQ ID NO: 2056) |
| 125 | SFN (SEQ ID NO: 40) | GTTCGAGGTGCGTGAGTA (SEQ ID NO: 2057) |
| 126 | SFN (SEQ ID NO: 40) | GTTTGAGGTGTGTGAGTA (SEQ ID NO: 2058) |
| 127 | SFN (SEQ ID NO: 40) | GTTCGAGGTGCGTGAGTA (SEQ ID NO: 2057) |
| 128 | SFN (SEQ ID NO: 40) | GTTTGAGGTGTGTGAGTA (SEQ ID NO: 2058) |
| 129 | PRKCD (SEQ ID NO: 121) | ATTTATTTTTCGTTGTAGG (SEQ ID NO: 2059) |
| 130 | PRKCD (SEQ ID NO: 121) | TATTTATTTTTTGTTGTAGG (SEQ ID NO: 2060) |
| 131 | PRKCD (SEQ ID NO: 121) | TTTCGGAAACGGGAAT (SEQ ID NO: 2061) |
| 132 | PRKCD (SEQ ID NO: 121) | TAGTTTTGGAAATGGGA (SEQ ID NO: 2062) |
| 133 | PRKCD (SEQ ID NO: 121) | GGACGGAGTTATCGGT (SEQ ID NO: 2063) |
| 134 | PRKCD (SEQ ID NO: 121) | GGATGGAGTTATTGGTA (SEQ ID NO: 2064) |
| 135 | PRKCD (SEQ ID NO: 121) | GTTTAGCGGAGGGATA (SEQ ID NO: 2065) |
| 136 | PRKCD (SEQ ID NO: 121) | TGTTTAGTGGAGGGAT (SEQ ID NO: 2066) |
| 137 | SYK (SEQ ID NO: 78) | GAAGTTATCGCGTTGG (SEQ ID NO: 2067) |

TABLE 2-continued

| NO: | Gene | Oligo: |
|---|---|---|
| 138 | SYK (SEQ ID NO: 78) | AGAAGTTATTGTGTTGG (SEQ ID NO: 2068) |
| 139 | SYK (SEQ ID NO: 78) | GATCGATGCGGTTTAT (SEQ ID NO: 2069) |
| 140 | SYK (SEQ ID NO: 78) | GGGATTGATGTGGTTTA (SEQ ID NO: 2070) |
| 141 | SYK (SEQ ID NO: 78) | GTTCGGCGGGAGGAGA (SEQ ID NO: 2071) |
| 142 | SYK (SEQ ID NO: 78) | GTTTGGTGGGAGGAGA (SEQ ID NO: 2072) |
| 143 | SYK (SEQ ID NO: 78) | GTTCGGCGGGAGGAGA (SEQ ID NO: 2071) |
| 144 | SYK (SEQ ID NO: 78) | GTTTGGTGGGAGGAGA (SEQ ID NO: 2072) |
| 145 | SYK (SEQ ID NO: 78) | AGTCGATTTTCGTTTAG (SEQ ID NO: 2073) |
| 146 | SYK (SEQ ID NO: 78) | TAGTTGATTTTTGTTTAGT (SEQ ID NO: 2074) |
| 147 | SYK (SEQ ID NO: 78) | GGAAGAGTCGCGGGTT (SEQ ID NO: 2075) |
| 148 | SYK (SEQ ID NO: 78) | GGAAGAGTTGTGGGTT (SEQ ID NO: 2076) |
| 149 | SYK (SEQ ID NO: 78) | GGAAGAGTCGCGGGTT (SEQ ID NO: 2075) |
| 150 | SYK (SEQ ID NO: 78) | GGAAGAGTTGTGGGTT (SEQ ID NO: 2076) |
| 151 | VTN (SEQ ID NO: 115) | GGTGGTATCGATTGAT (SEQ ID NO: 2077) |
| 152 | VTN (SEQ ID NO: 115) | TGGTGGTATTGATTGAT (SEQ ID NO: 2078) |
| 153 | VTN (SEQ ID NO: 115) | TAGTGATTCGCGGGGA (SEQ ID NO: 2079) |
| 154 | VTN (SEQ ID NO: 115) | TAGTGATTTGTGGGGA (SEQ ID NO: 2080) |
| 155 | VTN (SEQ ID NO: 115) | TAGTGATTCGCGGGGA (SEQ ID NO: 2079) |
| 156 | VTN (SEQ ID NO: 115) | TAGTGATTTGTGGGGA (SEQ ID NO: 2080) |
| 157 | VTN (SEQ ID NO: 115) | TTATGTCGGAGGATGA (SEQ ID NO: 2081) |
| 158 | VTN (SEQ ID NO: 115) | ATTATGTTGGAGGATGA (SEQ ID NO: 2082) |
| 159 | VTN (SEQ ID NO: 115) | ATACGGTTTATGACGAT (SEQ ID NO: 2083) |
| 160 | VTN (SEQ ID NO: 115) | ATATGGTTTATGATGATGG (SEQ ID NO: 2084) |
| 161 | GRIN2D (SEQ ID NO: 86) | GAGAGTCGGGATGATT (SEQ ID NO: 2085) |
| 162 | GRIN2D (SEQ ID NO: 86) | GGAGAGTTGGGATGAT (SEQ ID NO: 2086) |
| 163 | GRIN2D (SEQ ID NO: 86) | AGAGATTTCGATTTGGA (SEQ ID NO: 2087) |
| 164 | GRIN2D (SEQ ID NO: 86) | AAGAGATTTTGATTTGGA (SEQ ID NO: 2088) |
| 165 | GRIN2D (SEQ ID NO: 86) | TAGGGTCGAGATTTGG (SEQ ID NO: 2089) |
| 166 | GRIN2D (SEQ ID NO: 86) | TTAGGGTTGAGATTTGG (SEQ ID NO: 2090) |
| 167 | GRIN2D (SEQ ID NO: 86) | AGTGTGGCGAATATTG (SEQ ID NO: 2091) |
| 168 | GRIN2D (SEQ ID NO: 86) | GTGTGGTGAATATTGAA (SEQ ID NO: 2092) |
| 169 | TGFBR2 (SEQ ID NO: 43) | GAAAACGTGGACGTTTTT (SEQ ID NO: 2093) |
| 170 | TGFBR2 (SEQ ID NO: 43) | GAAAATGTGGATGTTTTT (SEQ ID NO: 2094) |
| 171 | TGFBR2 (SEQ ID NO: 43) | GAAAACGTGGACGTTTTT (SEQ ID NO: 2093) |
| 172 | TGFBR2 (SEQ ID NO: 43) | GAAAATGTGGATGTTTTT (SEQ ID NO: 2094) |
| 173 | TGFBR2 (SEQ ID NO: 43) | ATTTGGAGCGAGGAATTT (SEQ ID NO: 2095) |
| 174 | TGFBR2 (SEQ ID NO: 43) | ATTTGGAGTGAGGAATTT (SEQ ID NO: 2096) |
| 175 | TGFBR2 (SEQ ID NO: 43) | ATTTGGAGCGAGGAATTT (SEQ ID NO: 2095) |
| 176 | TGFBR2 (SEQ ID NO: 43) | ATTTGGAGTGAGGAATTT (SEQ ID NO: 2096) |
| 177 | TGFBR2 (SEQ ID NO: 43) | AGTTGAAAGTCGGTTAAA (SEQ ID NO: 2097) |
| 178 | TGFBR2 (SEQ ID NO: 43) | AGTTGAAAGTTGGTTAAA (SEQ ID NO: 2098) |
| 179 | TGFBR2 (SEQ ID NO: 43) | AGTTGAAAGTCGGTTAAA (SEQ ID NO: 2097) |
| 180 | TGFBR2 (SEQ ID NO: 43) | AGTTGAAAGTTGGTTAAA (SEQ ID NO: 2098) |
| 181 | TGFBR2 (SEQ ID NO: 43) | AAAGTTTTCGGAGGGGTT (SEQ ID NO: 2099) |
| 182 | TGFBR2 (SEQ ID NO: 43) | AAAGTTTTTGGAGGGGTT (SEQ ID NO: 2100) |
| 183 | TGFBR2 (SEQ ID NO: 43) | AAAGTTTTCGGAGGGGTT (SEQ ID NO: 2099) |
| 184 | TGFBR2 (SEQ ID NO: 43) | AAAGTTTTTGGAGGGGTT (SEQ ID NO: 2100) |
| 185 | TGFBR2 (SEQ ID NO: 43) | GGTAGTTACGAGAGAGTT (SEQ ID NO: 2101) |
| 186 | TGFBR2 (SEQ ID NO: 43) | GGTAGTTATGAGAGAGTT (SEQ ID NO: 2102) |
| 187 | TGFBR2 (SEQ ID NO: 43) | GGTAGTTACGAGAGAGTT (SEQ ID NO: 2101) |
| 188 | TGFBR2 (SEQ ID NO: 43) | GGTAGTTATGAGAGAGTT (SEQ ID NO: 2102) |
| 189 | COX7A2L (SEQ ID NO: 105) | TTGTTCGAAGATCGTT (SEQ ID NO: 2103) |

TABLE 2-continued

| NO: | Gene | Oligo: |
|---|---|---|
| 190 | COX7A2L (SEQ ID NO: 105) | GTTGTTTGAAGATTGTTT (SEQ ID NO: 2104) |
| 191 | COX7A2L (SEQ ID NO: 105) | TAGCGTAAGGATTCGGT (SEQ ID NO: 2105) |
| 192 | COX7A2L (SEQ ID NO: 105) | TTAGTGTAAGGATTTGGT (SEQ ID NO: 2106) |
| 193 | COX7A2L (SEQ ID NO: 105) | AGAGTTCGGTTTTTCGTA (SEQ ID NO: 2107) |
| 194 | COX7A2L (SEQ ID NO: 105) | AGAGTTTGGTTTTTTGTA (SEQ ID NO: 2108) |
| 195 | COX7A2L (SEQ ID NO: 105) | AGAGTTCGGTTTTTCGTA (SEQ ID NO: 2107) |
| 196 | COX7A2L (SEQ ID NO: 105) | AGAGTTTGGTTTTTTGTA (SEQ ID NO: 2108) |
| 197 | COX7A2L (SEQ ID NO: 105) | ATTCGTATTTGCGGGTTA (SEQ ID NO: 2109) |
| 198 | COX7A2L (SEQ ID NO: 105) | ATTTGTATTTGTGGGTTA (SEQ ID NO: 2110) |
| 199 | COX7A2L (SEQ ID NO: 105) | ATTCGTATTTGCGGGTTA (SEQ ID NO: 2109) |
| 200 | COX7A2L (SEQ ID NO: 105) | ATTTGTATTTGTGGGTTA (SEQ ID NO: 2110) |
| 201 | DAG1 (SEQ ID NO: 125) | TTTCGTGGCGGAGAAT (SEQ ID NO: 2111) |
| 202 | DAG1 (SEQ ID NO: 125) | TTTTGTGGTGGAGAAT (SEQ ID NO: 2112) |
| 203 | DAG1 (SEQ ID NO: 125) | TTTCGTGGCGGAGAAT (SEQ ID NO: 2111) |
| 204 | DAG1 (SEQ ID NO: 125) | TTTTGTGGTGGAGAAT (SEQ ID NO: 2112) |
| 205 | DAG1 (SEQ ID NO: 125) | TACGGATATTTCGGTT (SEQ ID NO: 2113) |
| 206 | DAG1 (SEQ ID NO: 125) | AATTATGGATATTTTGGTT (SEQ ID NO: 2114) |
| 207 | DAG1 (SEQ ID NO: 125) | TTACGATTCGTAGGTT (SEQ ID NO: 2115) |
| 208 | DAG1 (SEQ ID NO: 125) | TATTATTATGATTTGTAGGT (SEQ ID NO: 2116) |
| 209 | ONECUT2 (SEQ ID NO: 126) | TACGTAGTTGCGCGTT (SEQ ID NO: 2117) |
| 210 | ONECUT2 (SEQ ID NO: 126) | GTATGTAGTTGTGTGTT (SEQ ID NO: 2118) |
| 211 | ONECUT2 (SEQ ID NO: 126) | TTTTGTGCGTACGGAT (SEQ ID NO: 2119) |
| 212 | ONECUT2 (SEQ ID NO: 126) | TTTTTGTGTGTATGGAT (SEQ ID NO: 2120) |
| 213 | ONECUT2 (SEQ ID NO: 126) | TTAAGCGGGCGTTGAT (SEQ ID NO: 2121) |
| 214 | ONECUT2 (SEQ ID NO: 126) | TTAAGTGGGTGTTGAT (SEQ ID NO: 2122) |
| 215 | ONECUT2 (SEQ ID NO: 126) | TTAAGCGGGCGTTGAT (SEQ ID NO: 2121) |
| 216 | ONECUT2 (SEQ ID NO: 126) | TTAAGTGGGTGTTGAT (SEQ ID NO: 2122) |
| 217 | ONECUT2 (SEQ ID NO: 126) | TAGAGGCGCGGGTTAT (SEQ ID NO: 2123) |
| 218 | ONECUT2 (SEQ ID NO: 126) | TAGAGGTGTGGGTTAT (SEQ ID NO: 2124) |
| 219 | ONECUT2 (SEQ ID NO: 126) | TAGAGGCGCGGGTTAT (SEQ ID NO: 2123) |
| 220 | ONECUT2 (SEQ ID NO: 126) | TAGAGGTGTGGGTTAT (SEQ ID NO: 2124) |
| 221 | CYP2D6 (SEQ ID NO: 129) | GAGATCGCGTTTTCGT (SEQ ID NO: 2125) |
| 222 | CYP2D6 (SEQ ID NO: 129) | AGAGATTGTGTTTTGT (SEQ ID NO: 2126) |
| 223 | CYP2D6 (SEQ ID NO: 129) | ATTCGCGGCGAGGATA (SEQ ID NO: 2127) |
| 224 | CYP2D6 (SEQ ID NO: 129) | GATTTGTGGTGAGGAT (SEQ ID NO: 2128) |
| 225 | CYP2D6 (SEQ ID NO: 129) | GTCGTTTCGGGGACGT (SEQ ID NO: 2129) |
| 226 | CYP2D6 (SEQ ID NO: 129) | GTTGTTTTGGGGATGTG (SEQ ID NO: 2130) |
| 227 | CYP2D6 (SEQ ID NO: 129) | TAAGTAGCGTCGATAG (SEQ ID NO: 2131) |
| 228 | CYP2D6 (SEQ ID NO: 129) | AAGTAGTGTTGATAGGG (SEQ ID NO: 2132) |
| 229 | WBP11 (SEQ ID NO: 137) | TTACGAGAAGCGGGTA (SEQ ID NO: 2133) |
| 230 | WBP11 (SEQ ID NO: 137) | ATTATGAGAAGTGGGTA (SEQ ID NO: 2134) |
| 231 | WBP11 (SEQ ID NO: 137) | AGGGGGCGATTTTCGG (SEQ ID NO: 2135) |
| 232 | WBP11 (SEQ ID NO: 137) | TAGGGGTGATTTTTGG (SEQ ID NO: 2136) |
| 233 | WBP11 (SEQ ID NO: 137) | TTAGCGTCGTTTGATT (SEQ ID NO: 2137) |
| 234 | WBP11 (SEQ ID NO: 137) | TTTTAGTGTTGTTTGATT (SEQ ID NO: 2138) |
| 235 | WBP11 (SEQ ID NO: 137) | AGTTCGTTTTATTGCGT (SEQ ID NO: 2139) |
| 236 | WBP11 (SEQ ID NO: 137) | GAGTTTGTTTTATTGTGT (SEQ ID NO: 2140) |

TABLE 3

Table 3. Predictive score for response[a].

| Factor | n | P | OR[b] | (95% CI)[c] |
|---|---|---|---|---|
| Traditional factors-based score[d], ($\chi^2$ = 10.9, 3 degrees of freedom) | | | | |
| q1 q2 q3 q4 | 50 50 50 50 | 0.013 | 1 1.51 3.16 2.90 | (0.68-3.38) (1.40-7.15) (1.29-6.53) |

TABLE 3-continued

Table 3. Predictive score for response[a].

| Factor | n | P | OR[b] | (95% CI)[c] |
|---|---|---|---|---|
| Methylation-based score[e], ($\chi^2$ = 44.3, 3 degrees of freedom) | | | | |
| q1 q2 q3 q4 | 50 50 50 50 | <0.001 | 1 1.47 5.52 13.0 | (0.62-3.47) (2.34-13.1) (4.97-33.8) |

[a]Logistic regression was used to test the strength of a relationship of a factor with the type of response to tamoxifen treatment;
[b]Odds ratio;
[c]95% confidence interval;
[d]Score based on multivariable analysis of the traditional factors age (>70 yr, 55-70 yr, 41-55 yr versus ≦40 yr) dominant site of relapse (relapse to viscera or bone versus soft tissue), disease-free interval (>12 months versus ≦12 months), and log ER values. The score was divided into groups (q1-q4) based on the 25th, 50th and 75th percentile values;
[e]Score based on the DNA methylation status of the 5 independent predicting genes PSA-T, STMN1, GRIN2D, TGFBR2 and S100A2. The score was divided into groups, q1-q4, same as for the traditional factors-based score.

TABLE 4

| Sample | Response | LC assay methylation % | Chip |
|---|---|---|---|
| 1 | Remission | 80 | + |
| 2 | Remission | 27 | + |
| 3 | Remission (outlier) | 3 | − |
| 4 | Remission | 88 | + |
| 5 | Remission | 68 | + |
| 6 | Remission | 62 | + |
| 7 | Remission | 60 | + |
| 8 | Remission | 83 | + |
| 9 | Remission | 56 | + |
| 10 | Remission (outlier) | 0 | − |
| 11 | Remission | 0 | + |
| 12 | Remission | 0 | + |
| 13 | Progressive Disease | 0 | − |
| 14 | Progressive Disease | 0 | − |
| 15 | Progressive Disease | 4 | − |
| 16 | Progressive Disease | 7 | − |
| 17 | Progressive Disease (outlier) | 0 | + |
| 18 | Progressive Disease | 0 | − |
| 19 | Progressive Disease | 0 | − |
| 20 | Progressive Disease | 0 | − |
| 21 | Progressive Disease | 0 | − |
| 22 | Progressive Disease | 0 | − |
| 23 | Progressive Disease (outlier) | 0 | + |
| 24 | Progressive Disease | 0 | − |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08101359B2). An electronic copy of the "Sequence Listing" will also be available from the USPTO upon request and payment of the fee set forth in 37 CFR 1.19(b)(3).

The invention claimed is:

1. A method for detecting the risk of relapse in a human subject having an estrogen receptor-positive breast cancer following adjuvant therapeutic treatment, comprising:
    i) obtaining from the subject, a biological sample comprising breast cancer cell genomic DNA to be analyzed for methylation status, wherein the treatment comprises the administration of tamoxifen;
    ii) contacting the genomic DNA in the sample with at least one agent for distinguishing between methylated and non-methylated CpG dinucleotide sequences;
    iii) determining the CpG methylation status of at least one to six CpG dinucleotides of SEQ ID NO:83 or complements thereof; and
    iv) determining the methylation status of DNA in iii) wherein hypomethylation of the DNA in iii) is indicative of a low risk for relapse following adjuvant therapeutic treatment and hypermethylation of the DNA in iii) is indicative of a high risk for relapse following adjuvant therapeutic treatment, thereby detecting the risk of relapse following adjuvant therapeutic treatment.

2. The method of claim 1, wherein the breast cancer is selected from the group consisting of ductal carcinoma in situ, lobular carcinoma, colloid carcinoma, tubular carcinoma, medullary carcinoma, metaplastic carcinoma, intraductal carcinoma in situ, lobular carcinoma in situ and papillary carcinoma in situ.

3. The method of claim 1, wherein the subject is also progesterone receptor positive.

4. The method of claim 1, wherein the therapeutic treatment is for the treatment of a relapse or metastatic breast cancer.

5. The method of claim 1, wherein the subject did not receive a chemotherapeutic treatment.

6. A method for detecting the risk of relapse in a human subject having an estrogen receptor-positive breast cancer following adjuvant therapeutic treatment, comprising:
    i) obtaining from the subject, a biological sample comprising breast cancer cell genomic DNA to be analyzed for methylation status, wherein the treatment comprises the administration of tamoxifen;
    ii) isolating the genomic DNA from the sample;
    iii) contacting the genomic DNA in the sample with at least one agent for distinguishing between methylated and non-methylated CpG dinucleotide sequences to provide at least one pretreated DNA sequence;
    iv) amplifying the at least one pretreated DNA sequence, or a portion thereof, selected from the group consisting of SEQ ID NOS:411, 412, 685, 686, and complements thereof to provide DNA amplificates; and
    v) determining the CpG methylation status of at least one to six CpG dinucleotides of the DNA amplificates, wherein hypomethylaton of the DNA amplificates is indicative of a low risk for relapse following adjuvant therapeutic treatment and hypermethylation of the DNA amplificates is indicative of a high risk for relapse following adjuvant therapeutic treatment, thereby detecting the risk of relapse following adjuvant endocrine therapeutic treatment.

7. The method of claim 6, wherein the CpG methylation status determination comprises sequencing.

8. The method of claim 6, wherein amplifying comprises use of methylation-specific primers.

9. The method of claim 6, wherein amplifying comprises use of at least one nucleic acid molecule or peptide nucleic acid molecule comprising a contiguous sequence at least 9 nucleotides in length that is complementary to, or hybridizes under moderately stringent or stringent conditions to a sequence selected from the group consisting of SEQ ID NOS: 411, 412, 685, 686, and complements thereof, wherein the nucleic acid molecule or peptide nucleic acid molecule suppresses amplification of the sequence to which it is hybridized.

10. The method of claim 6, wherein the agent is selected from the group consisting of bisulfite, hydrogen sulfite and disulfite, or a combination thereof.

11. A method for detecting the risk of relapse in a human subject having an estrogen receptor-positive breast cancer following adjuvant therapeutic treatment, comprising:
   i) obtaining from the subject, a biological sample comprising breast cancer cell genomic DNA to be analyzed for methylation status, wherein the treatment comprises the administration of tamoxifen;
   ii) isolating the genomic DNA from the sample;
   iii) digesting the isolated genomic DNA, or a portion thereof, comprising SEQ ID NO:83, and complements thereof, with one or more methylation-sensitive restriction enzymes; and
   iv) determining the CpG methylation status of at least one to six CpG dinucleotides of DNA fragments of SEQ ID NO: 83 generated in iii);
      wherein hypomethylation of SEQ ID NO: 83 is indicative of a low risk for relapse following adjuvant therapeutic treatment and hypermethylation of SEQ ID NO: 83 is indicative of a high risk for relapse following adjuvant therapeutic treatment, thereby detecting the risk of relapse following adjuvant endocrine therapeutic treatment.

12. The method of claim 11, further comprising amplifying the DNA fragments generated.

13. The method of claim 6 or 11, wherein the biological sample is selected from the group consisting of cells, cellular components containing DNA, histological slides, biopsies, tissue embedded in paraffin, breast tissues, blood, plasma, lymphatic fluid, lymphatic tissue, duct cells, ductal lavage fluid, nipple aspiration fluid, bone marrow, and combinations thereof.

14. The method of any of claim 1, 6 or 11, wherein the methylation of at least one, at least three or at least six CpG dinucleotides is determined.

* * * * *